US010662245B2

(12) United States Patent
Igawa et al.

(10) Patent No.: US 10,662,245 B2
(45) Date of Patent: *May 26, 2020

(54) METHODS OF REDUCING IL-6 ACTIVITY FOR DISEASE TREATMENT

(71) Applicant: Chugai Seiyaku Kabushiki Kaisha, Tokyo (JP)

(72) Inventors: Tomoyuki Igawa, Shizuoka (JP); Shinya Ishii, Shizuoka (JP); Atsuhiko Maeda, Shizuoka (JP); Mika Sakurai, Shizuoka (JP); Tetsuo Kojima, Shizuoka (JP); Tatsuhiko Tachibana, Shizuoka (JP); Hirotake Shiraiwa, Shizuoka (JP); Hiroyuki Tsunoda, Shizuoka (JP); Yoshinobu Higuchi, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/520,423

(22) Filed: Oct. 22, 2014

(65) Prior Publication Data

US 2015/0166666 A1      Jun. 18, 2015

Related U.S. Application Data

(60) Continuation of application No. 13/524,528, filed on Jun. 15, 2012, now abandoned, which is a division of application No. 12/680,087, filed as application No. PCT/JP2009/066590 on Sep. 25, 2009, now Pat. No. 8,562,991.

(30) Foreign Application Priority Data

Sep. 26, 2008  (JP) ................. 2008-248213
Mar. 13, 2009  (JP) ................. 2009-060806
Mar. 19, 2009  (JP) ................. 2009-067925

(51) Int. Cl.
*A61K 39/395* (2006.01)
*C07K 16/28* (2006.01)
*C07K 16/46* (2006.01)
*A61K 39/00* (2006.01)

(52) U.S. Cl.
CPC ........ *C07K 16/2866* (2013.01); *C07K 16/461* (2013.01); *A61K 39/00* (2013.01); *A61K 2039/505* (2013.01); *C07K 2317/24* (2013.01); *C07K 2317/41* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,689,299 A | 8/1987 | Insel |
| 4,801,687 A | 1/1989 | Ngo |
| 5,126,250 A | 6/1992 | McDonough et al. |
| 5,202,253 A | 4/1993 | Esmon et al. |
| 5,322,678 A | 6/1994 | Morgan et al. |
| 5,501,854 A | 3/1996 | Raso |
| 5,585,089 A | 12/1996 | Queen et al. |
| 5,639,641 A | 6/1997 | Pedersen et al. |
| 5,670,373 A | 9/1997 | Kishimoto |
| 5,795,965 A | 8/1998 | Tsuchiya et al. |
| 5,817,790 A | 10/1998 | Tsuchiya et al. |
| 5,830,478 A | 11/1998 | Raso et al. |
| 5,935,935 A | 8/1999 | Connelly et al. |
| 5,945,311 A | 8/1999 | Lindhofer et al. |
| 5,990,286 A | 11/1999 | Khawli et al. |
| 6,074,642 A | 6/2000 | Wang et al. |
| 6,309,636 B1 | 10/2001 | do Couto et al. |
| 6,329,511 B1 | 12/2001 | Vasquez et al. |
| 6,485,943 B2 | 11/2002 | Stevens et al. |
| 6,677,436 B1 | 1/2004 | Sato et al. |

(Continued)

FOREIGN PATENT DOCUMENTS

| | | |
|---|---|---|
| AR | 068564 | 11/2009 |
| CA | 1 332 367 | 10/1994 |

(Continued)

OTHER PUBLICATIONS

Beck et al., "Strategies and challenges for the next generation of therapeutic antibodies," Nat Rev Immunol., 10(5):345-52 (2010).

(Continued)

*Primary Examiner* — Dong Jiang
(74) *Attorney, Agent, or Firm* — Fish & Richardson P.C.

(57) ABSTRACT

The present invention provides pharmaceutical compositions comprising second-generation molecules that are superior than TOCILIZUMAB, by altering the amino acid sequences of the variable and constant regions of TOCILIZUMAB, which is a humanized anti-IL-6 receptor IgG1 antibody, to enhance the antigen-neutralizing ability and increase the pharmacokinetics, so that the therapeutic effect is exerted with a less frequency of administration, and the immunogenicity, safety and physicochemical properties (stability and homogeneity) are improved. The present invention also provides methods for producing these pharmaceutical compositions.

The present inventors have successfully generated second-generation molecules that are superior to TOCILIZUMAB by appropriately combining amino acid sequence alterations in the CDR domains, variable regions, and constant regions.

25 Claims, 22 Drawing Sheets

Specification includes a Sequence Listing.

(56) References Cited

U.S. PATENT DOCUMENTS

| | | |
|---|---|---|
| 6,723,319 B1 | 4/2004 | Ito et al. |
| 6,737,056 B1 | 5/2004 | Presta |
| 6,821,505 B2 | 11/2004 | Ward |
| 6,884,879 B1 | 4/2005 | Baca et al. |
| 6,913,747 B1 | 7/2005 | Co et al. |
| 7,052,873 B2 | 5/2006 | Tsuchiya |
| 7,122,637 B2 | 10/2006 | Presta |
| 7,217,797 B2 | 5/2007 | Hinton et al. |
| 7,276,585 B2 | 10/2007 | Lazar et al. |
| 7,479,543 B2 | 1/2009 | Tsuchiya et al. |
| 8,217,147 B2 | 7/2012 | Stavenhagen et al. |
| 8,329,867 B2 | 12/2012 | Lazar et al. |
| 8,367,805 B2 | 2/2013 | Chamberlain et al. |
| 8,470,316 B2 | 6/2013 | Yasunami |
| 8,562,991 B2 | 10/2013 | Igawa et al. |
| 8,623,355 B2 | 1/2014 | Okada et al. |
| 8,771,686 B2 | 7/2014 | Ishida |
| 8,945,558 B2 | 2/2015 | Kobara |
| 9,029,515 B2 | 5/2015 | Pons et al. |
| 9,079,949 B1 | 7/2015 | Andrien et al. |
| 9,096,651 B2 | 8/2015 | Igawa et al. |
| 9,228,017 B2 | 1/2016 | Igawa et al. |
| 9,260,516 B2 | 2/2016 | Nishimoto et al. |
| 9,688,762 B2 | 6/2017 | Igawa et al. |
| 9,828,429 B2 | 11/2017 | Igawa et al. |
| 9,868,948 B2 | 1/2018 | Igawa et al. |
| 9,890,377 B2 | 2/2018 | Igawa et al. |
| 10,066,018 B2 | 9/2018 | Igawa et al. |
| 10,253,091 B2 | 4/2019 | Igawa et al. |
| 10,472,623 B2 | 11/2019 | Igawa et al. |
| 2001/0001663 A1 | 5/2001 | Kishimoto et al. |
| 2002/0098193 A1 | 7/2002 | Ward |
| 2002/0142374 A1 | 10/2002 | Gallo et al. |
| 2002/0164339 A1 | 11/2002 | Do et al. |
| 2002/0187150 A1 | 12/2002 | Mihara et al. |
| 2003/0059937 A1 | 3/2003 | Ruben et al. |
| 2003/0224397 A1 | 12/2003 | Lowman et al. |
| 2004/0018540 A1 | 1/2004 | Yamamura et al. |
| 2004/0071706 A1 | 4/2004 | Ito et al. |
| 2004/0081651 A1 | 4/2004 | Karpusas et al. |
| 2004/0133357 A1 | 7/2004 | Zhong et al. |
| 2004/0236080 A1 | 11/2004 | Aburatani et al. |
| 2005/0014934 A1 | 1/2005 | Hinton et al. |
| 2005/0095243 A1 | 5/2005 | Chan et al. |
| 2005/0118163 A1 | 6/2005 | Mizushima et al. |
| 2005/0130224 A1 | 6/2005 | Saito et al. |
| 2005/0142133 A1 | 6/2005 | Lazar et al. |
| 2005/0142635 A1 | 6/2005 | Tsuchiya et al. |
| 2005/0214278 A1 | 9/2005 | Kakuta et al. |
| 2005/0244403 A1 | 11/2005 | Lazar et al. |
| 2005/0260711 A1 | 11/2005 | Datta et al. |
| 2005/0261229 A1 | 11/2005 | Gillies et al. |
| 2006/0014156 A1 | 1/2006 | Rabbani et al. |
| 2006/0019342 A1 | 1/2006 | Dall Acqua et al. |
| 2006/0063228 A1 | 3/2006 | Kasaian et al. |
| 2006/0134113 A1 | 6/2006 | Mihara et al. |
| 2006/0134709 A1 | 6/2006 | Stavenhagen et al. |
| 2006/0141456 A1 | 6/2006 | Edwards et al. |
| 2006/0153860 A1 | 7/2006 | Cho et al. |
| 2006/0194280 A1 | 8/2006 | Dillon et al. |
| 2006/0275282 A1 | 12/2006 | Moore et al. |
| 2006/0292147 A1 | 12/2006 | Yoshizaki et al. |
| 2007/0036785 A1 | 2/2007 | Kishimoto et al. |
| 2007/0037734 A1 | 2/2007 | Rossi et al. |
| 2007/0041978 A1 | 2/2007 | Hattori et al. |
| 2007/0059312 A1 | 3/2007 | Baca et al. |
| 2007/0134234 A1 | 6/2007 | Smith et al. |
| 2007/0148164 A1 | 6/2007 | Farrington et al. |
| 2007/0160598 A1 | 7/2007 | Dennis et al. |
| 2007/0212357 A1 | 9/2007 | Pons et al. |
| 2007/0269371 A1 | 11/2007 | Krummen et al. |
| 2007/0280945 A1 | 12/2007 | Stevens et al. |
| 2008/0075712 A1 | 3/2008 | Hattori et al. |
| 2008/0145367 A1 | 6/2008 | Bove et al. |
| 2008/0166756 A1 | 7/2008 | Tsuchiya et al. |
| 2009/0263392 A1 | 10/2009 | Igawa et al. |
| 2009/0269335 A1 | 10/2009 | Nakashima et al. |
| 2009/0291076 A1 | 11/2009 | Morichika et al. |
| 2009/0324589 A1 | 12/2009 | Igawa et al. |
| 2010/0003254 A1 | 1/2010 | Hattori et al. |
| 2010/0004429 A1 | 1/2010 | Kai et al. |
| 2010/0008907 A1 | 1/2010 | Nishimoto et al. |
| 2010/0015133 A1 | 1/2010 | Igawa et al. |
| 2010/0055092 A1 | 3/2010 | Hasegawa et al. |
| 2010/0061986 A1 | 3/2010 | Takahashi |
| 2010/0098730 A1 | 4/2010 | Lowman et al. |
| 2010/0216187 A1 | 8/2010 | Lasters et al. |
| 2010/0239577 A1 | 9/2010 | Igawa et al. |
| 2010/0247523 A1 | 9/2010 | Kano et al. |
| 2010/0292443 A1 | 11/2010 | Sabbadini et al. |
| 2010/0297697 A1 | 11/2010 | Ambrosius et al. |
| 2010/0298542 A1 | 11/2010 | Igawa et al. |
| 2010/0316636 A1 | 12/2010 | Radin et al. |
| 2011/0044986 A1 | 2/2011 | Biere-Citron et al. |
| 2011/0076275 A1 | 3/2011 | Igawa et al. |
| 2011/0098450 A1 | 4/2011 | Igawa et al. |
| 2011/0111406 A1 | 5/2011 | Igawa et al. |
| 2011/0150869 A1 | 6/2011 | Mitsunaga |
| 2011/0150888 A1 | 6/2011 | Foltz et al. |
| 2011/0245473 A1 | 10/2011 | Igawa et al. |
| 2012/0065379 A1 | 3/2012 | Igawa et al. |
| 2012/0071634 A1 | 3/2012 | Igawa et al. |
| 2012/0183539 A1 | 7/2012 | Maeda |
| 2012/0238729 A1 | 9/2012 | Kuramochi et al. |
| 2012/0253016 A1 | 10/2012 | Igawa et al. |
| 2012/0301460 A1 | 11/2012 | Bao et al. |
| 2013/0011866 A1 | 1/2013 | Igawa et al. |
| 2013/0101581 A1 | 4/2013 | Kuramochi et al. |
| 2013/0131319 A1 | 5/2013 | Igawa et al. |
| 2013/0202588 A1 | 8/2013 | Nishimura |
| 2013/0303396 A1 | 11/2013 | Igawa et al. |
| 2013/0317203 A1 | 11/2013 | Igawa et al. |
| 2013/0336963 A1 | 12/2013 | Igawa et al. |
| 2014/0105889 A1 | 4/2014 | Igawa et al. |
| 2014/0234340 A1 | 8/2014 | Igawa et al. |
| 2014/0363428 A1 | 12/2014 | Igawa et al. |
| 2015/0050269 A1 | 2/2015 | Igawa et al. |
| 2015/0056182 A1 | 2/2015 | Igawa et al. |
| 2015/0274809 A1 | 10/2015 | Igawa et al. |
| 2015/0284465 A1 | 10/2015 | Igawa et al. |
| 2015/0299313 A1 | 10/2015 | Igawa et al. |
| 2015/0315278 A1 | 11/2015 | Igawa et al. |
| 2015/0353630 A1 | 12/2015 | Igawa et al. |
| 2016/0039912 A1 | 2/2016 | Mimoto et al. |
| 2016/0046693 A1 | 2/2016 | Igawa et al. |
| 2016/0139117 A1 | 5/2016 | Yamamura et al. |
| 2016/0159915 A1 | 6/2016 | Igawa et al. |
| 2016/0244526 A1 | 8/2016 | Igawa et al. |
| 2017/0002080 A1 | 1/2017 | Igawa et al. |
| 2017/0022270 A1 | 1/2017 | Igawa et al. |
| 2018/0142027 A1 | 5/2018 | Igawa et al. |
| 2018/0148509 A1 | 5/2018 | Kakehi et al. |
| 2018/0149573 A1 | 5/2018 | Yamamura et al. |
| 2018/0258161 A1 | 9/2018 | Igawa et al. |
| 2019/0085085 A1 | 3/2019 | Igawa |
| 2019/0211081 A1 | 7/2019 | Igawa et al. |

FOREIGN PATENT DOCUMENTS

| | | |
|---|---|---|
| CA | 2 203 182 | 5/1996 |
| CA | 2 443 294 | 10/2002 |
| CA | 2 523 577 | 11/2004 |
| CA | 2 531 482 | 1/2005 |
| CA | 2 549 467 | 7/2005 |
| CA | 2 560 953 | 9/2005 |
| CA | 2 625 773 | 4/2007 |
| CA | 2 626 688 | 4/2007 |
| CA | 2 647 846 | 10/2007 |
| CA | 2 648 644 | 10/2007 |
| CA | 2 700 394 | 4/2009 |
| CA | 2 700 498 | 4/2009 |
| CA | 2 700 986 | 4/2009 |
| CN | 101849006 | 9/2010 |
| CN | 103476793 | 12/2013 |

(56) References Cited

FOREIGN PATENT DOCUMENTS

| | | |
|---|---|---|
| CN | 101874042 | 9/2018 |
| EP | 0 182 495 | 5/1986 |
| EP | 0 361 902 | 4/1990 |
| EP | 0 329 185 | 4/1994 |
| EP | 0 628 639 | 12/1994 |
| EP | 0 783 893 | 7/1997 |
| EP | 0 791 359 | 8/1997 |
| EP | 0 983 767 | 3/2000 |
| EP | 1 004 315 | 5/2000 |
| EP | 1 069 185 | 1/2001 |
| EP | 1 074 268 | 2/2001 |
| EP | 1 334 731 | 8/2003 |
| EP | 1 374 900 | 1/2004 |
| EP | 1 510 943 | 3/2005 |
| EP | 1 690 550 | 8/2006 |
| EP | 1 701 979 | 9/2006 |
| EP | 1 707 215 | 10/2006 |
| EP | 1 712 237 | 10/2006 |
| EP | 2 236 604 | 10/2006 |
| EP | 1 728 801 | 12/2006 |
| EP | 1 733 740 | 12/2006 |
| EP | 1 773 391 | 4/2007 |
| EP | 1 601 697 | 5/2007 |
| EP | 1 847 602 | 10/2007 |
| EP | 1 870 459 | 12/2007 |
| EP | 1 941 907 | 7/2008 |
| EP | 1 941 908 | 7/2008 |
| EP | 1 967 207 | 9/2008 |
| EP | 1 967 209 | 9/2008 |
| EP | 1 977 763 | 10/2008 |
| EP | 1 990 060 | 11/2008 |
| EP | 2 006 381 | 12/2008 |
| EP | 2 009 101 | 12/2008 |
| EP | 2 031 064 | 3/2009 |
| EP | 2 123 302 | 11/2009 |
| EP | 2 174 667 | 4/2010 |
| EP | 2 194 066 | 6/2010 |
| EP | 2 196 220 | 6/2010 |
| EP | 2 196 541 | 6/2010 |
| EP | 2 202 245 | 6/2010 |
| EP | 2 206 775 | 7/2010 |
| EP | 2 275 443 | 1/2011 |
| EP | 2 305 306 | 4/2011 |
| EP | 2 330 193 | 6/2011 |
| EP | 2 409 991 | 1/2012 |
| EP | 2 578 233 | 4/2013 |
| EP | 2 639 305 | 9/2013 |
| JP | S61-117457 | 6/1986 |
| JP | S63-52890 | 3/1988 |
| JP | 2-028200 | 1/1990 |
| JP | 2-163096 | 6/1990 |
| JP | H02-163085 | 6/1990 |
| JP | H03-500644 | 2/1991 |
| JP | 07-67688 | 3/1995 |
| JP | 09-506001 | 6/1997 |
| JP | 2002-505086 | 2/2002 |
| JP | 2004-028926 | 1/2004 |
| JP | 2004-511426 | 4/2004 |
| JP | 2005-501514 | 1/2005 |
| JP | 2005-101105 | 3/2005 |
| JP | 2005-535341 | 11/2005 |
| JP | 2005-378266 | 12/2005 |
| JP | 2006-512087 | 4/2006 |
| JP | 2007-525171 | 9/2007 |
| JP | 2010-505436 | 2/2010 |
| JP | 5144499 | 2/2013 |
| JP | 2013-518131 | 5/2013 |
| JP | 2013-165716 | 8/2013 |
| JP | 2013-541594 | 11/2013 |
| JP | 5334319 | 11/2013 |
| JP | 5484060 | 5/2014 |
| JP | 5717624 | 5/2015 |
| JP | 2015-130883 | 7/2015 |
| JP | 5787446 | 9/2015 |
| KR | 2006/0010765 | 2/2006 |
| KR | 2007/0035482 | 3/2007 |
| KR | 2007/0068385 | 6/2007 |
| KR | 2008/0098504 | 11/2008 |
| KR | 2010/0074220 | 7/2010 |
| KR | 2010/0074221 | 7/2010 |
| RU | 2147442 | 4/2000 |
| RU | 2195960 | 1/2003 |
| RU | 2225721 | 3/2004 |
| RU | 2232773 | 7/2004 |
| RU | 2266298 | 12/2005 |
| RU | 2430111 | 9/2011 |
| RU | 2010/116152 | 11/2011 |
| TW | 201021829 | 6/2010 |
| WO | WO 89/01343 | 2/1989 |
| WO | WO 91/12023 | 8/1991 |
| WO | WO 92/19759 | 11/1992 |
| WO | WO 95/014710 | 6/1995 |
| WO | WO 95/33844 | 12/1995 |
| WO | WO 96/11020 | 4/1996 |
| WO | WO 96/12503 | 5/1996 |
| WO | WO 96/27011 | 9/1996 |
| WO | WO 97/09351 | 3/1997 |
| WO | WO 97/20858 | 6/1997 |
| WO | WO 98/03546 | 1/1998 |
| WO | WO 98/42377 | 10/1998 |
| WO | WO 99/08707 | 2/1999 |
| WO | WO 99/018212 | 4/1999 |
| WO | WO 99/43713 | 9/1999 |
| WO | WO 99/47170 | 9/1999 |
| WO | WO 99/51743 | 10/1999 |
| WO | WO 99/58572 | 11/1999 |
| WO | WO 00/14220 | 3/2000 |
| WO | WO 01/30854 | 5/2001 |
| WO | WO 01/82899 | 11/2001 |
| WO | WO 02/34292 | 5/2002 |
| WO | WO 02/060919 | 8/2002 |
| WO | WO 02/072605 | 9/2002 |
| WO | WO 02/080969 | 10/2002 |
| WO | WO 03/000883 | 1/2003 |
| WO | WO 03/020949 | 3/2003 |
| WO | WO 03/068259 | 8/2003 |
| WO | WO 03/068260 | 8/2003 |
| WO | WO 2003/070760 | 8/2003 |
| WO | WO 03/105757 | 12/2003 |
| WO | WO 2003/107009 | 12/2003 |
| WO | WO 2004/016740 | 2/2004 |
| WO | WO 2004/035752 | 4/2004 |
| WO | WO 2004/039826 | 5/2004 |
| WO | WO 2004/068931 | 8/2004 |
| WO | WO 2004/092219 | 10/2004 |
| WO | WO 2004/096273 | 11/2004 |
| WO | WO 2004/113387 | 12/2004 |
| WO | WO 2005/005604 | 1/2005 |
| WO | WO 2005/035753 | 4/2005 |
| WO | WO 2005/035754 | 4/2005 |
| WO | WO 2005/035756 | 4/2005 |
| WO | WO 2005/037315 | 4/2005 |
| WO | WO 2005/047327 | 5/2005 |
| WO | WO 2005/056606 | 6/2005 |
| WO | WO 2005/059106 | 6/2005 |
| WO | WO 2005/061000 | 7/2005 |
| WO | WO 2005/067620 | 7/2005 |
| WO | WO 2005/080429 | 9/2005 |
| WO | WO 2005/090405 | 9/2005 |
| WO | WO 2005/092925 | 10/2005 |
| WO | WO 2005/112564 | 12/2005 |
| WO | WO 2005/123126 | 12/2005 |
| WO | WO 2006/004663 | 1/2006 |
| WO | WO 2006/019447 | 2/2006 |
| WO | WO 2006/023144 | 3/2006 |
| WO | WO 2006/030200 | 3/2006 |
| WO | WO 2006/030220 | 3/2006 |
| WO | WO 2006/044908 | 4/2006 |
| WO | WO 2006/047340 | 5/2006 |
| WO | WO 2006/047350 | 5/2006 |
| WO | WO 2006/050491 | 5/2006 |
| WO | WO 2006/066598 | 6/2006 |
| WO | WO 2006/067913 | 6/2006 |
| WO | WO 2006/070286 | 7/2006 |

(56) References Cited

FOREIGN PATENT DOCUMENTS

| | | |
|---|---|---|
| WO | WO 2006/071877 | 7/2006 |
| WO | WO 2006/075668 | 7/2006 |
| WO | WO 2006/106905 | 10/2006 |
| WO | WO 2006/109592 | 10/2006 |
| WO | WO 2006/119115 | 11/2006 |
| WO | WO 2006/121852 | 11/2006 |
| WO | WO 2007/024535 | 3/2007 |
| WO | WO 2007/043641 | 4/2007 |
| WO | WO 2007/046489 | 4/2007 |
| WO | WO 2007/058194 | 5/2007 |
| WO | WO 2007/060411 | 5/2007 |
| WO | WO 2007/061029 | 5/2007 |
| WO | WO 2007/074880 | 7/2007 |
| WO | WO 2007/076524 | 7/2007 |
| WO | WO 2007/086490 | 8/2007 |
| WO | WO 2007/092772 | 8/2007 |
| WO | WO 2007/108559 | 9/2007 |
| WO | WO 2007/114319 | 10/2007 |
| WO | WO 2007/114325 | 10/2007 |
| WO | WO 2007/116962 | 10/2007 |
| WO | WO 2007/137984 | 12/2007 |
| WO | WO 2007/142325 | 12/2007 |
| WO | WO 2007/143168 | 12/2007 |
| WO | WO 2008/020079 | 2/2008 |
| WO | WO 2008/043822 | 4/2008 |
| WO | WO 2008/060785 | 5/2008 |
| WO | WO 2008/090901 | 7/2008 |
| WO | WO 2008/092117 | 7/2008 |
| WO | WO 2008/145141 | 12/2008 |
| WO | WO 2009/006338 | 1/2009 |
| WO | WO 2009/010539 | 1/2009 |
| WO | WO 2009/014263 | 1/2009 |
| WO | WO 2009/036209 | 3/2009 |
| WO | WO 2009/041062 | 4/2009 |
| WO | WO 2009/041613 | 4/2009 |
| WO | WO 2009/041621 | 4/2009 |
| WO | WO 2009/041643 | 4/2009 |
| WO | WO 2009/041734 | 4/2009 |
| WO | WO 2009/044774 | 4/2009 |
| WO | WO 2009/052439 | 4/2009 |
| WO | WO 2009/072604 | 6/2009 |
| WO | WO 2009/100309 | 8/2009 |
| WO | WO 2009/125825 | 10/2009 |
| WO | WO 2009/139822 | 11/2009 |
| WO | WO 2009/148148 | 12/2009 |
| WO | WO 2010/035769 | 4/2010 |
| WO | WO 2010/065078 | 6/2010 |
| WO | WO 2010/106812 | 9/2010 |
| WO | WO 2010/107108 | 9/2010 |
| WO | WO 2010/107109 | 9/2010 |
| WO | WO 2010/107110 | 9/2010 |
| WO | WO 2011/013786 | 2/2011 |
| WO | WO 2011/094593 | 8/2011 |
| WO | WO 2011/111007 | 9/2011 |
| WO | WO 2011/149046 | 12/2011 |
| WO | WO 2011/149051 | 12/2011 |
| WO | WO 2012/063875 | 5/2012 |
| WO | WO 2012/064627 | 5/2012 |
| WO | WO 2012/073992 | 6/2012 |
| WO | WO 2012/118750 | 9/2012 |
| WO | WO 2014/028354 | 2/2014 |
| WO | WO 2014/144080 | 9/2014 |
| WO | WO 2014/144575 | 9/2014 |
| WO | WO 2014/200018 | 12/2014 |
| WO | WO 2016/136933 | 9/2016 |
| WO | WO 2016/186154 | 11/2016 |

OTHER PUBLICATIONS

Chaparro-Riggers et al., "Increasing serum half-life and extending cholesterol lowering in vivo by engineering antibody with pH-sensitive binding to PCSK9," J Biol Chem., 287(14):11090-7 (2012).
Datta-Mannan et al., "Monoclonal antibody clearance. Impact of modulating the interaction of IgG with the neonatal Fc receptor," J Biol Chem., 282(3):1709-17 (2007).
Devanaboyina et al., "The effect of pH dependence of antibody-antigen interactions on subcellular trafficking dynamics," MAbs, 5(6):851-9 (2013).
Drake et al., "Chapter 5: Biophysical Considerations for Development of Antibody-Based Therapeutics," Biophysical Considerations for Development of Antibody-Based Therapeutics, Springer Springer Science+Business Media New York, 95-7 (2012).
Feinberg et al., "Mechanism of pH-dependent N-acetylgalactosamine binding by a functional mimic of the hepatocyte asialoglycoprotein receptor," J Biol Chem., 275(45):35176-84 (2000).
Finkelman et al., "Anti-cytokine antibodies as carrier proteins. Prolongation of in vivo effects of exogenous cytokines by injection of cytokine-anti-cytokine antibody complexes," J Immunol., 151(3):1235-44 (1993).
Igawa et al., "Antibody optimization technologies for developing next generation antibody therapeutics," Bio Industry, 28(7):15-21 (2011) (with English translation).
Igawa et al., "Engineered monoclonal antibody with novel antigen-sweeping activity in vivo," PLoS One, 8(5):e63236 (2013).
Ishihara et al., "Accelerated purification process development of monoclonal antibodies for shortening time to clinic. Design and case study of chromatography processes," J Chromatogr A., 1176(1-2):149-56 (2007).
Ishii et al., "FcRn, a critical regulator of antibody pharmacokinetics," Folia Pharmacol. Jpn., 136(5):280-284 (2010) (with English translation).
Lee et al., "High-affinity human antibodies from phage-displayed synthetic Fab libraries with a single framework scaffold," J Mol Biol., 340(5):1073-93 (2004).
Lin et al., "Preclinical pharmacokinetics, interspecies scaling, and tissue distribution of a humanized monoclonal antibody against vascular endothelial growth factor," J Pharmacol Exp Ther., 288(1):371-8 (1999).
Padlan et al., "Structure of an antibody-antigen complex: crystal structure of the HyHEL-10 Fab-lysozyme complex," Proc. Natl. Acad. Sci. USA, 86:5938-5942 (1989).
Pakula et al., "Genetic Analysis of Protein Stability and Function," Annu. Rev. Genet., 23:289-310 (1989).
Philippovich, "Fundamentals of Biochemistry," edition Higher school, Moscow, p. 31 (1969).
Pokrovsky, vol. 1 A-Infant, Soviet Encyclopedia, p. 146 (1991).
Roitt et al., Immunology, M., Mir, (2000), pp. 110-111 (in Russian, with what is believed to be a published English equivalent of those pages taken from Roitt et al., "Antibody Structure and Function," Immunology, Fifth Ed., (1998), pp. 80-81).
Sarkar et al., Rational cytokine design for increased lifetime and enhanced potency using pH-activated "histidine switching," Nat Biotechnol., 20(9):908-13 (2002).
Sebba et al., "Tocilizumab: the first interleukin-6-receptor inhibitor," Am J Health Syst Pharm., Aug. 1, 2008;65(15):1413-8. doi: 10.2146/ajhp070449.
Sigma-Aldrich, "Product Information: Monoclonal Anti-Flag ® M1, Clone M1 produced in mouse, purified immunoglobulin," Sigma-Aldrich.com, Catalog No. F3040. Retrieved from the Internet on Nov. 5, 2013 at: http://www.sigmaaldrich.com/content/dam/sigma-aldrich/does/Sigma/Datasheet/f3040dat.pdf.
Stewart et al., "Site-directed mutagenesis of a catalytic antibody: an arginine and a histidine residue play key roles," Biochemistry, 33(8):1994-2003 (1994).
Tabrizi et al., "Elimination mechanisms of therapeutic monoclonal antibodies," Drug Discov Today, 11(1-2):81-8 (2006).
Takkinen et al., "Affinity and Specificity Maturation by CDR Walking," Antibody Engineering, Springer Lab Manuals, pp. 540-545 (2001).
Tsubaki et al., "C-terminal modification of monoclonal antibody drugs: amidated species as a general product-related substance," Int J Biol Macromol., 52:139-47. doi: 10.1016/j.ijbiomac.2012.09.016. Epub Sep. 25, 2012.
Vaughn et al., "Structural basis of pH-dependent antibody binding by the neonatal Fc receptor," Structure, 6(1):63-73 (1998).

(56) References Cited

OTHER PUBLICATIONS

Wojciak et al., "The crystal structure of sphingosine-1-phosphate in complex with a Fab fragment reveals metal bridging of an antibody and its antigen," Proc Natl Acad Sci U S A., 106(42):17717-22 (2009).
Yamamoto et al., "Molecular studies of pH-dependent ligand interactions with the low-density lipoprotein receptor," Biochemistry, 47(44):11647-52 (2008).
Zalevsky et al., "Enhanced antibody half-life improves in vivo activity," Nat. Biotechnol., 28(2):157-9 (2010).
Zhou et al., "Interfacial metal and antibody recognition," Proc Natl Acad Sci U S A., 102(41):14575-80 (2005).
Roopenian et al., "FcRn: the neonatal Fc receptor comes of age," Nat Rev Immunol., Sep. 2007;7(9):715-25. Epub Aug. 17, 2007.
Wally et al., "Identification of a novel substitution in the constant region of a gene coding for an amyloidogenic kappaI light chain," Biochim Biophys Acta., May 31, 1999;1454(1):49-56.
Nordlund et al., "Introduction of histidine residues into avidin subunit interfaces allows pH-dependent regulation of quaternary structure and biotin binding," FEBS Lett., Dec. 18, 2003;555(3):449-54.
Stearns et al., "The interaction of a Ca2+-dependent monoclonal antibody with the protein C activation peptide region. Evidence for obligatory Ca2+ binding to both antigen and antibody," J Biol Chem., Jan. 15, 1988;263(2):826-32.
Wang et al., "Antibody structure, instability, and formulation," J Pharm Sci., Jan. 2007;96(1):1-26.
Ward et al., "A calcium-binding monoclonal antibody that recognizes a non-calcium-binding epitope in the short consensus repeat units (SCRs) of complement C1r," Mol Immunol., Jan. 1992;29(1):83-93.
Yeung et al., "Engineering human IgG1 affinity to human neonatal Fc receptor: impact of affinity improvement on pharmacokinetics in primates," J Immunol., Jun. 15, 2009;182(12):7663-71. doi: 10.4049/jimmunol.0804182.
Chappel et al., "Identification of a secondary Fc gamma RI binding site within a genetically engineered human IgG antibody," J Biol Chem., Nov. 25, 1993;268(33):25124-31.
Chappel et al., "Identification of the Fc gamma receptor class I binding site in human IgG through the use of recombinant IgG1/IgG2 hybrid and point-mutated antibodies," Proc Natl Acad Sci U S A., Oct. 15, 1991;88(20):9036-40.
Reist et al., "Human IgG2 constant region enhances in vivo stability of anti-tenascin antibody 81C6 compared with its murine parent," Clin Cancer Res., Oct. 1998;4(10):2495-502.
Amersham Biosciences, "Antibody Purification Handbook," Edition 18-1037-46 [online], [retrieved on Nov. 5, 2015]. Retrieved from the Internet: http://www.promix.ru/manuf/ge/chrom/lit/Antibody_Purification.pdf.
GE Healthcare. Application note 28-9277-92 AA. "High-throughput screening of elution pH for monoclonal antibodies on MabSelect SuRe using PreDictor plates" [online], [retrieved on Nov. 5, 2015]. Retrieved from the Internet: https://www.gelifesciences.com/gehcls_images/GELS/Related%20Content/Files/1314787424814/litdoc28927792AA_20110831131840.pdf.
Araki et al., "Efficacy of the anti-IL-6 receptor antibody tocilizumab in neuromyelitis optica: a pilot study," Neurology, Apr. 15, 2014;82(15):1302-6.
Balint et al., "Antibody engineering by parsimonious mutagenesis," Gene., Dec. 27, 1993;137(1):109-18.
Barkhof et al., "Comparison of MRI criteria at first presentation to predict conversion to clinically definite multiple sclerosis," Brain, Nov. 1997;120 ( Pt 11):2059-69.
Batra et al., "Pharmacokinetics and biodistribution of genetically engineered antibodies," Curr Opin Biotechnol., Dec. 2002;13(6):603-8.
Chihara et al., "Interleukin 6 signaling promotes anti-aquaporin 4 autoantibody production from plasmablasts in neuromyelitis optica," Proc Natl Acad Sci U S A., Mar. 1, 2011;108(9):3701-6. doi: 10.1073/pnas.1017385108. Epub Feb. 14, 2011.
Chihara et al., "Autoantibody Producing Cells in Neuromyelitis Optica," Journal of Clinical and Experimental Medicine, 2012;240:534-5 (English translation).
Christensen et al., "Systemic inflammation in progressive multiple sclerosis involves follicular T-helper, Th17- and activated B-cells and correlates with progression," PLoS One, 2013;8(3):e57820.
Dall'Acqua et al., "Increasing the affinity of a human IgG1 for the neonatal Fc receptor: biological consequences," J. Immunol., Nov. 1, 2002;169(9):5171-80.
Hosokawa et al., "The Response to Treatment with Interferon beta-1b in Patients with Multiple Sclerosis," Shinkei Chiryo, 2008;25:589-95 (English translation).
Houzen et al., "Increased prevalence, incidence, and female predominance of multiple sclerosis in northern Japan," J Neurol Sci., Dec. 15, 2012;323(1-2):117-22.
Kakuron III, "Section 9 Opticospinal Multiple Sclerosis," Tahatsusei Kokasho Chiryo Guideline, 2010;2010:104-9 (English translation).
Lucchinetti et al., "Heterogeneity of multiple sclerosis lesions: implications for the pathogenesis of demyelination," Ann Neurol., Jun. 2000;47:707-17.
Miller et al., "Differential diagnosis of suspected multiple sclerosis: a consensus approach," Mult Scler., Nov. 2008;14(9):1157-74.
Nakamura et al., "IL-6-dependent Plasmablasts in Pathological Conditions of Relapsing-Remitting Multiple Sclerosis," Jap J Clin Immunol., 2013;36:345, W5-5 (English translation).
Nakamura et al., "Clinical Features of Multiple Sclerosis with High Plasmablast Frequency in Peripheral Blood," Poster Session, 54th Annual Meeting of the Japanese Society of Neurology, Tokyo, Japan, presented Jun. 1, 2013.
Nakamura et al., "Clinical Characteristics of Multiple Sclerosis with High Peripheral Blood Plasmablast Frequency," Meeting Abstract, 54th Annual Meeting of the Japanese Society of Neurology, Tokyo, Japan, published Apr. 30, 2013 (English translation).
Nakamura et al., "Clinical Features of Multiple Sclerosis with High Plasmablast Frequency in Peripheral Blood," Poster Session, Multiple Sclerosis, Keystone Symposia on Molecular and Cellular Biology, Big Sky, Montana, presented Jan. 14, 2013.
Nakamura et al., "Clinical Features of Multiple Sclerosis with High Plasmablast Frequency in Peripheral Blood," Abstract, Multiple Sclerosis, Keystone Symposia on Molecule and Cellular Biology, Big Sky, Montana, published online Dec. 11, 2012.
Nakamura et al., "Clinical Features of Multiple Sclerosis with High Plasmablast Frequency in Peripheral Blood," Abstract for Poster Session, Multiple Sclerosis, Keystone Symposia on Molecule and Cellular Biology, Big Sky, Montana, distributed Jan. 11, 2013.
Palladino et al., "Anti-TNF-alpha therapies: the next generation," Nat Rev Drug Discov., Sep. 2003;2(9):736-46.
Shimizu et al., "IFNβ-1b may severely exacerbate Japanese opticspinal MS in neuromyelitis optica spectrum," Neurology, Oct. 19, 2010;75(16):1423-7.
Smolen et al., "Interleukin-6: a new therapeutic target," Arthritis Res Ther., 2006;8 Suppl 2:S5. Epub Jul. 28, 2006.
Srivastava et al., "Potassium channel KIR4.1 as an immune target in multiple sclerosis," N Engl J Med., Jul. 12, 2012;367:115-23.
Tintoré et al., "Isolated demyelinating syndromes: comparison of different MR imaging criteria to predict conversion to clinically definite multiple sclerosis," AJNR Am J Neuroradiol., Apr. 2000;21(4):702-6.
Waubant et al., "Clinical characteristics of responders to interferon therapy for relapsing MS," Neurology, Jul. 22, 2003;61(2):184-9.
International Search Report for App. Ser. No. PCT/JP2014/065449, dated Sep. 22, 2014.
Adams et al., "Humanization of a recombinant monoclonal antibody to produce a therapeutic HER dimerization inhibitor, pertuzumab," Cancer Immunol. Immunother., 55:717-727 (2006).
Algonomics—Tripole® applications [online] [retrieved on Feb. 29, 2012]. Retrieved from the Internet: http://web.archive.org/web20090221052902/http://www.algonomics.com/proteinengineering/tripole_applications.php, 2 pages (Feb. 21, 2009).
Allen et al., "Interchain disulfide bonding in human IgG2 antibodies probed by site-directed mutagenesis," Biochemistry, 48(17):3755-66 (2009).

(56) References Cited

OTHER PUBLICATIONS

Almagro et al., "Humanization of antibodies," Front Biosci., 13:1619-33 (2008).
Amersham Biosciences, "Affinity Chromatography: Principles and Methods," Edition AD, pp. 16-18, 137 (2002).
Armour et al., "Recombinant human IgG molecules lacking Fcgamma receptor I binding and monocyte triggering activities," Eur. J. Immunol., 29(8):2613-24 (1999).
Bartelds et al., "Clinical response to adalimumab: relationship to anti-adalimumab antibodies and serum adalimumab concentrations in rheumatoid arthritis," Ann Rheum. Dis., 66(7):921-926 (2007).
Bayry et al., "Immuno affinity purification of foot and mouth disease virus type specific antibodies using recombinant protein adsorbed to polystyrene wells," J. Virol. Methods, 81:21-30 (1999).
Bender et al., "Immunogenicity, efficacy and adverse events of adalimumab in RA patients," Rheumatol. Int., 27(3):269-274 (2007).
Binz et al., "Engineering novel binding proteins from nonimmunoglobulin domains," Nat. Biotechnol., 23:1257-68 (2005).
Branden and Tooze, "Recognition of Foreign Molecules by the Immune System," Introduction to Protein Structure, 2d Ed., Garland Publishing, pp. 299-323 (1999).
Brown et al., "Tolerance of single, but not multiple, amino acid replacements in antibody $V_H$ CDR2: a means of minimizing B cell wastage from somatic hypermutation?," J. Immunol., 156(9):3285-91 (1996).
CALBIOCHEM® Buffers, "A guide for the preparation and use of buffers in biological systems," by Chandra Mohan, Ph.D., Copyright© 2003 EMD Biosciences, Inc., an Affiliate of Merck KGaA, Darmstadt, Germany, 37 pages.
Carter, "Bispecific human IgG by design," J. Immunol. Methods, 248:7-15 (2001).
Chau et al., "HuM291(Nuvion), a humanized Fc receptor-nonbinding antibody against CD3, anergizes peripheral blood T cells as partial agonist of the T cell receptor," Transplantation., 71(7):941-50 (2001).
Chen et al., "Generation and analysis of random point mutations in an antibody CDR2 sequence: many mutated antibodies lose their ability to bind antigen," J. Exp. Med., 176(3):855-66 (1992).
Chen et al., "Defective secretion of an immunoglobulin caused by mutations in the heavy chain complementarity determining region 2," J. Exp. Med., 180(2):577-86 (1994).
Chien et al., "Significant structural and functional change of an antigen-binding site by a distant amino acid substitution: proposal of a structural mechanism," Proc. Natl. Acad. Sci. U.S.A., 86(14):5532-6 (1989).
Chirino et al., "Minimizing the immunogenicity of protein therapeutics," Drug Discov. Today., 9:82-90 (2004).
Choy et al., "Inhibiting interleukin-6 in rheumatoid arthritis," Curr. Rheumatol. Rep., 10(5):413-7 (2008).
Chu et al., "Accumulation of succinimide in a recombinant monoclonal antibody in mildly acidic buffers under elevated temperatures," Pharm. Res., 24(6):1145-56 (2007).
Cole et al., "Human IgG2 variants of chimeric anti-CD3 are nonmitogenic to T cells," J. Immunol., 159(7):3613-21 (1997).
Comper and Glasgow, "Charge selectivity in kidney ultrafiltration," Kidney Int., 47:1242-51 (1995).
Cordoba et al., "Non-enzymatic hinge region fragmentation of antibodies in solution," J. Chromatogr. B. Analyt. Technol. Biomed. Life Sci., 818(2):115-21 (2005).
Couto et al., "Anti-BA46 Monoclonal Antibody Mc3: Humanization Using a Novel Positional Consensus and in Vivo and in Vitro Characterization," Cancer Research, 55:1717-1722 (1995).
Dall'Acqua et al., "Antibody humanization by framework shuffling," Methods, 36(1):43-60 (2005).
Dall'Acqua et al., "Modulation of the effector functions of a human IgG1 through engineering of its hinge region," J. Immunol., 177(2):1129-38 (2006).
Damschroder et al., "Framework shuffling of antibodies to reduce immunogenicity and manipulate functional and biophysical properties," Mol. Immunol., 44(11):3049-60 (2007).

Davies et al., "Affinity improvement of single antibody VH domains: residues in all three hypervariable regions affect antigen binding," Immunotechnology, 2(3):169-79 (1996).
Deen et al., "Structural determinants of glomerular permeability," Am. J. Physiol. Renal. Physiol., 281:F579-F596 (2001).
De Groot et al., "De-immunization of therapeutic proteins by T-cell epitope modification," Dev. Biol. (Basel), 122:171-94 (2005).
Del Rio et al., "An Engineered Penicillin Acylase with Altered Surface Charge Is More Stable in Alkaline pH," Ann. NY Acad. Sci., 799:61-64 (1996).
Deng et al., "An Agonist Murine Monoclonal Antibody to the Human c-Mp1 Receptor Stimulates Megakaryocytopoiesis," Blood, 92:1981-88 (1998).
De Pascalis et al., "Grafting of "abbreviated" complementarity-determining regions containing specificity-determining residues essential for ligand contact to engineer a less immunogenic humanized monoclonal antibody," J. Immunol., 169(6):3076-84 (2002).
Dillon et al., "Structural and functional characterization of disulfide isoforms of the human IgG2 subclass," J. Biol. Chem., 283(23):16206-15 (2008).
Elliott et al., "Activation of the erythropoietin (EPO) receptor by bivalent anti-EPO receptor antibodies," J. Biol. Chem., 271(40):24691-7 (1996).
Ewert et al., "Stability improvement of antibodies for extracellular and intracellular applications: CDR grafting to stable frameworks and structure-based framework engineering," Methods, 34:184-199 (2004).
Fujii, "Antibody affinity maturation by random mutagenesis," Methods Mol. Biol., 248:345-59 (2004).
Gerstner et al., "Sequence plasticity in the antigen-binding site of a therapeutic anti-HER2 antibody," J. Mol. Biol., 321(5):851-62 (2002).
Gessner et al., "The IgG Fc receptor family," Ann Hematol., 76(6):231-248 (1998).
Ghetie and Ward, "FcRn: the MHC class I-related receptor that is more than an IgG transporter," Immunol. Today, 18:592-598 (1997).
Ghetie et al., "Increasing the serum persistence of an IgG fragment by random mutagenesis," Nat. Biotechnol., 15:637-640 (1997).
Ghetie et al., "Multiple roles for the major histocompatibility complex class I-related receptor FcRn," Annu. Rev. Immunol., 18:739-766 (2000).
Gobburu et al., "Pharmacokinetics/dynamics of 5c8, a monoclonal antibody to CD154 (CD40 ligand) suppression of an immune response in monkeys," J. Pharmacol. Exp. Ther., 286:925-930 (1998).
Goode et al., "The glomerular basement membrane charge-selectivity barrier: an oversimplified concept?," Nephrol. Dial. Transplant., 11:1714-16 (1996).
Graves et al., "Molecular modeling and preclinical evaluation of the humanized NR-LU-13 antibody," Clin. Cancer Res., 5:899-908 (1999).
Guerne et al., "Synovium as a source of interleukin 6 in vitro. Contribution to local and systemic manifestations of arthritis," J. Clin. Invest., 83(2):585-92 (1989).
Gupta et al., "Affinity chromatography and co-chromatography of bispecific monoclonal antibody immunoconjugates," J. Biochem. Biophys. Methods, 51:203-216 (2002).
Guyre et al., "Increased potency of Fc-receptor-targeted antigens," Cancer Immunol Immunother., 45(3-4):146-8 (1997).
Hanes et al., "Picomolar affinity antibodies from a fully synthetic naive library selected and evolved by ribosome display," Nat. Biotechnol., 18(12):1287-1292 (2000).
Hanson et al., "Catalytic antibodies and their applications," Curr. Opin. Biotechnol., 16:631-636 (2005).
He et al., "Humanization and pharmacokinetics of a monoclonal antibody with specificity for both E- and P-selectin," J. Immunol., 160:1029-35 (1998).
Hinton et al., "An engineered human IgG1 antibody with longer serum half-life," J. Immunol., 176:346-356 (2006).
Hinton et al., "Engineered human IgG antibodies with longer serum half-lives in primates," J. Biol. Chem., 279(8):6213-6 (2004).

(56) References Cited

OTHER PUBLICATIONS

Hirano et al., "Excessive production of interleukin 6/B cell stimulatory factor-2 in rheumatoid arthritis," Eur. J. Immunol., 18(11):1797-801 (1988).
Holt et al., "Domain antibodies: proteins for therapy," Trends Biotechnol., 21(11):484-90 (2003).
Houssiau et al., "Interleukin-6 in synovial fluid and serum of patients with rheumatoid arthritis and other inflammatory arthritides," Arthritis Rheum., 31(6):784-8 (1988).
Hwang et al., "Use of human germline genes in a CDR homology-based approach to antibody humanization," Methods., 36:35-42 (2005).
Igawa et al., "Engineering the variable region of therapeutic IgG antibodies," MAbs, 3(3):243-52 (2011).
Igawa et al., "Reduced elimination of IgG antibodies by engineering the variable region," Protein Eng. Des. Sel., 23(5):385-92 (2010).
Igawa et al., "Antibody recycling by engineered pH-dependent antigen binding improves the duration of antigen neutralization," Nat. Biotechnol., 28(11):1203-7 (2010).
Ito et al., "The His-probe method: effects of histidine residues introduced into the complementarity-determining regions of antibodies on antigen-antibody interactions at different pH values," FEBS Lett., 309:85-88 (1992).
Johnson et al., "Cation exchange-HPLC and mass spectrometry reveal C-terminal amidation of an IgG1 heavy chain," Anal. Biochem., 360:75-83 (2007).
Jones et al., "Identification and removal of a promiscuous CD4+ T cell epitope from the C1 domain of factor VIII," Thromb. Haemost., 3:991-1000 (2005).
Kai et al., "Switching constant domains enhances agonist activities of antibodies to a thrombopoietin receptor," Nat. Biotechnol., 26(2):209-11 (2008).
Kashmiri et al., "Generation, characterization, and in vivo studies of humanized anticarcinoma antibody CC49," Hybridoma, 14:461-473 (1995).
Katayose et al., "MUC1-specific targeting immunotherapy with bispecific antibodies: inhibition of xenografted human bile duct carcinoma growth," Cancer Res., 56(18):4205-12 (1996).
Khawli et al., "Improved tumor localization and radioimaging with chemically modified monoclonal antibodies," Cancer Biother. Radiopharm., 11:203-215 (1996).
Kim et al., "Antibody engineering for the development of therapeutic antibodies," Mol. Cells, 20:17-29 (2005).
Kim et al., "Chemical modification to reduce renal uptake of disulfide-bonded variable region fragment of anti-tac monoclonal antibody labeled with 99mTc," Bioconjugate Chem., 10:447-453 (1999).
Kim et al., "Lowering of pI by acylation improves the renal uptake of 99mTc-labeled anti-Tac dsFv: effect of different acylating reagents," Nucl. Med. Biol., 29:795-801 (2002).
Kishimoto, "The biology of interleukin-6," Blood, 74(1):1-10 (1989).
Kobayashi et al., "The pharmacokinetic characteristics of glycolated humanized anti-Tac Fabs are determined by their isoelectric points," Cancer Res., 59:422-430 (1999).
Kobayashi et al., "A monoclonal antibody specific for a distinct region of hen egg-white lysozyme," Mol. Immunol., 19:619-30 (1982).
Komissarov et al., "Site-specific mutagenesis of a recombinant anti-single-stranded DNA Fab. Role of heavy chain complementarity-determining region 3 residues in antigen interaction," J. Biol. Chem., 272(43):26864-70 (1997).
Kotake et al., "Interleukin-6 and soluble interleukin-6 receptors in the synovial fluids from rheumatoid arthritis patients are responsible for osteoclast-like cell formation," J. Bone Miner Res., 11(1):88-95 (1996).
Kreutz et al., "Efficient bispecific monoclonal antibody purification using gradient thiophilic affinity chromatography," J. Chromatogr. B, 714:161-170 (1998).
Leong et al., "Adapting pharmacokinetic properties of a humanized anti-interleukin-8 antibody for therapeutic applications using site-specific pegylation," Cytokine, 16(3):106-19 (2001).
Lindhofer et al., "Preferential Species-Restricted Heavy/Light Chain Pairing in Rat/Mouse Quadromas," J. Immunol., 155:219-225 (1995).
Liu et al., "Heterogeneity of monoclonal antibodies," J. Pharm. Sci., 97(7):2426-47 (2008).
Lobo et al., "Antibody pharmacokinetics and pharmacodynamics," J. Pharm. Sci., 93:2645-68 (2004).
Lund et al., "Expression and characterization of truncated forms of humanized L243 IgG1. Architectural features can influence synthesis of its oligosaccharide chains and affect superoxide production triggered through human Fcgamma receptor I," Eur. J. Biochem., 267:7246-57 (2000).
MacCallum et al., "Antibody-antigen interactions: contact analysis and binding site topography," J. Mol. Biol., 262:732-45 (1996).
Madhok et al., "Serum interleukin 6 levels in rheumatoid arthritis: correlations with clinical and laboratory indices of disease activity," Ann. Rheum. Dis., 52(3):232-4 (1993).
Maeda et al., "pH-dependent receptor/ligand dissociation as a determining factor for intracellular sorting of ligands for epidermal growth factor receptors in rat hepatocytes," J. Control Release, 82(1):71-82 (2002).
Maini et al., "Double-blind randomized controlled clinical trial of the interleukin-6 receptor antagonist, tocilizumab, in European patients with rheumatoid arthritis who had an incomplete response to methotrexate," Arthritis Rheum., 54:2817-29 (2006).
Manzke et al., "Single-step purification of bispecific monoclonal antibodies for immunotherapeutic use by hydrophobic interaction chromatography," J. Immunol. Methods, 208:65-73 (1997).
Martin et al., "Crystal structure at 2.8 A of an FcRn/heterodimeric Fc complex: mechanism of pH-dependent binding," Mol. Cell, 7:867-877 (2001).
Martinez et al., "Disulfide connectivity of human immunoglobulin G2 structural isoforms," Biochemistry, 47(28):7496-7508 (2008).
Marvin et al., "Recombinant approaches to IgG-like bispecific antibodies," Acta. Pharmacol. Sin., 26:649-658 (2005).
Marvin et al., "Redesigning an antibody fragment for faster association with its antigen," Biochemistry, 42:7077-83 (2003).
Maxfield et al., "Endocytic recycling," Nat. Rev. Mol. Cell Biol., 5(2):121-32 (2004).
Maynard et al., "Antibody engineering," Annu. Rev. Biomed. Eng., 2:339-76 (2000).
Merchant et al., "An efficient route to human bispecific IgG," Nat. Biotechnol., 16:677-681 (1998).
Mihara et al., "Tocilizumab inhibits signal transduction mediated by both mIL-6R and sIL-6R, but not by the receptors of other members of IL-6 cytokine family," Int. Immunopharmacol., 5(12):1731-40 (2005).
Murtaugh et al., "A combinatorial histidine scanning library approach to engineer highly pH-dependent protein switches," Protein Sci., 20(9):1619-31 doi:10.1002/pro 696 (2011).
Nesterova et al., "Glypican-3 as a novel target for an antibody-drug conjugate," AACR Abstract No. 656, Los Angeles, CA (Apr. 4-18, 2007).
Nishimoto et al., "Humanized anti-interleukin-6 receptor antibody treatment of multicentric Castleman disease," Blood, 106:2627-32 (2005).
Nishimoto et al., "Clinical studies in patients with Castleman's disease, Crohn's disease, and rheumatoid arthritis in Japan," Clin. Rev. Allergy Immunol., 28(3):221-30 (2005).
Nishimoto et al., "Interleukin 6: from bench to bedside," Nat. Clin. Pract. Rheumatol., 2(11):619-26 (2006).
Nishimoto, Nihon Rinsho, 65(7):1218-26 (2007).
Nishimoto et al., "Humanized antihuman IL-6 receptor antibody, tocilizumab," Handb Exp Pharmacol., (181):151-60 (2008).
Nishimoto et al., "Anti-interleukin 6 receptor antibody treatment in rheumatic disease," Ann Rheum Dis., 59 Suppl 1:i21-7 (2000).
Ohno et al., "Antigen-binding specificities of antibodies are primarily determined by seven residues of VH," Proc. Natl. Acad. Sci. U.S.A., 82(9):2945-9 (1985).
Ohsugi et al., Pharm Stage, 7(5):13-18 (2007).

(56) References Cited

OTHER PUBLICATIONS

Onda et al., "Lowering the Isoelectric Point of the Fv Portion of Recombinant Immunotoxins Leads to Decreased Nonspecific Animal Toxicity without Affecting Antitumor Activity," Cancer Res., 61:5070-77 (2001).
Ono et al., "The humanized anti-HM1.24 antibody effectively kills multiple myeloma cells by human effector cell-mediated cytotoxicity," Mol. Immunol , 36(6):387-95 (1999).
Ozhegov et al., Tolkovyi Slovar Russkogo iazyka: 2004, p. 292.
Pardridge et al., "Enhanced endocytosis in cultured human breast carcinoma cells and in vivo biodistribution in rats of a humanized monoclonal antibody after cationization of the protein," J. Pharmacol. Exp. Ther., 286(1):548-54 (1998).
Pavlinkova et al., "Charge-modified single chain antibody constructs of monoclonal antibody CC49: Generation, characterization, pharmacokinetics, and biodistribution analysis," Nucl. Med. Biol., 26:27-34 (1999).
Pavlou et al., "The therapeutic antibodies market to 2008," Eur. J. Pharm. Biopharm., 59:389-396 (2005).
Pini et al., "Design and use of a phage display library. Human antibodies with subnanomolar affinity against a marker of angiogenesis eluted from a two-dimensional gel," J. Biol. Chem., 273(34):21769-76 (1998).
Poduslo et al., "Polyamine modification increases the permeability of proteins at the blood-nerve and blood-brain barriers," J. Neurochem., 66:1599-1609 (1996).
Pons et al., "Energetic analysis of an antigen/antibody interface: alanine scanning mutagenesis and double mutant cycles on the HyHEL-10/lysozyme interaction," Protein Sci., 8(5):958-68 (1999).
Presta, "Engineering of therapeutic antibodies to minimize immunogenicity and optimize function," Adv. Drug Deliv. Rev., 58(5-6):640-56.
Presta et al., "Molecular engineering and design of therapeutic antibodies," Curr. Opin. Immunol., 20(4):460-70. doi: 10.1016/j.coi.2008.06.012 (2008).
Rajpal et al., A general method for greatly improving the affinity of antibodies by using combinatorial libraries, Proc. Natl. Acad. Sci. USA, 102:8466-71 (2005).
Rathanaswami et al., "Demonstration of an in vivo generated sub-picomolar affinity fully human monoclonal antibody to interleukin-8," Biochem. Biophys. Res. Commun., 334:1004-13 (2005).
Reddy et al., "Elimination of Fc receptor-dependent effector functions of a modified IgG4 monoclonal antibody to human CD4," J. Immunol., 164(4):1925-33 (2000).
Reichert et al., "Monoclonal antibody successes in the clinic," Nat. Biotechnol., 23:1073-78 (2005).
Reichert et al., "Development trends for monoclonal antibody cancer therapeutics," Nat. Rev. Drug Discov., 6(5):349-56 (2007).
Rich et al., "Grading the commercial optical biosensor literature—Class of 2008: 'The Mighty Binders'," J. Mol. Recognit., 23(1):1-64 (2010). doi: 10.1002/jmr.1004.
Roitt et al., Immunology, M. Mir, p. 110 (2000).
Rothe et al., "Ribosome display for improved biotherapeutic molecules," Expert Opin. Biol. Ther., 6:177-187 (2006).
Rudikoff et al., "Single amino acid substitution altering antigen-binding specificity," Proc. Natl. Acad. Sci. U.S.A., 79(6):1979-83 (1982).
Sack et al., "Interleukin-6 in synovial fluid is closely associated with chronic synovitis in rheumatoid arthritis," Rheumatol. Int., 13(2):45-51 (1993).
Salfeld et al., "Isotype selection in antibody engineering," Nat. Biotechnol., 25:1369-72 (2007).
Sal-Man et al., "Arginine mutations within a transmembrane domain of Tar, an *Escherichia coli* aspartate receptor, can drive homodimer dissociation and heterodimer association in vivo," Biochem. J., 385:29-36 (2005).
Sato et al., "Reshaping a human antibody to inhibit the interleukin 6-dependent tumor cell growth," Cancer Res., 53:851-856 (1993).
Schaeffer et al., "The Rat Glomerular Filtration Barrier Does Not Show Negative Charge Selectivity," Microcirculation, 9:329-342 (2002).
Schmitz et al., "Phage display: a molecular tool for the generation of antibodies—a review," Placenta., 21 Suppl A:S106-12 (2000).
Segal et al., "Bispecific antibodies in cancer therapy," Curr. Opin. Immunol., 11:558-562 (1999).
Shaul, "Exploring the charge space of protein-protein association: a proteomic study," Proteins, 60:341-352 (2005).
Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem., 276:6591-6604 (2001) (Epub Nov. 28, 2000).
Shire et al., "Challenges in the development of high protein concentration formulations," J. Pharm. Sci., 93:1390-1402 (2004).
Strand et al., "Biologic therapies in rheumatology: lessons learned, future directions," Nat. Rev. Drug Discov., 6:75-92 (2007).
Sun et al., "Coexpression of Gas6/Axl in human ovarian cancers," Oncology, 66(6):450-7 (2004).
Tamura et al., "Soluble interleukin-6 receptor triggers osteoclast formation by interleukin 6," Proc. Natl. Acad. Sci. USA, 90(24):11924-8 (1993).
Tan et al., "Engineering the isoelectric point of a renal cell carcinoma targeting antibody greatly enhances scFv solubility," Immunotechnology, 4(2):107-114 (1998).
Tarditi et al., "Selective high-performance liquid chromatographic purification of bispecific monoclonal antibodies," J. Chromatogr., 599:13-20 (1992).
Teeling et al., "The biological activity of human CD20 monoclonal antibodies is linked to unique epitopes on CD20," J. Immunol , 177(1):362-71 (2006).
Ten Kate et al., "Effect of isoelectric point on biodistribution and inflammation: imaging with indium-1 1 1-labelled IgG," Eur. J. Nucl. Med., 17:305-309 (1990).
Tsuchiya, Credit Suisse Seminar, "Therapeutic Antibody," at Fuji-Gotemba Laboratories, p. 21 (2006).
Tsurushita et al., "Design of humanized antibodies: From anti-Tac to Zenapax," Methods, 36:69-83 (2005).
Vajdos et al., "Comprehensive functional maps of the antigen-binding site of an anti-ErbB2 antibody obtained with shotgun scanning mutagenesis," J. Mol. Biol., 320(2):415-28 (2002).
Vaisitti et al., "Cationization of monoclonal antibodies: another step towards the "magic bullet"?," J. Biol. Regul. Homeost. Agents., 19(3-4):105-12 (2005).
Van Walle et al., Immunogenicity screening in protein drug development, Expert Opin. Biol. Ther., 7(3):405-418 (2007).
Wang et al., "Polyethylene Glycol-modified Chimeric Toxin Composed of Transforming Growth Factor alpha and Pseudomonas Exotoxin," Cancer. Res., 53:4588-4594 (1993).
Wiens et al., "Somatic mutation in VH complementarity-determining region 2 and framework region 2: differential effects on antigen binding and Ig secretion," J. Immunol., 159(3):1293-302.
Wiens et al., "Mutation of a single conserved residue in VH complementarity-determining region 2 results in a severe Ig secretion defect," J. Immunol., 167(4):2179-86 (2001).
Wu et al., "Humanization of a murine monoclonal antibody by simultaneous optimization of framework and CDR residues," J. Mol. Biol., 294(1):151-62 (1999).
Wu et al., "Development of motavizumab, an ultra-potent antibody for the prevention of respiratory syncytial virus infection in the upper and lower respiratory tract," J. Mol. Biol., 368:652-665 (2007).
Wypych et al., "Human IgG2 antibodies display disulfide-mediated structural isoforms," J. Biol. Chem., 283(23):16194-16205 (2008).
Xiang et al., "Study of B72.3 combining sites by molecular modeling and site-directed mutagenesis," Protein Eng., 13(5):339-44 (2000).
Yamasaki et al., "Pharmacokinetic analysis of in vivo disposition of succinylated proteins targeted to liver nonparenchymal cells via scavenger receptors: importance of molecular size and negative charge density for in vivo recognition by receptors," J. Pharmacol. Exp. Ther., 301:467-477 (2002).

(56) References Cited

OTHER PUBLICATIONS

Yang et al., "Tailoring structure-function and pharmacokinetic properties of single-chain Fv proteins by site-specific PEGylation," Protein Eng., 16:761-770 (2003).
Yang et al., "CDR walking mutagenesis for the affinity maturation of a potent human anti-HIV-1 antibody into the picomolar range," J. Mol. Biol., 254(3):392-403 (1995).
Yokota et al., "Clinical study of tocilizumab in children with systemic-onset juvenile idiopathic arthritis," Clin. Rev. Allergy Immunol., 28(3):231-8 (2005).
Zhu et al., "MHC class I-related neonatal Fc receptor for IgG is functionally expressed in monocytes, intestinal macrophages, and dendritic cells," J. Immunol., 166(5):3266-76 (2001).
Zuckier et al., "Chimeric human-mouse IgG antibodies with shuffled constant region exons demonstrate that multiple domains contribute to in vivo half-life," Cancer Res., 58:3905-08 (1998).
Zwick et al., "The long third complementarity-determining region of the heavy chain is important in the activity of the broadly neutralizing anti-human immunodeficiency virus type 1 antibody 2F5," J. Virol., 78(6):3155-61 (2004).
International Search Report for App. Ser. No. PCT/JP2009/066590, dated Oct. 20, 2009, 2 pages.
International Preliminary Report on Patentability for App. Ser. No. PCT/JP2009/066590, dated May 10, 2011, 6 pages.
International Preliminary Report on Patentability for PCT App. Ser. No. PCT/JP2008/067499, dated Apr. 7, 2010, 6 pages.
International Search Report for App. Ser. No. PCT/JP2008/067534, dated Oct. 21, 2008, 4 pages.
International Preliminary Report on Patentability for App. Ser. No. PCT/JP2008/067534, dated Apr. 7, 2010, 7 pages.
International Search Report for App. Ser. No. PCT/JP2009/057309, dated Jul. 7, 2009, 8 pages.
International Preliminary Report on Patentability for App. Ser. No. PCT/JP2009/057309, dated Nov. 30, 2010, 7 pages.
European Search Report for App. Ser. No. EP 09 72 9337, dated Nov. 3, 2011, 3 pages.
International Preliminary Report on Patentability for App. Ser. No. PCT/JP2007/057036, dated Oct. 21, 2008, 6 pages.
International Search Report for App. Ser. No. PCT/JP2007/057036, dated May 1, 2007, 2 pages.
European Search Report for App. Ser. No. 07 74 0494, dated Sep. 3, 2009, 3 pages.
International Preliminary Report on Patentability for App. Ser. No. PCT/JP2007/057058, dated Oct. 21, 2008, 11 pages.
International Search Report App. Ser. No. PCT/JP2007/057058, dated May 7, 2001, 2 pages.
European Search Report for App. Ser. No. 07 74 0474, dated Mar. 16, 2009, 5 pages.
International Search Report for App. Ser. No. PCT/JP2011/077619, dated Feb. 28, 2012, 4 pages.
International Preliminary Report on Patentability for App. Ser. No. PCT/JP2011/077619, dated Jun. 4, 2013, 8 pages.
Ejima et al., "Effective elution of antibodies by arginine and arginine derivatives in affinity column chromatography," *Anal Biochem.*, Oct. 15, 2005;345(2):250-7.
Montero-Julian et al., "Pharmacokinetic study of anti-interleukin-6 (IL-6) therapy with monoclonal antibodies: enhancement of IL-6 clearance by cocktails of anti-IL-6 antibodies," *Blood*, Feb. 15, 1995;85(4):917-24.
Rojas et al., "Formation, distribution, and elimination of infliximab and anti-infliximab immune complexes in cynomolgus monkeys," *J Pharmacol Exp Ther.*, May 2005;313(2):578-85. Epub Jan. 12, 2005.
U.S. Appl. No. 15/263,617, filed Sep. 13, 2016, Igawa et al.
Bian et al., "Discovery of promiscuous HLA-II-restricted T cell epitopes with Tepitope," *Methods*, Dec. 2004;34(4):468-75.
Cuatrecasas et al., "Affinity Chromatography," *Methods Enzymol.*, 1971;12:345-78.
Dhiman et al., "Gene expression microarrays: a 21st century tool for directed vaccine design," *Vaccine*, Oct. 12, 2001;20(1-2):22-30.

Durkee et al., "Immunoaffinity chromatographic purification of Russell's viper venom factor X activator using elution in high concentrations of magnesium chloride," *Protein Expr Purif.*, Oct. 1993;4(5):405-11.
Schroter et al., "A generic approach to engineer antibody pH-switches using combinatorial histidine scanning libraries and yeast display," *MAbs.*, 2015;7(1):138-51. doi: 10.4161/19420862.2014. 985993.
Thies et al., "The alternatively folded state of the antibody C(H)3 domain," *J Mol Biol.*, Jun. 22, 2001;309(5):1077-85.
Wikipedia, "Chaotropic agent" [online], [retrieved on Nov. 2, 2015]. Retrieved from the Internet: https://en.wikipedia.org/wiki/Chaotropic_agent.
USPTO Non-Final Office Action in U.S. Appl. No. 12/680,087, dated Oct. 27, 2011, 6 pages.
Brenner et al., "Errors in genome annotation," *Trends in Genetics*, Apr. 1999;15:132-133.
Brown et al., "A study of the interactions between an IgG-binding domain based on the B domain of staphylococcal protein A and rabbit IgG," *Mol Biotechnol.*, Aug. 1998;10(1):9-16.
Burmeister et al., "Crystal structure of the complex of rat neonatal Fc receptor with Fc," *Nature*, Nov. 24, 1994;372(6504):379-83.
Chen et al., "Selection and analysis of an optimized anti-VEGF antibody: crystal structure of an affinity-matured Fab in complex with antigen," *J Mol Biol.*, Nov. 5, 1999;293(4):865-81.
Coloma et al., "Position effects of variable region carbohydrate on the affinity and in vivo behavior of an anti-(1→6) dextran antibody," *J Immunol.*, Feb. 15, 1999;162(4):2162-70.
Declaration of Nimish Gera, Ph.D., CV and Exhibits, dated Sep. 1, 2016, 24 pages.
Ejima et al, "Effects of Acid Exposure on the Conformation, Stability, and Aggregation of Monoclonal Antibodies," Proteins. Mar. 1, 2007;66(4):954-62.
Gen Bank Accession No. AAG00910.2, "recombinant IgG2 heavy chain, partial [*Homo sapiens*]," May 14, 2001, 1 page.
Hird et al., "Tumour localisation with a radioactively labelled reshaped human monoclonal antibody," *Br J Cancer*, Nov. 1991;64(5):911-4.
Hironiwa et al., "Calcium-dependent antigen binding as a novel modality for antibody recycling by endosomal antigen dissociation," *MAbs*. Jan. 2016;8(1):65-73. doi: 10.1080/19420862.2015. 1110660. Epub Oct. 23, 2015.
Hong et al., "Enhanced cellular uptake and transport of polyclonal immunoglobulin G and fab after their cationization," *J Drug Target*, 2000;8(2):67-77.
Junghans et al., "The protection receptor for IgG catabolism is the beta2-microglobulin-containing neonatal intestinal transport receptor," *Proc Natl Acad Sci U S A.*, May 28, 1996;93(11):5512-6.
Laitinen et al., "Brave new (strept)avidins in biotechnology," *Trends Biotechnol.*, Jun. 2007;25(6):269-77. Epub Apr. 12, 2007.
Li et al., "Construction and characterization of a humanized anti-human CD3 monoclonal antibody 12F6 with effective immunoregulation functions," *Immunology*, Dec. 2005;116(4):487-98.
Linder et al., "Design of a pH-dependent cellulose binding domain," *FEBS Lett.*, Mar. 19, 1999;447(1):13-6.
Maier et al., "Assessment of fully automated antibody homology modeling protocols in molecular operating environment" *Proteins*. Aug. 2014;82(8):1599-610. doi: 10.1002/prot.24576. Epub Apr. 23, 2014.
Marshall et al., "Rational design and engineering of therapeutic proteins," *Drug Discov Today.*, Mar. 1, 2003;8(5):212-21.
Nakamura, et al., "Plasmablast in the pathology of multiple sclerosis," *Jpn. J. Clin. Immunol.*, 2015;38(5):403-11. doi: 10.2177/jsci. 38.403 (English abstract).
Newman et al, "Modification of the Fc Region of a Primatized IgG Antibody to Human CD4 Retains Its Ability to Modulate CD4 Receptors but Does Not Deplete CD4 T Cells in Chimpanzees," Clin Immunol. Feb. 2001;98(2):164-74.
Pardridge et al., "Enhanced cellular uptake and in vivo biodistribution of a monoclonal antibody following cationization," *J Pharm Sci.*, Aug. 1995;84(8):943-8.
Reimann et al., "A humanized form of a CD4-specific monoclonal antibody exhibits decreased antigenicity and prolonged plasma

(56) References Cited

OTHER PUBLICATIONS half-life in rhesus monkeys while retaining its unique biological and antiviral properties," *AIDS Res Hum Retroviruses*, Jul. 20, 1997;13(11):933-43.
Sarkar et al., "Rational cytokine design for increased lifetime and enhanced potency using pH-activated "histidine switching"," *Nat Biotechnol.*, Sep. 2002;20(9):908-13. Epub Aug. 5, 2002.
Schroeder et al., "Similarity and divergence in the development and expression of the mouse and human antibody repertoires," *Dev Comp Immunol.*, 2006;30(1-2):119-35.
Sharifi et al., "Improving monoclonal antibody pharmacokinetics via chemical modification," *Q J Nucl Med.*, Dec. 1998;42(4):242-9.
Smith et al., "The challenges of genome sequence annotation or 'the devil is in the details'," Nature *Biotechnology*, Nov. 1997;15:1222-1223.
Verhoeyen et al., "Construction of a reshaped HMFG1 antibody and comparison of its fine specificity with that of the parent mouse antibody," *Immunology*, Mar. 1993;78(3):364-70.
Verhoeyen et al., "Monoclonal Antibodies in Clinical Oncology," 1991, Edited by AA Epenetos, Chapter 5, pp. 37-43, Chapman and Hall.
U.S. Appl. No. 15/614,842, filed Jun. 6, 2017, Igawa et al.
U.S. Appl. No. 15/725,692, filed Oct. 5, 2017, Igawa et al.
Annual Report 2012, "Integrated Edition Including CSR Report" Chugai Pharmaceutical Co., Ltd., Mar. 27, 2013, 154 pages.
Akira et al., "Interleukin-6 in Biology and Medicine," Adv. Immunol., Dec. 31, 1993; 54:1-78.
Aricha et al., "Blocking of IL-6 suppresses experimental autoimmune myasthenia gravis," J. Autoimmun., Mar. 2011; 36(2):135-41. doi:10.1016/j.jaut2010.12.001. Epub Dec. 30, 2010.
Araki et al., "Clinical improvement in a patient with neuromyelitis optica following therapy with the anti-IL-6 receptor monoclonal antibody tocilizumab," Mod. Rheumatol., Jul. 2013; 23(4):827-31. doi: 10.1007/s10165-012-0715-9. Epub Jul. 11, 2012.
Diaz et al., "Effects of engineering charged amino acids in the CH3 domains on antibody heavy chain dimerization," Philippine Science Letters, 2011;4(1):48-55.
Fiedler et al., "An engineered IN-1 Fab fragment with improved affinity for the Nogo-A axonal growth inhibitor permits immunochemical detection and shows enhanced neutralizing activity," Protein Eng., Nov. 2002:15(11):931-41.
Foote et al., "Antibody framework residues affecting the conformation of the hypervariable loops," J. Mol. Biol., Mar. 20, 1992;224(2):487-99.
Gera et al., "Design of pH Sensitive Binding Proteins from the Hyperthermophilic Sso7d Scaffold," PLoS One, 2012;7(11):e48928. doi:10.1371/journal.pone.0048928. Epub Nov. 7, 2012.
Glick et al., Molecular Biotechnology: Principles and Applications of Recombinant DNA, 3rd Edition, Chemical Industry Press, Mar. 2003, p. 168 (with English translation).
Hamers-Casterman et al., "Naturally occurring antibodies devoid of light chains," Nature, Jun. 3, 1993;363(6428):446-8.
Hirano et al., "Complementary DNA for a novel human interleukin (BSF-2) that induces B lymphocytes to produce immunoglobulin," Nature, 324:73-76 (Nov. 1986).
Hirata et al., "Characterization of IL-6 Receptor Expression by Monoclonal and Polyclonal Antibodies," J. Immunol., Nov. 1, 1989;143(9):2900-6.
Hoogenboom, "Selecting and screening recombinant antibody libraries," Nat. Biotechnol., Sep. 2005; 23(9):1105-16.
Huang et al., "A Monoclonal Anti-Human IL-6 Receptor Antibody Inhibits the Proliferation of Human Myeloma Cells," Hybridoma., Oct. 1993:12(5):621-30.
Janeway et al., Immunobiology, 5th edition. Jun. 2001: Extract from Chapter 3, pp. 93-122.
Janeway et al., Immunobiology, 5th edition. Jun. 2001: Extract from Chapter 4, pp. 123-154.
Japanese Society of Neurological Therapeutics, Standard Neurological Therapeutics: Neuromyelitis Optica (NMO), 2013, vol. 30, No. 6, p. 777-794 *partial English translation is attached.

Kabat et al., Sequences of Proteins of Immunological Interest, National Institute of Health, Publication No. 91-3242, vol. 1 p. 647-60 (5th ed. 1991).
Knappik et al., "Fully Synthetic Human Combinatorial Antibody Libraries (HuCAL) Based on Modular Consensus Frameworks and CDRs Randomized with Trinucleotides," J. Mol. Biol., Feb. 11, 2000;296(1):57-86.
Krieckaert et al., "Immunogenicity of biologic therapies—we need tolerance," Nat. Rev. Rheumatol., Oct. 2010;6(10):558-9. doi:10.1038/nrrheum.
Kuroda et al., "Computer-aided antibody design," Protein Eng. Des. Sel., Oct. 2012;25(10):507-21. Epub Jun. 2, 2012.
Lotz et al., "B Cell Stimulating Factor 2/Interleukin 6 is a Costimulant for Human Thymocytes and T Lymphocytes," J. Exp. Med., Mar. 1, 1988;167(3):1253-1258.
Muller et al., "VEGF and the Fab fragment of a humanized neutralizing antibody: crystal structure of the complex at 2.4 Å resolution and mutational analysis of the interface," Structure, Sep. 6, 1998;(9):1153-67.
Murata et al., "Anti-Digoxin Fab Variants Generated by Phage Display," Mol. Biotechnol., Jun. 2013:54(2):269-77. doi:10.1007/s12033-012-9564-1.
Novick et al., "Monoclonal Antibodies to the Soluble Human IL-6 Receptor: Affinity Purification, ELISA, and Inhibition of Ligand Binding," Hybridoma., Feb. 1991;10(1):137-46.
Ober et al., "Visualizing the Site and Dynamics of IgG Salvage by the MHC Class I-Related Receptor, FcRn," J. Immunol., Feb. 15, 2004;172(4):2021-9.
Okabe, Proprietary Innovative Antibody Engineering Technologies in Chugai Pharmaceutical: Dec. 18, 2012, 78 pages.
Osbourn et al., "Generation of a panel of related human scFv antibodies with high affinities for human CEA," Immunotechnology, Sep. 1996:2(3):181-96.
Pancook et al., "In Vitro Affinity Maturation of Human IgM Antibodies Reactive with Tumor-Associated Antigens," Hybrid Hybridomics, Oct. 2001:20(5-6):383-96.
Pejchal et al., "A Conformational Switch in Human Immunodeficiency Virus gp41 Revealed by the Structures of Overlapping Epitopes Recognized by Neutralizing Antibodies," J. Virol., Sep. 2009; 83(17):8451-62. doi:10.1128/JVI.00685-09. Epub Jun. 10, 2009.
Polman et al., "Diagnostic Criteria for Multiple Sclerosis: 2010 Revisions to the McDonald Criteria," Ann. Neurol., Feb. 2011; 69(2):292-302. doi:10.1002/ana.22366.
Raposo et al., "Epitope-specific antibody response is controlled by immunoglobulin Vh polymorphisms," J. Exp. Med., Mar. 10, 2014:211(3):405-11. doi:10.1084/jem.20130968. Epub Feb. 17, 2014.
Reichert, "Antibodies to watch in 2014," mAbs, 6(4):799-802 (Jul./Aug. 2014).
Schier et al., "Isolation of Picomolar Affinity Anti-c-erbB-2 Single-chain Fv by Molecular Evolution of the Complementarity Determining Regions in the Center of the Antibody Binding Site," J. Mol. Biol., Nov. 8, 1996:263(4):551-67.
Singer et al., Genes & Genomes, 1991;67-69.
Spiess et al., "Bispecific antibodies with natural architecture produced by co-culture of bacteria expressing two distinct half-antibodies," Nat. Biotechnol., Aug. 1, 2013;31(8):753-8. doi:10.1038/nbt.2621. Epub Jul. 7, 2013.
Taga et al., "Receptors for B Cell Stimulatory Factor 2," J. Exp. Med., Oct. 1, 1987;166(4):967-981.
Taga et al., "Interleukin-6 Triggers the Association of Its Receptor with a Possible Signal Transducer, gp130," Cell, Aug. 11, 1989;58(3):873-581.
Wingerchuk et al., "Revised diagnostic criteria for neuromyelitis optica," Neurology, May 23, 2006;66(10):1485-9.
Wingerchuk et al., "International consensus diagnostic criteria for neuromyelitis optica spectrum disorders," Neurology, Jul. 14, 2015;85(2):177-89. doi:10.1212/WNL.0000000000001729. Epub Jun. 19, 2015.
Wu et al., "Stepwise in vitro affinity maturation of Vitaxin, an αvβ33-specific humanized mAb," Proc. Natl. Acad. Sci. USA, May 26, 1998; 95(11):6037-42.

(56) References Cited

OTHER PUBLICATIONS

Yamasaki et al., "Cloning and Expression of the Human Interleukin-6 (BSF-2/IFNβ 2) Receptor," Science, Aug. 12, 1988:241(4867):825-8.
Canfield et al., "The Binding Affinity of Human IgG for its High Affinity Fc Receptor Is Determined by Multiple Amino Acids in the $C_H2$ Domain and Is Modulated by the Hinge Region," J Exp Med, Jun. 1, 1991, 173(6):1483-91.
Yarilin, Fundamentals of Immunology M:Medicina, 1999, pp. 172-174 (with English translation), 8 pages.
U.S. Appl. No. 15/553,609, filed Aug. 25, 2017, Kakehi et al.
U.S. Appl. No. 15/575,027, filed Nov. 17, 2017, Yamamura et al.
U.S. Appl. No. 15/988,348, filed May 24, 2018, Igawa et al.
Balint et al., "Alterations of the peripheral B cell compartment in pediatric-onset multiple sclerosis," Journal of Neurology, May 2011, vol. 258, Suppl 1, pp. S202, Abstract No. P732.
Besada et al., "Potential patient benefit of a subcutaneous formulation of a tocilizumab for the treatment of rheumatoid arthritis: a critical review," Patient Preference and Adherence, Aug. 1, 2014, 8:1051-9. doi: 10.2147/PPA. S34958. eCollection 2014.
Cocco et al., "In Vitro Generation of Long-lived Human Plasma Cells," J. Immunol., Dec. 15, 2012 189(12):5773-85. doi:10.4049/jimmunol.1103720. Epub Nov. 16, 2012.
Dall'Acqua et al., "Properties of Human IgG1s Engineered for Enhanced Binding to the Neonatal Fc Receptor (FcRn)", J Biol Chem., Aug. 18, 2006, 281(33):23514-24. Epub Jun. 21, 2006.
EPO Register Extract EP 1915397 (document submitted in EP opposition and posted by EPO on Feb. 2, 2018), 4 pages.
Geneseq Accession No. AEM45140, Feb. 22, 2007, "Light chain constant region of therapeutic human IgG antibody".
Hotzel et al., "A strategy for risk mitigation of antibodies with fast clearance," mAbs., Nov.-Dec. 2012, 4(6):753-60. doi: 10.4161/mabs.22189.
Huizinga et al., "Sarilumab, a fully human monoclonal antibody against IL-6Rα in patients with rheumatoid arthritis and an inadequate response to methotrexate: efficacy and safety results from the randomised SARIL-RA-MOBILITY Part A trial," Ann Rheum Dis., Sep. 2014, 73(9):1626-34. doi:10. 1136/annrheumdis-2013-204405. Epub Dec. 2, 2013.
Jego et al., "Interleukin-6 is a growth factor for nonmalignant human plasmablasts," Blood, Mar. 15, 2001, 97(6):1817-22.
Jourdan et al., "An in vitro model of differentiation of memory B cells into plasmablasts and plasma cells including detailed phenotypic and molecular characterization," Blood, Dec. 10, 2009, 114(25):5173-81. doi:10.1182/blood-2009-07-235960.
Matsumoto et al., "Interleukin-10-Producing Plasmablasts Exert Regulatory Function in Autoimmune Inflammation," Immunity, Dec. 18, 2014, 41(6):1040-51.doi:10.1016/j.immuni.2014.10.016. Epub Nov. 4, 2014.
Okiyama et al., "Therapeutic Effects of Interleukin-6 Blockade in a Murine Model of Polymyositis That Does Not Require Interleukin-17A," Arthritis & Rheumatism, Aug. 2009, 60(8):2505-2512.
Ryman et al., "Pharmacokinetics of Monoclonal Antibodies," CPT Pharmacometrics Syst Pharmacol., Sep. 2017, 6(9):576-588. doi: 10.1002/psp4.12224. Epub Jul. 29, 2017.
Summary of information about antibodies in Examples of patent EP 2006381 (document submitted in EP opposition and posted by EPO on Apr. 13, 2018), 3 pages.
Written Submissions by Opponent 1 (Alexion Pharmaceuticals, Inc.) in Opposition of EP 2006381 dated Apr. 13, 2018, 19 pages.
Written Submissions by Opponent 2 (Novo Nordisk A/S) in Opposition of EP 2006381 dated Apr. 13, 2018, 14 pages.
Written Submissions by Opponent 3 (name Unknown) in Opposition of EP 2006381 dated Apr. 13, 2018, 16 pages.
Wu et al., "Ultra-potent Antibodies Against Respiratory Syncytial Virus: Effects of Binding Kinetics and Binding Valence on Viral Neutralization," J Mol Biol., Jul. 1, 2005, 350(1):126-44.
Yarilin, Fundamentals of Immunology M:Medicina, 1999, p. 169-72, 354-8 (with English translation) 21 pages.

International Search Report in International Application No. PCT/JP2016/064818, dated Aug. 16, 2016, 5 pages (with English translation).
International Preliminary Report on Patentability in International Application No. PCT/JP2016/064818, dated Nov. 30, 2017, 6 pages.
U.S. Appl. No. 14/741,786, Igawa et al., filed Jun. 17, 2015.
U.S. Appl. No. 12/680,082, Igawa et al., filed Jun. 25, 2010.
U.S. Appl. No. 12/680,112, Igawa et al., filed Jun. 23, 2010 (abandoned).
U.S. Appl. No. 13/959,489, Igawa et al., filed Aug. 5, 2013.
U.S. Appl. No. 15/263,617, Igawa et al., filed Sep. 13, 2016.
U.S. Appl. No. 13/889,484, Igawa et al., filed May 8, 2013.
U.S. Appl. No. 13/889,512, Igawa et al., filed May 8, 2013.
U.S. Appl. No. 14/962,293, Igawa et al., filed Dec. 8, 2015.
U.S. Appl. No. 13/990,158, Igawa et al., filed May 29, 2013.
U.S. Appl. No. 13/990,158, Igawa et al., filed Mar. 28, 2014.
U.S. Appl. No. 15/553,609, Kakehi et al., filed Aug. 25, 2017.
U.S. Appl. No. 15/575,027, Yamamura et al., filed Nov. 17, 2017.
U.S. Appl. No. 15/988,348, Igawa et al., filed May 24, 2018.
U.S. Appl. No. 13/524,528, Igawa et al., filed Jun. 15, 2012 (abandoned).
U.S. Appl. No. 15/614,842, Igawa et al., filed Jun. 6, 2017.
U.S. Appl. No. 12/680,112, Igawa et al., filed Jun. 23, 2010.
U.S. Appl. No. 13/959,489, Igawa et al., filed Aug. 5, 2013 (abandoned).
U.S. Appl. No. 15/263,617, Igawa et al., filed Sep. 13, 2016 (abandoned).
U.S. Appl. No. 16/041,976, Igawa et al., filed Jul. 23, 2018.
U.S. Appl. No. 13/257,145, Igawa et al., filed Nov. 22, 2011 (abandoned).
U.S. Appl. No. 14/680,250, Igawa et al., filed Apr. 7, 2015.
U.S. Appl. No. 12/936,587, Igawa et al., filed Jan. 3, 2011 (abandoned).
U.S. Appl. No. 13/595,139, Igawa et al., filed Aug. 27, 2012.
U.S. Appl. No. 12/295,039, Igawa et al., filed Jan. 20, 2009.
U.S. Appl. No. 15/725,692, Igawa et al., filed Oct. 5, 2017.
U.S. Appl. No. 13/990,158, Igawa et al., filed Mar. 28, 2014 (abandoned).
U.S. Appl. No. 14/897,498, Yamura et al., filed Dec. 10, 2015.
U.S. Appl. No. 15/952,945, Igawa et al., filed Apr. 13, 2018.
U.S. Appl. No. 952,951, Igawa et al., filed Apr. 13, 2018.
Antibodies from www.bioinf.org.uk: Dr. Andrew C.R. Martin's Group, downloaded Jul. 11, 2018, nine pages.
Cruse et al., Atlas of Immunology, CRC Press LLC, 2004, excerpt from Chapter 3 "Antigens and Immunogens", p. 109.
Decision of the Opposition Division for EP 2 006 381 on Jul. 25, 2018.
GE Healthcare, Biacore, Sensor Surface Handbook BR-1005-71, Edition AB, Feb. 2005, pp. 1-100.
Geneseq Accession No. ARZ17615, Aug. 21, 2008, "Human antibody IgG2 heavy chain constant region SEQ ID No. 36".
Janeway et al., Immunobiology, Chapter 3 "Structure of the Antibody Molecule and Immunoglobulin Genes," 3rd edition, Garland Press, 1997, p. 3:1-3:11.
King, "Applications and Engineering of Monoclonal Antibodies," Taylor & Francis, ISBN 0-203-21169-3, 2005, pp. 1-236.
Mellman, "The importance of being acid: the role of acidification in intracellular membrane traffic," J Exp Biol, Nov. 1992, 172, 39-45.
Petkova et al., "Enhanced half-life of genetically engineered human IgG1 antibodies in a humanized FcRn mouse model: potential application in humorally mediated autoimmune disease," Int Immunol, Dec. 18, 2006(12):1759-69. Epub Oct. 31, 2006.
Sequence alignments and modification scheme (document filed during Oral Proceedings in EPO opposition for EP 2 006 381 and mentioned in minutes of the Oral Proceedings posted by EPO on Jul. 25, 2018); 3 pages.
Vaccaro et al., "Divergent activities of an engineered antibody in murine and human systems have implications for therapeutics antibodies," Proc Natl Acad Sci USA, Dec. 5, 2006, 103(49):18709-14. Epub Nov. 20, 2006.
Van Den Abbeele et al., "Antigen-Binding Site Protection During Radiolabeling Leads to a Higher Immunoreactive Fraction," J Nucl Med, Jan. 1991 32(1):116-22.

(56) References Cited

OTHER PUBLICATIONS

USPTO Notice of Allowance in U.S. Appl. No. 12/680,087, dated Feb. 24, 2012, 5 pages.
USPTO Notice of Allowance in U.S. Appl. No. 12/680,087, dated Jun. 25, 2012, 11 pages.
USPTO Notice of Allowance in U.S. Appl. No. 12/680,087, dated Nov. 26, 2012, 7 pages.
USPTO Notice of Allowance in U.S. Appl. No. 12/680,087, dated Apr. 15, 2013, 9 pages.
USPTO Notice of Allowance in U.S. Appl. No. 12/680,087, dated Aug. 2, 2013, 8 pages.
USPTO Restriction Requirement in U.S. Appl. No. 15/263,617, dated Aug. 31, 2017, 8 pages.
USPTO Non-Final Office Action in U.S. Appl. No. 15/263,617, dated Feb. 23, 2018, 9 pages.
USPTO Restriction Requirement in U.S. Appl. No. 13/637,415, dated Dec. 31, 2014, 8 pages.
USPTO Restriction Requirement in U.S. Appl. No. 13/637,415, dated Dec. 1, 2016, 8 pages.
USPTO Non-Final Office Action in U.S. Appl. No. 13/637,415, dated May 13, 2015, 24 pages.
USPTO Final Office Action in U.S. Appl. No. 13/637,415, dated Nov. 13, 2015, 20 pages.
USPTO Non-Final Office Action in U.S. Appl. No. 13/637,415, dated May 23, 2017, 27 pages.
USPTO Final Office Action in U.S. Appl. No. 13/637,415, dated Mar. 2, 2018, 36 pages.
USPTO Non-Final Office Action in U.S. Appl. No. 15/495,026, dated Dec. 29, 2017, 22 pages.
USPTO Final Office Action in U.S. Appl. No. 15/495,026, dated Jul. 19, 2018, 37 pages.
U.S. Appl. No. 16/298,032, Igawa et al., filed Mar. 11 ,2019.
Aboud-Pirak et al., "Binding and Endocytosis of a Monoclonal Antibody to a High Molecular Weight Human Milk Fat Globule Membrane-associated Antigen by Cultured MCT-7 Breast Carcinoma Cells," Cancer Res, Jun. 1, 1988 48(11):3188-96.
Actemra (tocilizumab), Highlights of Prescribing Information, as revised in Aug. 2017 (1 page).
Anchin et al., "Recognition of Superpotent Sweetener Ligands by a Library of Monoclonal Antibodies," J Mol Recognit, Sep.-Oct. 1997, 10(5):235-42.
Ando et al., "Tocilizumab, a Proposed Therapy for the Cachexia of Interleukin6-Expressing Lung Cancer," PLOS One, Jul. 10, 2014 9(7):e102436. doi: 10.1371/journal.pone.0102436. eCollection 2014.
Barrabes et al., "Effect of sialic acid content on glycoprotein p*I* analyzed by two-dimensional electrophoresis," Electrophoresis, Sep. 2010, 31(17):2903-12. doi: 10.1002/elps.200900764.
Binding data for Rituximab (submitted by the Opponent during EP opposition procedure for EP 2 708 558 and posted by EPO on Jan. 15, 2019), 6 pages.
Chang et al., "Practical Approaches to Protein Formulation Development," Pharm Biotechnol, 2002, 13:1-25.
Gopferich et al., Chapter 15 " Drug Delivery from Biorodible Polymers," in Formulation and Delivery of Proteins and Peptides, American Chemical Society, Editors Cleland et al., 1994, pp. 242-277.
Costa et al., "Efficacy of tocilizumab in a patient with refractory psoriatic arthritis," Clin Rheumatol, Sep. 2014, 33(9):1355-7.
Decision of the Opposition Division in EP 2 275 443, dated Apr. 26, 2018 (submitted on May 24, 2019 by the Patentee during EPO Opposition Procedure for EP 2 202 245), 29 pages.
Declaration of Taichi Kuramochi (submitted on May 24, 2019 by the Patentee during EPO Opposition Procedure for EP 2 202 245), 11 pages.
Declaration of Dr. Anette Henriksen, signed Apr. 17, 2019 (submitted by the Opponent during EPO opposition procedure for EP 2 006 381), 4 pages.
Declaration by Madhusudan Natarajan, Ph.D. (submitted by the Opponent during EP opposition procedure for EP 2 708 558 and posted by EPO on Jan. 15, 2019), 3 pages.
Ferl et al., "A Predictive Model of Therapeutic Monoclonal Antibody Dynamics and Regulation by the Neonatal Fc Receptor (FcRn)," Ann Biomed Eng, Nov. 2005, 33(11):1640-52; and Erratum, Oct. 2011, 39(10):2668.
Fisher et al., "Affinity purification of antibodies using antigens immobilized on solid supports," Biochem Soc Trans, Apr. 1988, 16(2):134-8.
Furuya et al., "Interleukin-6 as a Potential Therapeutic Target for Pulmonary Arterial Hypertension," Int J Rheumatol, Aug. 2010, 2010:720305:1-8. doi: 10.1155/2010/720305. Epub Aug. 2, 2010.
Granted claims of EP 2 275 443 (submitted on May 24, 2019 by the Patentee during EPO Opposition Procedure for EP 2 202 245), 1 page.
Hashizume et al., "Tocilizumab, a humanized anti-interleukin-6 receptor antibody, improved anemia in monkey arthritis by suppressing IL-6-induced hepcidin production," Rheumatol Int, May 2010, 30(7):917-23. doi: 10.1007/s00296-009-1075-4. Epub Jul. 29, 2009.
Honda et al., "Marginal zone B cells exacerbate endotoxic shock via interleukin-6 secretion induced by Fca/mR-coupled TLR4 signalling," Nat Commun, May 5, 2016, 7:11498. doi: 10.1038/ncomms11498.
Hughes-Jones et al., "The Effect of pH and Ionic Strength on the Reaction between Anti-D and Erythrocytes," Immunology, Jan. 1964, 7:72-81.
Huse et al., "Purification of antibodies by affinity chromatography," J Biochem Biophys Methods, May 31, 2002, 51(3):217-31.
Iijima et al., "Tocilizumab improves systemic rheumatoid vasculitis with necrotizing crescentic glomerulonephritis," Mod Rheumatol, Jan. 2015, 25(1):138-42. doi: 0.3109/14397595.2013.874748. Epub Feb. 18, 2014.
Jain et al., "Engineering antibodies for clinical applications," Trends Biotechnol, Jul. 2007, 25(7):307-16. Epub May 21, 2007.
Kamata et al., "Comparison of pH and Ionic Strength Dependence of Interactions between Monoclonal Antibodies and Bovine β-Lactoglobulin," Biosci Biotechnol Biochem, Jan. 1996, 60(1):25-9.
King, Chapter 2 "Antibody Engineering: Design for Specific Applications," in Applications and Engineering of Monoclonal Antibodies, 1998:27-75.
Kishimoto, "Interleukin-6 and its Receptor in Autoimmunity," J Autoimmun, Apr. 1992, 5 Suppl A:123-32.
Kondo et al., "A case of overlap syndrome successfully treated with tocilizumab: a hopeful treatment strategy for refractory dermatomyositis? ," Rheumatology (Oxford), Oct. 2014, 53(10):1907-8. doi: 10.1093/rheumatology/keu234. Epub May 23, 2014.
Kranz et al., "Mechanisms of Ligand Binding by Monoclonal Anti-fluorescyl Antibodies," J Biol Chem, Jun. 25, 1982, 257(12):6987-95.
Mihara et al., "Anti-interleukin 6 receptor antibody inhibits murine AA-amyloidosis," J. Rheumatol, Jun. 2004, 31(6):1132-8.
Mori et al., "Novel models of cancer-related anemia in mice inoculated with IL-6-producing tumor cells," Biomed Res, Feb. 2009, 30(1):47-51.
Motozawa et al., "Unique circumferential peripheral keratitis in relapsing polychondritis," Medicine (Baltimore), Oct. 2017, 96(41):e7951. doi: 10.1097/MD.0000000000007951.
Narazaki et al., "Therapeutic effect of tocilizumab on two patients with polymyositis," Rheumatology (Oxford), Jul. 2011, 50(7): 1344-6. doi: 10.1093/rheumatology/ker152. Epub Apr. 2011.
Narhi et al., "Effect of Three Elution Buffers on the Recovery and Structure of Monoclonal Antibodies," Anal Biochem, Nov. 15, 1997, 253(2):236-45.
Originally Filed Claims of EP Application No. 13195713.6 (EP Publication No. 2 708 558) (submitted by the Opponent during EP opposition procedure for EP 2 708 558 and posted by EPO on Jan. 15, 2019), 2 pages.
Originally Filed Description of EP Application No. 13195713.6 (EP Publication No. 2 708 558) (submitted by the Opponent during EP opposition proceudre for EP 2 708 558 and posted by EPO on Jan. 15, 2019), 153 pages.

(56) References Cited

OTHER PUBLICATIONS

Patel et al., "A Forgotten Cause of Kidney Injury in Chronic Myelomonocytic Leukemia," Am J Kidney Dis, Jul. 2009, 54(1):159-64. doi: 10.1053/j.ajkd.2008.11.013. Epub Jan. 29, 2009.
Patton et al., "An acid dissociation bridging ELISA for detection of antibodies directed against therapeutic proteins in the presence of antigen," J Immunol Methods, Sep. 2005, 304(1-2):189-95.
Product Information Sheet from SIGMA—H-Y Medium (1998) and document establishing that it was published in 1998, 4 pages (submitted by the Opponent during EP opposition procedure for EP 2 708 558 and posted by EPO on Jan. 15, 2019).
Promega Protocols and Applications Guide, 1991, 2nd Edition (submitted by the Opponent during EP opposition procedure for EP 2 708 558 and posted by EPO on Jan. 14, 2019), 3 pages.
Raso, "Intracellular Targeting Using Bispecific Antibodies," Methods in Molecular Medicine, vol. 25: Drug Targeting: Strategies, Principles, and Applications, 2000, pp. 37-50.
Raso et al., "Intracellular Targeting with Low pH-triggered Bispecific Antibodies," J Biol Chem, Oct. 31, 1997, 272(44):27623-8.
Raso et al., "Antibodies Capable of Releasing Diphtheria Toxin in Response to the Low pH Found in Endosomes," J Biol Chem, Oct. 31, 1997, 272(44):27618-22.
Reverberi et al., "Factors affecting the antigen-antibody reaction," Blood Transfus, Nov. 2007, 5(4):227-40. doi: 10.2450/2007.0047-07.
Rituximab biologic license application approval, dated Nov. 26, 1997 (submitted by the Opponent during EP opposition procedure for EP 2 708 558 and posted by EPO on Jan. 15, 2019), 2 pages.
Rituximab, Wikipedia (https://de.wikipedia.org/wiki /Rituximab), accessed on Oct. 24, 2018, (submitted by the Opponent during EP opposition procedure for EP 2 708 558 and posted by EPO on Jan. 15, 2019), 7 pages (with English translation).
Rituximab product information, IDEC Pharmaceuticals Corporation, Nov. 1997, (submitted by the Opponent during EP opposition procedure for EP 2 708 558 and posted by EPO on Jan. 15, 2019), 2 pages.
Sada et al., "Effect of histidine residues in antigenic sites on pH dependence of immuno-adsorption equilibrium," Appl Microbiol Biotechnol, Feb. 1988, 27:528-32.
Serada et al., "IL-6 blockade inhibits the induction of myelin antigen-specific Th17 cells and Th1 cells in experimental autoimmune encephalomyelitis," Proc Natl Acad Sci USA, Jul. 1, 2008, 105(26):9041-6. doi: 10.1073/pnas.0802218105. Epub Jun. 24, 2008.
Shadduck et al., "Fractionation of Antibodies to L-Cell Colony-Stimulating Factor by Affinity Chromatography," Blood, Jun. 1979, 53(6):1182-90.
Shima et al., "Tocilizumab, a humanized anti-interleukin-6 receptor antibody, ameliorated clinical symptoms and MRI findings of a patient with ankylosing spondylitis," Mod Rheumatol, Aug. 2011, 21(4):436-9. doi: 10.1007/s10165-011-0416-9. Epub Feb. 9, 2011.
Shimizu et al., "Successful treatment with tocilizumab for refractory scleritis associated with relapsing polychondritis," Scand J Rheumatol, Sep. 2017, 46(5):418-419. doi: 10.1080/03009742.2016.1275774. Epub Jan. 25, 2017.
Silpa-Archa et al., "Outcome of tocilizumab treatment in refractory ocular inflammatory diseases," Acta Ophthalmol, Sep. 2016, 94(6):e400-6. doi: 10.1111/aos.13015. Epub Mar. 24, 2016.
Supplemental Material to Raposo et al., "Epitope-specific antibody response is controlled by immunoglobulin VH polymorphisms," J Exp Med, Mar. 10, 2014, 211(3):405-11. doi: 10.1084/jem.20130968. Epub Feb. 17, 2014 (submitted on May 24, 2019 by the Patentee during EPO Opposition Procedure for EP 2 202 245), 4 pages.
Suzuki et al., "Anti-murine IL-6 receptor antibody inhibits IL-6 effects in vivo," Immunol Lett, Sep. 1991, 30(1):17-21.
Venturi et al., The Monoclonal Antibody 1F6 Identifies a pH-dependent Conformational Change in the Hydrophilic $NH_2$ Terminus of NhaA $Na^+/H^+$ Antiporter of *Escherichia coli*, J Biol Chem, Feb. 18, 2000, 275(7):4734-42.
Wang, "Instability, stabilization, and formulation of liquid protein pharmaceuticals," Int J Pharm, Aug. 20, 1999, 185(2):129-88.
USPTO Final Office Action in U.S. Appl. No. 15/495,026, dated Feb. 5, 2019, 22 pages.
U.S. Appl. No. 15/952,951, Igawa et al., filed Apr. 13, 2018.
U.S. Appl. No. 16/361,498, Igawa et al., filed Mar. 22, 2019.
Interleukin 6, Wikipedia, Feb. 22, 2019, XP055598802, (URL:https://protect-us.mimecast.com/s/6UxpCmZ28nsApl8JuGhTki?domain=en.wikipedia.org), retrieved on Jun. 24, 2019.
Chugai NMO Clinical Trial Webinar, Sakura Star Study, dated Dec. 12, 2014, downloaded on Sep. 5, 2019 from https://s3.amazonaws.com/gjcf-wp-uploads/wp-content/uploads/2016/05/16162202/12_12_14_Chugai_Webinar_PPT_Complete_Deck_FINAL.pdf, 18 pages.
Chugai Pharmaceutical, A phase I, multiple-dose study of SA237, Study JapicCTI-No. 121786; submitted to Clinicaltrials.jp on Jan. 31, 2014; downloaded from clinicaltrials.jp archive on Sep. 5, 2019 as https://www.clinicaltrials.jp/cti-user/trial/Show.jsp, 5 pages.
Chugai Pharmaceutical, A phase I, multiple-dose study of SA237, Study JapicCTI-No. 121786; submitted to Clinicaltrials.jp on Jun. 19, 2012; downloaded from clinicaltrials.jp archive on Sep. 5, 2019 as https://www.clinicaltrials.jp/cti-user/trial/Show.jsp, 5 pages.
Chugai Pharmaceutical, A phase I, multiple-dose study of SA237, Study JapicCTI-No. 121786; submitted to Clinicaltrials.jp on Mar. 19, 2012; downloaded from clinicaltrials.jp archive on Sep. 5, 2019 as https://www.clinicaltrials.jp/cti-user/trial/Show.jsp, 5 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 1; submitted to ClinicalTrials.gov on Jan. 6, 2014; downloaded from ClinicalTrials.gov archive on Sep. 4, 2019 as https://clinicaltrials.gov/ct2/history/NCT02028884?V_1=View#StudyPageTop, 6 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 2; submitted to ClinicalTrials.gov on Feb. 25, 2014; downloaded from ClinicalTrials.gov archive on Sep. 4, 2019 as https://clinicaltrials.gov/ct2/history/NCT02028884?V_2=View#StudyPageTop, 6 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 3; submitted to ClinicalTrials.gov on Sep. 4, 2015; downloaded from ClinicalTrials.gov archive on Sep. 4, 2019 as https://clinicaltrials.gov/ct2/history/NCT02028884?V_3=View#StudyPageTop, 6 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 4; submitted to ClinicalTrials.gov on Dec. 8, 2015; downloaded from ClinicalTrials.gov archive on Sep. 4, 2019 as https://clinicaltrials.gov/ct2/history/NCT02028884?V_4=View#StudyPageTop, 6 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 1; submitted to ClinicalTrials.gov on Feb. 25, 2014; downloaded from ClinicalTrials.gov archive on Sep. 4, 2019 as https://clinicaltrials.gov/ct2/history/NCT02073279?V_1=View#StudyPageTop, 6 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 2; submitted to ClinicalTrials.gov on Jul. 22, 2014; downloaded from ClinicalTrials.gov archive on Sep. 5, 2019 as https://clinicaltrials.gov/ct2/history/NCT02073279?V_2=View#StudyPageTop, 6 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 3; submitted to ClinicalTrials.gov on

(56) References Cited

OTHER PUBLICATIONS

Dec. 15, 2014; downloaded from ClinicalTrials.gov archive on Sep. 5, 2019 as https://clinicaltrials.gov/ct2/history/NCT02073279?V_3=View#StudyPageTop, 7 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 4; submitted to ClinicalTrials.gov on Feb. 5, 2015; downloaded from ClinicalTrials.gov archive on Sep. 5, 2019 as https://clinicaltrials.gov/ct2/history/NCT02073279?V_4=View#StudyPageTop, 8 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 5; submitted to ClinicalTrials.gov on Feb. 6, 2015; downloaded from ClinicalTrials.gov archive on Sep. 5, 2019 as https://clinicaltrials.gov/ct2/history/NCT02073279?V_5=View#StudyPageTop, 8 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 6; submitted to ClinicalTrials.gov on Mar. 4, 2015; downloaded from ClinicalTrials.gov archive on Sep. 5, 2019 as https://clinicaltrials.gov/ct2/history/NCT02073279?V_6=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 7; submitted to ClinicalTrials.gov on Apr. 1, 2015; downloaded from ClinicalTrials.gov archive on Sep. 5, 2019 as https://clinicaltrials.gov/ct2/history/NCT02073279?V_7=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 8; submitted to ClinicalTrials.gov on May 7, 2015; downloaded from ClinicalTrials.gov archive on Sep. 5, 2019 as https://clinicaltrials.gov/ct2/history/NCT02073279?V_8=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 9; submitted to ClinicalTrials.gov on Jun. 5, 2015; downloaded from ClinicalTrials.gov archive on Sep. 5, 2019 as https://clinicaltrials.gov/ct2/history/NCT02073279?V_9=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 10; submitted to ClinicalTrials.gov on Jul. 7, 2015; downloaded from ClinicalTrials.gov archive on Sep. 5, 2019 as https://clinicaltrials.gov/ct2/history/NCT02073279?V_10=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 11; submitted to ClinicalTrials.gov on Aug. 3, 2015; downloaded from ClinicalTrials.gov archive on Sep. 5, 2019 as https://clinicaltrials.gov/ct2/history/NCT02073279?V_11=View#StudyPageTop, 10 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 12; submitted to ClinicalTrials.gov on Sep. 3, 2015; downloaded from ClinicalTrials.gov archive on Sep. 5, 2019 as https://clinicaltrials.gov/ct2/history/NCT02073279?V_12=View#StudyPageTop, 10 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 13; submitted to ClinicalTrials.gov on Oct. 5, 2015; downloaded from ClinicalTrials.gov archive on Sep. 5, 2019 as https://clinicaltrials.gov/ct2/history/NCT02073279?V_13=View#StudyPageTop, 10 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 14; submitted to ClinicalTrials.gov on Dec. 8, 2015; downloaded from ClinicalTrials.gov archive on Sep. 5, 2019 as https://clinicaltrials.gov/ct2/history/NCT02073279?V_14=View#StudyPageTop, 10 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Germany; submitted to clinicaltrialsregister.eu on Dec. 20, 2013; downloaded from clinicaltrialsregister.eu archive on Sep. 5, 2019 as https://www.clinicaltrialsregister.eu/ctr-search/trial/2013-003752-21/DE, 7 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Hungary; submitted to clinicaltrialsregister.eu on Feb. 25, 2015; downloaded from clinicaltrialsregister.eu archive on Sep. 5, 2019 as https://www.clinicaltrialsregister.eu/ctr-search/trial/2013-003752-21/HU, 6 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Italy; submitted to clinicaltrialsregister.eu on Feb. 6, 2014; downloaded from clinicaltrialsregister.eu archive on Sep. 5, 2019 as https://www.clinicaltrialsregister.eu/ctr-search/trial/2013-003752-21/IT, 5 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Poland; submitted to clinicaltrialsregister.eu on Oct. 15, 2013; downloaded from clinicaltrialsregister.eu archive on Sep. 5, 2019 as https://www.clinicaltrialsregister.eu/ctr-search/trial/2013-003752-21/PL, 7 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Spain; submitted to clinicaltrialsregister.eu on Mar. 11, 2015; downloaded from clinicaltrialsregister.eu archive on Sep. 5, 2019 as https://www.clinicaltrialsregister.eu/ctr-search/trial/2013-003752-21/ES, 7 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in the United Kingdom; submitted to clinicaltrialsregister.eu on Oct. 15, 2013; downloaded from clinicaltrialsregister.eu archive on Sep. 5, 2019 as https://www.clinicaltrialsregister.eu/ctr-search/trial/2013-003752-21/GB, 6 pages.

F. Hoffmann-La Roche Ltd., A Multicenter, Randomized, Double-blind, Placebo-controlled, Phase 3 Study to Evaluate the Efficacy and Safety of Satralizumab (SA237) as Monotherapy in Patients with Neuromyelitis Optica (NMO) and Neuromyelitis Optica Spectrum Disorder (NMOSD), Study EudraCT 2015-005431-41 in Croatia; submitted to clinicatltrialsregister.eu on Dec. 15, 2016; downloaded from clnicaltrialsregister.eu archive on Sep. 5, 2019 as https://www.clinicaltrialsregister.eu/ctr-search/trial/2015-005431-41/HR, 6 pages.

F. Hoffmann-La Roche Ltd., A Multicenter, Randomized, Double-blind, Placebo-controlled, Phase 3 Study to Evaluate the Efficacy and Safety of Satralizumab (SA237) as Monotherapy in Patients with Neuromyelitis Optica (NMO) and Neuromyelitis Optica Spectru

(56) References Cited

OTHER PUBLICATIONS

Disorder (NMOSD), Study EudraCT 2015-005431-41 in Poland; submitted to clinicaltrialsregister.eu on Apr. 7, 2016; downloaded from clinicaltrialsregister.eu archive on Sep. 5, 2019 as https://www.clinicaltrialsregister.eu/ctr-search/trial/2015-005431-41/PL, 6 pages.

Kakita et al., "Isolation of a human monoclonal antibody with strong neutralizing activity against Diptheheria toxin," Infection and Immunity, Jun. 2006, pp. 3682-3683.

USPTO Final Office Action in U.S. Appl. No. 15/495,026, dated Sep. 9, 2019, 23 pages.

| CDR CLASSI-FICATION | TOCILIZUMAB CDR SEQUENCE | MUTATION SITE (Kabat No.) | AMINO ACID OF TOCILIZUMAB | AMINO ACID AFTER MUTATION | CDR SEQUENCE AFTER MUTATION |
|---|---|---|---|---|---|
| HCDR2 | YISYSGITTYNPSLKS | 50 | Y | F | FISYSGITTYNPSLKS (SEQ ID NO: 82) |
| HCDR2 | YISYSGITTYNPSLKS (SEQ ID NO: 81) | 58 | T | N | YISYSGITNYNPSLKS (SEQ ID NO: 83) |
| HCDR3 | SLARTTAMDY | 95 | S | L | LLARTTAMDY (SEQ ID NO: 85) |
| HCDR3 | SLARTTAMDY (SEQ ID NO: 84) | 99 | T | A | SLARATAMDY (SEQ ID NO: 86) |
| LCDR1 | RASQDISSYLN | 27 | Q | T | RASTDISSYLN (SEQ ID NO: 88) |
| LCDR1 | RASQDISSYLN (SEQ ID NO: 87) | 27 | Q | R | RASRDISSYLN (SEQ ID NO: 89) |
| LCDR3 | QQGNTLPYT | 89 | Q | G | GQGNTLPYT (SEQ ID NO: 91) |
| LCDR3 | QQGNTLPYT (SEQ ID NO: 90) | 93 | T | R | QQGNRLPYT (SEQ ID NO: 92) |

| CLASSI-FICATION | TOCILIZUMAB SEQUENCE | MUTATION SITE (Kabat No.) | AMINO ACID OF TOCILIZUMAB | AMINO ACID AFTER MUTATION | SEQUENCE AFTER MUTATION |
|---|---|---|---|---|---|
| HFR1 | QVQLQESGPGLVRPSQTLSLTC TVSGYSIT (SEQ ID NO: 93) | 13<br>16<br>23*<br>30* | R<br>Q<br>T<br>T | K<br>E<br>A<br>S | QVQLQESGPGLVKPSETLSLTC AVSGYSIS (SEQ ID NO: 94) |
| HCDR1 | SDHAWS (SEQ ID NO: 95) | 31 | S | D | DDHAWS (SEQ ID NO: 96) |
| HFR2 | WVRQPPGRGLEWIG (SEQ ID NO: 97) | 43 | R | E | WVRQPPGEGLEWIG (SEQ ID NO: 98) |
| HCDR2 | YISYSGITTYNPSLKS (SEQ ID NO: 81) | 64<br>65 | K<br>S | Q<br>D | YISYSGITTYNPSLQD (SEQ ID NO: 99) |
| HFR4 | WGQGSLVTVSS (SEQ ID NO: 100) | 105<br>107* | Q<br>S | E<br>T | WGEGTLVTVSS (SEQ ID NO: 101) |
| LFR1 | DIQMTQSPSSLSASVGDRVTITC (SEQ ID NO: 102) | 18 | R | S | DIQMTQSPSSLSASVGDSVTITC (SEQ ID NO: 103) |
| LCDR1 | RASQDISSYLN (SEQ ID NO: 87) | 24 | R | Q | QASQDISSYLN (SEQ ID NO: 104) |
| LFR2 | WYQQKPGKAPKLLIY (SEQ ID NO: 105) | 45 | K | E | WYQQKPGKAPELLIY (SEQ ID NO: 106) |
| LCDR2 | YTSRLHS (SEQ ID NO: 107) | 53<br>55 | R<br>H | E<br>E | YTSELES (SEQ ID NO: 108) |
|  |  | 55 | H | L | YTSRLLS (SEQ ID NO: 109) |
| LFR3 | GVPSRFSGSGSGTDFTFTISSLQPE DIATYYC (SEQ ID NO: 110) | 80<br>81*<br>83* | Q<br>P<br>I | E<br>A<br>A | GVPSRFSGSGSGTDFTFTISSLEAE DAATYYC (SEQ ID NO: 111) |
| LFR4 | FGQGTKVEIK (SEQ ID NO: 112) | 107 | K | E | FGQGTKVEIE (SEQ ID NO: 113) |

FIG. 3

| CLASSI-FICATION | TOCILIZUMAB SEQUENCE | MUTATION SITE (Kabat No.) | AMINO ACID OF TOCILIZUMAB | AMINO ACID AFTER MUTATION | SEQUENCE AFTER MUTATION |
| --- | --- | --- | --- | --- | --- |
| HFR1 | QVQLQESGPGLVRPSQTLSLTCTVSGYSIT (SEQ ID NO: 93) | 27 | Y | H | QVQLQESGPGLVRPSQTLSLTCTVSGHSIT (SEQ ID NO: 114) |
| HCDR1 | SDHAWS (SEQ ID NO: 95) | 31 | S | H | HDHAWS (SEQ ID NO: 115) |
| LCDR1 | RASQDISSYLN (SEQ ID NO: 87) | 32 | Y | H | RASQDISSHLN (SEQ ID NO: 116) |
| LCDR2 | YTSRLHS (SEQ ID NO: 107) | 53 | R | H | YTSHLHS (SEQ ID NO: 117) |

FIG. 8

METHODS OF REDUCING IL-6 ACTIVITY FOR DISEASE TREATMENT

CROSS-REFERENCE TO RELATED APPLICATIONS

This application is a continuation of U.S. application Ser. No. 13/524,528, filed on Jun. 15, 2012, which is a divisional of U.S. application Ser. No. 12/680,087, filed on Jan. 3, 2011 (now U.S. Pat. No. 8,562,991), which is the National Stage of International Application Serial No. PCT/JP2009/066590, filed on Sep. 25, 2009, which claims the benefit of Japanese Application Serial Nos. 2009-067925, filed on Mar. 19, 2009; 2009-060806, filed on Mar. 13, 2009; and 2008-248213, filed on Sep. 26, 2008. The contents of the foregoing applications are incorporated by reference herein.

TECHNICAL FIELD

The present invention relates to pharmaceutical compositions comprising an anti-IL-6 receptor antibody as an active ingredient, methods for producing the compositions, and such.

BACKGROUND ART

Antibodies are drawing attention as pharmaceuticals as they are highly stable in plasma and have few adverse effects. Among them, a number of IgG-type antibody pharmaceuticals are available on the market and many antibody pharmaceuticals are currently under development (Non-Patent Documents 1 and 2). IL-6 is a cytokine involved in various autoimmune diseases, inflammatory diseases, malignant tumors, and so on (Non-Patent Document 3). TOCILIZUMAB, a humanized anti-IL-6 receptor IgG1 antibody, specifically binds to the IL-6 receptor. It is thought that TOCILIZUMAB can be used as a therapeutic agent for IL-6-associated diseases such as rheumatoid arthritis, since it neutralizes the biological activity of IL-6 (Patent Documents 1 to 3, and Non-Patent Document 4). TOCILIZUMAB has been approved as a therapeutic agent for Castleman's disease and rheumatoid arthritis in Japan (Non-Patent Document 5).

Humanized antibodies such as TOCILIZUMAB are first-generation antibody pharmaceuticals. Second-generation antibody pharmaceuticals are currently being developed by improving the efficacy, convenience, and cost of first-generation antibody pharmaceuticals. Various technologies that are applicable to second-generation antibody pharmaceuticals are being developed. Technologies for enhancing effector function, antigen-binding ability, pharmacokinetics, and stability, as well as technologies for reducing the risk of immunogenicity have been reported. As methods for enhancing drug efficacy or reducing dosage, technologies that enhance antibody-dependent cell-mediated cytotoxic activity (ADCC activity) or complement-dependent cytotoxic activity (CDC activity) through amino acid substitution in the Fc region of an IgG antibody have been reported (Non-Patent Document 6). Furthermore, affinity maturation has been reported as a technology for enhancing antigen-binding ability or antigen-neutralizing ability (Non-Patent Document 7). This technology enables one to enhance antigen-binding activity by introducing amino acid mutations into the complementarity determining (CDR) region of a variable region or such. The enhancement of antigen-binding ability improves in vitro biological activity or reduces dosage, and furthermore improves in vivo efficacy (Non-Patent Document 8). Currently, clinical trials are being conducted to assess Motavizumab (produced by affinity maturation), which is expected to have a superior efficacy than Palivizumab, a first-generation anti-RSV antibody pharmaceutical (Non-Patent Document 9). An anti-IL-6 receptor antibody with an affinity of about 0.05 nM (i.e., greater affinity than that of TOCILIZUMAB) has been reported (Patent Document 4). However, there is no report describing a human, humanized, or chimeric antibody having an affinity greater than 0.05 nM.

A problem encountered with current antibody pharmaceuticals is the high production cost associated with the administration of extremely large quantities of protein. For example, the dosage of TOCILIZUMAB, a humanized anti-IL-6 receptor IgG1 antibody, has been estimated to be about 8 mg/kg/month by intravenous injection (Non-Patent Document 4). Its preferred form of administration is subcutaneous formulation in chronic autoimmune diseases. In general, it is necessary that subcutaneous formulations are high-concentration formulations. From the perspective of stability or such, the limit for IgG-type antibody formulations is generally about 100 mg/ml (Non-Patent Document 10). Low-cost, convenient second-generation antibody pharmaceuticals that can be administered subcutaneously in longer intervals can be provided by increasing the half-life of an antibody in the plasma to prolong its therapeutic effect and thereby reduce the amount of protein administered, and by conferring the antibody with high stability.

FcRn is closely involved in antibody pharmacokinetics. With regard to differences in the plasma half-life of antibody isotypes, IgG1 and IgG2 are known to have superior plasma half-life than IgG3 and IgG4 (Non-Patent Document 11). As a method for further improving the plasma half-life of IgG1 and IgG2 antibodies which have superior plasma half-lives, substitution of amino acids in the constant region which enhances the binding to FcRn has been reported (Non-Patent Documents 12 and 13). From the viewpoint of immunogenicity, further improvement of the plasma half-life is performed by substituting amino acids preferably in the variable region rather than in the constant region (Patent Document 5). However, there is no report to date on the improvement of the plasma half-life of IL-6 receptor antibodies through alteration of the variable region.

Another important problem encountered in the development of biopharmaceuticals is immunogenicity. In general, the immunogenicity of mouse antibodies is reduced by antibody humanization. It is assumed that immunogenicity risk can be further reduced by using a germline framework sequence as a template in antibody humanization (Non-Patent document 14). However, even Adalimumab, a fully human anti-TNF antibody, showed high-frequency (13% to 17%) immunogenicity, and the therapeutic effect was found to be reduced in patients who showed immunogenicity (Non-Patent documents 15 and 16). T-cell epitopes may be present even in the CDR of human antibodies, and these T-cell epitopes in CDR are a possible cause of immunogenicity. In silico and in vitro methods for predicting T-cell epitopes have been reported (Non-Patent documents 17 and 18). It is assumed that immunogenicity risk can be reduced by removing T-cell epitopes predicted using such methods (Non-Patent document 19).

TOCILIZUMAB, a humanized anti-IL-6 receptor IgG1 antibody, is an IgG1 antibody obtained by humanizing mouse antibody PM1. CDR grafting is carried out using human NEW and REI sequences as template framework for H and L chains, respectively; however, five mouse sequence amino acids are retained in the framework as essential amino acids for maintaining the activity (Non-Patent Document 20). There is no previous report that fully humanizes the remaining mouse sequence in the framework of the humanized antibody TOCILIZUMAB without reducing the activity. Furthermore, the CDR sequence of TOCILIZUMAB is a mouse sequence, and thus, like Adalimumab, it may have T-cell epitopes in the CDR, which may have a potential immunogenicity risk. In clinical trials of TOCILIZUMAB, anti-TOCILIZUMAB antibodies were not detected at the effective dose of 8 mg/kg, but they were observed at the doses of 2 mg/kg and 4 mg/kg (Patent Document 6). These suggest that there is still room for improvement for the immunogenicity of TOCILIZUMAB. However, there has been no report on reducing the immunogenicity risk of TOCILIZUMAB by amino acid substitution.

The isotype of TOCILIZUMAB is IgG1. The isotype difference refers to difference in the constant region sequence. Since the constant region sequence is assumed to have strong influence on the effector function, pharmacokinetics, physical properties, and so on, selection of the constant region sequence is very important for the development of antibody pharmaceuticals (Non-Patent Document 11). In recent years, the safety of antibody pharmaceuticals has become of great importance. Interaction between the antibody Fc portion and Fcγ receptor (effector function) may have caused serious adverse effects in phase-I clinical trials of TGN1412 (Non-Patent Document 21). For antibody pharmaceuticals designed to neutralize the biological activity of an antigen, the binding to Fcγ receptor, which is important for effector functions such as ADCC, is unnecessary. The binding to Fcγ receptor may even be unfavorable from the viewpoint of adverse effects. A method for reducing the binding to Fcγ receptor is to alter the isotype of an IgG antibody from IgG1 to IgG2 or IgG4 (Non-Patent Document 22). IgG2 is more favorable than IgG4 from the viewpoint of pharmacokinetics and Fcγ receptor I binding (Non-Patent Document 11). TOCILIZUMAB is an IL-6 receptor-neutralizing antibody, and its isotype is IgG1. Thus, in view of the potential adverse effects, IgG2 may be a preferred isotype since effector functions such as ADCC are not needed.

Meanwhile, when developing antibody pharmaceuticals, physicochemical properties of the proteins, in particular, homogeneity and stability are very crucial. It has been reported that for the IgG2 isotype, there is significant heterogeneity derived from the disulfide bonds in the hinge region (Non-Patent Document 23). It is not easy and would be more costly to manufacture them as pharmaceutical in large-scale while maintaining the objective substances/related heterogeneity derived from disulfide bonds between productions. Thus, single substances are desirable as much as possible. Furthermore, for heterogeneity of the H-chain C-terminal sequences of an antibody, deletion of C-terminal amino acid lysine residue, and amidation of the C-terminal carboxyl group due to deletion of both of the two C-terminal amino acids, glycine and lysine, have been reported (Non-Patent Document 24). In developing IgG2 isotype antibodies as pharmaceuticals, it is preferable to reduce such heterogeneity and maintain high stability. To produce convenient, stable, high-concentration, subcutaneously-administered formulations, it is preferable that not only the stability is high, but also the plasma half-life is superior to that of IgG1 which is the isotype of TOCILIZUMAB. However, there is no previous report on constant region sequences for antibodies with the IgG2-isotype constant region that have reduced heterogeneity, high stability, and superior plasma half-life than antibodies with the IgG1 isotype constant region.

Prior art documents related to the present invention are shown below:

PRIOR ART DOCUMENTS

Patent Documents

[Patent Document 1] WO 92/19759
[Patent Document 2] WO 96/11020
[Patent Document 3] WO 96/12503
[Patent Document 4] WO 2007/143168
[Patent Document 5] WO 2007/114319
[Patent Document 6] WO 2004/096273

Non-Patent Documents

[Non-Patent Document 1] Janice M Reichert, Clark J Rosensweig, Laura B Faden & Matthew C Dewitz, Monoclonal antibody successes in the clinic, Nature Biotechnology 23, 1073-1078 (2005).
[Non-Patent Document 2] Pavlou A K, Belsey M J., The therapeutic antibodies market to 2008., Eur J Pharm Biopharm. 2005 April; 59(3):389-96.
[Non-Patent Document 3] Nishimoto N, Kishimoto T., Interleukin 6: from bench to bedside., Nat Clin Pract Rheumatol. 2006 November; 2(11):619-26.
[Non-Patent Document 4] Maini R N, Taylor P C, Szechinski J, Pavelka K, Broll J, Balint G, Emery P, Raemen F, Petersen J, Smolen J, Thomson D, Kishimoto T; CHARISMA Study Group., Double-blind randomized controlled clinical trial of the interleukin-6 receptor antagonist, Tocilizumab, in European patients with rheumatoid arthritis who had an incomplete response to methotrexate., Arthritis Rheum. 2006 September; 54(9):2817-29.
[Non-Patent Document 5] Nishimoto N, Kanakura Y, Aozasa K, Johkoh T, Nakamura M, Nakano S, Nakano N, Ikeda Y, Sasaki T, Nishioka K, Hara M, Taguchi H, Kimura Y, Kato Y, Asaoku H, Kumagai S, Kodama F, Nakahara H, Hagihara K, Yoshizaki K, Kishimoto T. Humanized anti-interleukin-6 receptor antibody treatment of multicentric Castleman disease. Blood. 2005 Oct. 15; 106(8):2627-32.
[Non-Patent Document 6] Kim S J, Park Y, Hong H J., Antibody engineering for the development of therapeutic antibodies., Mol Cells. 2005 Aug. 31; 20(1):17-29. Review.
[Non-Patent Document 7] Rothe A, Hosse R J, Power B E. Ribosome display for improved biotherapeutic molecules. Expert Opin Biol Ther. 2006 February; 6(2):177-87.
[Non-Patent Document 8] Rajpal A, Beyaz N, Haber L, Cappuccilli G, Yee H, Bhatt R R, Takeuchi T, Lerner R A, Crea R., A general method for greatly improving the affinity of antibodies by using combinatorial libraries., Proc Natl Acad Sci USA. 2005 Jun. 14; 102(24):8466-71. Epub 2005 Jun. 6.
[Non-Patent Document 9] Wu H, Pfarr D S, Johnson S, Brewah Y A, Woods R M, Patel N K, White W I, Young J F, Kiener P A. Development of Motavizumab, an Ultra-potent Antibody for the Prevention of Respiratory Syncytial Virus Infection in the Upper and Lower Respiratory Tract. J Mol Biol. 2007, 368, 652-665.
[Non-Patent Document 10] Shire S J, Shahrokh Z, Liu J. Challenges in the development of high protein concentration formulations. J Pharm Sci. 2004 June; 93(6):1390-402.

[Non-patent Document 11] Salfeld J G. Isotype selection in antibody engineering. Nat Biotechnol. 2007 December; 25(12):1369-72.

[Non-Patent Document 12] Hinton P R, Xiong J M, Johlfs M G, Tang M T, Keller S, Tsurushita N., An engineered human IgG1 antibody with longer serum half-life., J Immunol. 2006 Jan. 1; 176(1):346-56.

[Non-Patent Document 13] Ghetie V, Popov S, Borvak J, Radu C, Matesoi D, Medesan C, Ober R J, Ward E S., Increasing the serum persistence of an IgG fragment by random mutagenesis., Nat Biotechnol. 1997 July; 15(7): 637-40.

[Non-Patent Document 14] Hwang W Y, Almagro J C, Buss T N, Tan P, Foote J. Use of human germline genes in a CDR homology-based approach to antibody humanization. Methods. 2005 May; 36(1):35-42.

[Non-Patent Document 15] Bartelds G M, Wijbrandts C A, Nurmohamed M T, Stapel S, Lems W F, Aarden L, Dijkmans B A, Tak P, Wolbink G J. Clinical response to adalimumab: The relationship with anti-adalimumab antibodies and serum adalimumab concentrations in rheumatoid arthritis. Ann Rheum Dis. 2007 Mar. 9; [Epub ahead of print]

[Non-Patent Document 16] Bender N K, Heilig C E, Droll B, Wohlgemuth J, Armbruster F P, Heilig B. Immunogenicity, efficacy and adverse events of adalimumab in RA patients. Rheumatol Int. 2007 January; 27(3):269-74.

[Non-Patent Document 17] Van Walle I, Gansemans Y, Parren P W, Stas P, Lasters I. Immunogenicity screening in protein drug development. Expert Opin Biol Ther. 2007 March; 7(3):405-18.

[Non-Patent Document 18] Jones T D, Phillips W J, Smith B J, Bamford C A, Nayee P D, Baglin T P, Gaston J S, Baker M P. Identification and removal of a promiscuous CD4+ T cell epitope from the C1 domain of factor VIII. J Thromb Haemost. 2005 May; 3(5):991-1000.

[Non-Patent Document 19] Chirino A J, Ary M L, Marshall S A. Minimizing the immunogenicity of protein therapeutics. Drug Discov Today. 2004 Jan. 15; 9(2):82-90.

[Non-Patent Document 20] Sato K, Tsuchiya M, Saldanha J, Koishihara Y, Ohsugi Y, Kishimoto T, Bendig M M. Reshaping a human antibody to inhibit the interleukin 6-dependent tumor cell growth. Cancer Res. 1993 Feb. 15; 53(4):851-6.

[Non-Patent Document 21] Strand V, Kimberly R, Isaacs J D. Biologic therapies in rheumatology: lessons learned future directions. Nat Rev Drug Discov. 2007 January; 6(1):75-92.

[Non-Patent Document 22] Gessner J E, Heiken H, Tamm A, Schmidt R E. The IgG Fc receptor family. Ann Hematol. 1998 June; 76(6):231-48.

[Non-Patent Document 23] Dillon T M, Ricci M S, Vezina C, Flynn G C, Liu Y D, Rehder D S, Plant M, Henkle B, Li Y, Deechongkit S, Varnum B, Wypych J, Balland A, Bondarenko P V. Structural and functional characterization of disulfide isoforms of the human IgG2 subclass. J Biol Chem. 2008 Jun. 6; 283(23):16206-15.

[Non-Patent Document 24] Johnson K A, Paisley-Flango K, Tangarone B S, Porter T J, Rouse J C. Cation exchange-HPLC and mass spectrometry reveal C-terminal amidation of an IgG1 heavy chain. Anal Biochem. 2007 Jan. 1; 360(1):75-83.

DISCLOSURE OF THE INVENTION

Problems to be Solved by the Invention

The present invention was achieved in view of the above circumstances. An objective of the present invention is to provide pharmaceutical compositions that comprise second-generation molecules that are superior than the humanized anti-IL-6 receptor IgG1 antibody TOCILIZUMAB, by altering the amino acid sequences of the variable and constant regions of TOCILIZUMAB to enhance the antigen-neutralizing ability and improve pharmacokinetics, such that prolonged therapeutic effect is exerted with a less frequency of administration, and immunogenicity, safety, and physicochemical properties (stability and homogeneity) are improved (hereinbelow, these pharmaceutical compositions may also be referred to as the "agents" or the "formulations"). Another objective is to provide methods for producing such pharmaceutical compositions.

Means for Solving the Problems

The present inventors conducted dedicated studies to generate second-generation molecules that are superior than the first-generation humanized anti-IL-6 receptor IgG1 antibody TOCILIZUMAB, by altering the amino acid sequences of the variable and constant regions of TOCILIZUMAB to enhance the efficacy and improve the pharmacokinetics, so that prolonged therapeutic effect is exerted with a lower frequency of administration, and immunogenicity, safety, and physicochemical properties (stability and homogeneity) are improved. As a result, the present inventors discovered multiple CDR mutations in the variable regions of TOCILIZUMAB that improve the binding ability (affinity) to the antigen. The present inventors thus successfully improved the affinity significantly using a combination of such mutations. The present inventors also succeeded in improving pharmacokinetics by introducing modifications that lower the isoelectric point of the variable region sequence. The present inventors also succeeded in improving pharmacokinetics by making the binding to the IL-6 receptor antigen to be pH-dependent, so that a single antibody molecule can neutralize the antigen multiple times. Furthermore, the present inventors successfully reduced the risk of immunogenicity by fully humanizing the mouse-derived sequences that remain in the framework of TOCILIZUMAB and reducing the number of T-cell epitope peptides in the variable regions predicted in silico. Furthermore, the present inventors also successfully discovered novel constant region sequences for the constant region of TOCILIZUMAB, that reduce the binding to the Fcγ receptor as compared to IgG1 to improve safety, improve the pharmacokinetics as compared to IgG1, and reduce the heterogeneity due to the disulfide bonds in the hinge region of IgG2 and the heterogeneity due to the H chain C-terminus without decreasing stability. The present inventors successfully produced second-generation molecules that are superior than TOCILIZUMAB by appropriately combining these amino acid sequence alterations in the CDR, variable regions, and constant regions.

The present invention relates to pharmaceutical compositions comprising a humanized anti-IL-6 receptor IgG antibody having superior antigen (IL-6 receptor)-binding ability, superior pharmacokinetics, superior safety and physical properties (stability and homogeneity), and further reduced immunogenicity risk, by altering the amino acid sequences of variable and constant regions of the humanized anti-IL-6 receptor IgG1 antibody TOCILIZUMAB; and methods for producing such pharmaceutical compositions. More specifically, the present invention provides:

[1] a polypeptide of any one of:

(a) a polypeptide that comprises CDR1 comprising the sequence of SEQ ID NO: 1 (CDR1 of VH4-M73), CDR2 comprising the sequence of SEQ ID NO: 2

(CDR2 of VH4-M73), and CDR3 comprising the sequence of SEQ ID NO: 3 (CDR3 of VH4-M73);
(b) a polypeptide that comprises CDR1 comprising the sequence of SEQ ID NO: 4 (CDR1 of VH3-M73), CDR2 comprising the sequence of SEQ ID NO: 5 (CDR2 of VH3-M73), and CDR3 comprising the sequence of SEQ ID NO: 6 (CDR3 of VH3-M73);
(c) a polypeptide that comprises CDR1 comprising the sequence of SEQ ID NO: 7 (CDR1 of VH5-M83), CDR2 comprising the sequence of SEQ ID NO: 8 (CDR2 of VH5-M83), and CDR3 comprising the sequence of SEQ ID NO: 9 (CDR3 of VH5-M83);
(d) a polypeptide that comprises CDR1 comprising the sequence of SEQ ID NO: 10 (CDR1 of VL1), CDR2 comprising the sequence of SEQ ID NO: 11 (CDR2 of VL1), and CDR3 comprising the sequence of SEQ ID NO: 12 (CDR3 of VL1);
(e) a polypeptide that comprises CDR1 comprising the sequence of SEQ ID NO: 13 (CDR1 of VL3), CDR2 comprising the sequence of SEQ ID NO: 14 (CDR2 of VL3), and CDR3 comprising the sequence of SEQ ID NO: 15 (CDR3 of VL3); and
(f) a polypeptide that comprises CDR1 comprising the sequence of SEQ ID NO: 16 (CDR1 of VL5), CDR2 comprising the sequence of SEQ ID NO: 17 (CDR2 of VL5), and CDR3 comprising the sequence of SEQ ID NO: 18 (CDR3 of VL5);

[2] an antibody of any one of:
(a) an antibody which comprises a heavy chain variable region that comprises CDR1 comprising the sequence of SEQ ID NO: 1 (CDR1 of VH4-M73), CDR2 comprising the sequence of SEQ ID NO: 2 (CDR2 of VH4-M73), and CDR3 comprising the sequence of SEQ ID NO: 3 (CDR3 of VH4-M73), and a light chain variable region that comprises CDR1 comprising the sequence of SEQ ID NO: 10 (CDR1 of VL1), CDR2 comprising the sequence of SEQ ID NO: 11 (CDR2 of VL1), and CDR3 comprising the sequence of SEQ ID NO: 12 (CDR3 of VL1);
(b) an antibody which comprises a heavy chain variable region that comprises CDR1 comprising the sequence of SEQ ID NO: 4 (CDR1 of VH3-M73), CDR2 comprising the sequence of SEQ ID NO: 5 (CDR2 of VH3-M73), and CDR3 comprising the sequence of SEQ ID NO: 6 (CDR3 of VH3-M73), and a light chain variable region that comprises CDR1 comprising the sequence of SEQ ID NO: 13 (CDR1 of VL3), CDR2 comprising the sequence of SEQ ID NO: 14 (CDR2 of VL3), and CDR3 comprising the sequence of SEQ ID NO: 15 (CDR3 of VL3); and
(c) an antibody which comprises a heavy chain variable region that comprises CDR1 comprising the sequence of SEQ ID NO: 7 (CDR1 of VH5-M83), CDR2 comprising the sequence of SEQ ID NO: 8 (CDR2 of VH5-M83), and CDR3 comprising the sequence of SEQ ID NO: 9 (CDR3 of VH5-M83), and a light chain variable region that comprises CDR1 comprising the sequence of SEQ ID NO: 16 (CDR1 of VL5), CDR2 comprising the sequence of SEQ ID NO: 17 (CDR2 of VL5), and CDR3 comprising the sequence of SEQ ID NO: 18 (CDR3 of VL5);

[3] a variable region of any one of:
(a) a heavy chain variable region comprising the sequence of SEQ ID NO: 19 (variable region of VH4-M73);
(b) a heavy chain variable region comprising the sequence of SEQ ID NO: 20 (variable region of VH3-M73);
(c) a heavy chain variable region comprising the sequence of SEQ ID NO: 21 (variable region of VH5-M83);
(d) a light chain variable region comprising the sequence of SEQ ID NO: 22 (variable region of VL1);
(e) a light chain variable region comprising the sequence of SEQ ID NO: 23 (variable region of VL3); and
(f) a light chain variable region comprising the sequence of SEQ ID NO: 24 (variable region of VL5);

[4] an antibody of any one of:
(a) an antibody that comprises a heavy chain variable region comprising the sequence of SEQ ID NO: 19 (variable region of VH4-M73) and a light chain variable region comprising the sequence of SEQ ID NO: 22 (variable region of VL1);
(b) an antibody that comprises a heavy chain variable region comprising the sequence of SEQ ID NO: 20 (variable region of VH3-M73) and a light chain variable region comprising the sequence of SEQ ID NO: 23 (variable region of VL3); and
(c) an antibody that comprises a heavy chain variable region comprising the sequence of SEQ ID NO: 21 (variable region of VH5-M83) and a light chain variable region comprising the sequence of SEQ ID NO: 24 (variable region of VL5);

[5] a heavy chain or light chain of any one of:
(a) a heavy chain comprising the sequence of SEQ ID NO: 25 (VH4-M73);
(b) a heavy chain comprising the sequence of SEQ ID NO: 26 (VH3-M73);
(c) a heavy chain comprising the sequence of SEQ ID NO: 27 (VH5-M83);
(d) a light chain comprising the sequence of SEQ ID NO: 28 (VL1);
(e) a light chain comprising the sequence of SEQ ID NO: 29 (VL3); and
(f) a light chain comprising the sequence of SEQ ID NO: 30 (VL5);

[6] an antibody of any one of:
(a) an antibody that comprises a heavy chain comprising the sequence of SEQ ID NO: 25 (VH4-M73) and a light chain comprising the sequence of SEQ ID NO: 28 (VL1);
(b) an antibody that comprises a heavy chain comprising the sequence of SEQ ID NO: 26 (VH3-M73) and a light chain comprising the sequence of SEQ ID NO: 29 (VL3); and
(c) an antibody that comprises a heavy chain comprising the sequence of SEQ ID NO: 27 (VH5-M83) and a light chain comprising the sequence of SEQ ID NO: 30 (VL5);

[7] a gene encoding the polypeptide of any one of [1] to [6];
[8] a vector carrying the gene of [7];
[9] a host cell carrying the vector of [8];
[10] a method for producing the polypeptide of any one of [1] to [6] by culturing the host cell of [9]; and
[11] a pharmaceutical composition comprising the polypeptide of any one of [1] to [6] or a polypeptide produced by the method of [10].

Effects of the Invention

The humanized anti-IL-6 receptor IgG antibodies obtained according to the present invention have enhanced efficacy and improved pharmacokinetics; thus, they can exert a prolonged therapeutic effect with a less administration frequency.

BRIEF DESCRIPTION OF THE DRAWINGS

FIG. 1 is a listing of mutation sites that improve the affinity of TOCILIZUMAB for the IL-6 receptor. The HCDR2 sequence of TOCILIZUMAB is shown in SEQ ID NO: 81; the HCDR2 sequence after mutation (upper line) is shown in SEQ ID NO: 82; the HCDR2 sequence after mutation (lower line) is shown in SEQ ID NO: 83; the HCDR3 sequence of TOCILIZUMAB is shown in SEQ ID NO: 84; the HCDR3 sequence after mutation (upper line) is shown in SEQ ID NO: 85; the HCDR3 sequence after mutation (lower line) is shown in SEQ ID NO: 86; the LCDR1 sequence of TOCILIZUMAB is shown in SEQ ID NO: 87; the LCDR1 sequence after mutation (upper line) is shown in SEQ ID NO: 88; the LCDR1 sequence after mutation (lower line) is shown in SEQ ID NO: 89; the LCDR3 sequence of TOCILIZUMAB is shown in SEQ ID NO: 90; the LCDR3 sequence after mutation (upper line) is shown in SEQ ID NO: 91; and the LCDR3 sequence after mutation (lower line) is shown in SEQ ID NO: 92.

FIG. 2 is a graph showing the neutralizing activities of TOCILIZUMAB and RDC-23 in BaF/gp130.

FIG. 3 is a listing of mutation sites that can reduce the isoelectric point of variable region without significantly reducing the binding of TOCILIZUMAB to the IL-6 receptor. Asterisk in the drawing represents a site that has no influence on the isoelectric point but which was mutated for conversion into a human sequence. The HFR1 sequence of TOCILIZUMAB is shown in SEQ ID NO: 93; the HFR1 sequence after mutation is shown in SEQ ID NO: 94; the HCDR1 sequence of TOCILIZUMAB is shown in SEQ ID NO: 95; the HCDR1 sequence after mutation is shown in SEQ ID NO: 96; the HFR2 sequence of TOCILIZUMAB is shown in SEQ ID NO: 97; the HFR2 sequence after mutation is shown in SEQ ID NO: 98; the HCDR2 sequence of TOCILIZUMAB is shown in SEQ ID NO: 81; the HCDR2 sequence after mutation is shown in SEQ ID NO: 99; the HFR4 sequence of TOCILIZUMAB is shown in SEQ ID NO: 100; the HFR4 sequence after mutation is shown in SEQ ID NO: 101; the LFR1 sequence of TOCILIZUMAB is shown in SEQ ID NO: 102; the LFR1 sequence after mutation is shown in SEQ ID NO: 103; the LCDR1 sequence of TOCILIZUMAB is shown in SEQ ID NO: 87; the LCDR1 sequence after mutation is shown in SEQ ID NO: 104; the LFR2 sequence of TOCILIZUMAB is shown in SEQ ID NO: 105; the LFR2 sequence after mutation is shown in SEQ ID NO: 106; the LCDR2 sequence of TOCILIZUMAB is shown in SEQ ID NO: 107; the LCDR2 sequences after mutation are shown in SEQ ID NOs: 108 and 109; the LFR3 sequence of TOCILIZUMAB is shown in SEQ ID NO: 110; the LFR3 sequence after mutation is shown in SEQ ID NO: 111; the LFR4 sequence of TOCILIZUMAB is shown in SEQ ID NO: 112; and the LFR4 sequence after mutation is shown in SEQ ID NO: 113.

FIG. 4 is a graph showing the neutralizing activities of TOCILIZUMAB and H53/L28 in BaF/gp130.

FIG. 5 is a graph showing the time courses of plasma concentration for TOCILIZUMAB and H53/L28 in mice after intravenous administration.

FIG. 6 is a graph showing the time courses of plasma concentration for TOCILIZUMAB and H53/L28 in mice after subcutaneous administration.

FIG. 7 is a schematic illustration showing that an IgG molecule can bind again to another antigen by dissociating from a membrane-type antigen in the endosome.

FIG. 8 is a listing of mutation sites that can confer pH dependency to the binding of TOCILIZUMAB to the IL-6 receptor (binding at pH 7.4 and dissociation at pH 5.8). The HFR1 sequence of TOCILIZUMAB is shown in SEQ ID NO: 93; the HFR1 sequence after mutation is shown in SEQ ID NO: 114; the HCDR1 sequence of TOCILIZUMAB is shown in SEQ ID NO: 95; the HCDR1 sequence after mutation is shown in SEQ ID NO: 115; the LCDR1 sequence of TOCILIZUMAB is shown in SEQ ID NO: 87; the LCDR1 sequence after mutation is shown in SEQ ID NO: 116; the LCDR2 sequence of TOCILIZUMAB is shown in SEQ ID NO: 107; and the LCDR2 sequence after mutation is shown in SEQ ID NO: 117.

FIG. 9 is a graph showing the neutralizing activities of TOCILIZUMAB and H3pI/L73 in BaF/gp130.

FIG. 10 is a graph showing the time courses of plasma concentration for TOCILIZUMAB and H3pI/L73 in cynomolgus monkeys after intravenous administration.

FIG. 11 is a graph showing the time courses of plasma concentration for TOCILIZUMAB and H3pI/L73 in human IL-6 receptor transgenic mice after intravenous administration.

FIG. 12 is a diagram showing the result of assessment of the C-terminus-derived heterogeneity of TOCILIZUMAB, TOCILIZUMABΔK, and TOCILIZUMABΔGK by cation exchange chromatography.

FIG. 13 is a diagram showing the result of assessment of the disulfide bond-derived heterogeneity of TOCILIZUMAB-IgG1, TOCILIZUMAB-IgG2, and TOCILIZUMAB-SKSC by cation exchange chromatography.

FIG. 14 is a diagram showing the denaturation curves for TOCILIZUMAB-IgG1, TOCILIZUMAB-IgG2, and TOCILIZUMAB-SKSC obtained by differential scanning calorimetry (DSC), and the Tm value for each Fab domain.

FIG. 15 is a graph showing the time courses of plasma concentration for TOCILIZUMAB-IgG1, TOCILIZUMAB-M44, TOCILIZUMAB-M58, and TOCILIZUMAB-M73 in human FcRn transgenic mice after intravenous administration.

FIG. 16 is a graph showing the neutralizing activities of TOCILIZUMAB, control, and Fv5-M83 in BaF/gp130.

FIG. 17 is a graph showing the neutralizing activities of TOCILIZUMAB, Fv3-M73, and Fv4-M73 in BaF/gp130.

FIG. 18 is a graph showing the time courses of plasma concentrations for TOCILIZUMAB, control, Fv3-M73, Fv4-M73, and Fv5-M83 in cynomolgus monkeys after intravenous administration.

FIG. 19 is a graph showing the time courses of CRP concentration for TOCILIZUMAB, control, Fv3-M73, Fv4-M73, or Fv5-M83 in cynomolgus monkeys after intravenous administration.

FIG. 20 is a graph showing the time courses of percentage of free soluble IL-6 receptor in cynomolgus monkeys after intravenous administration of TOCILIZUMAB, control, Fv3-M73, Fv4-M73, or Fv5-M83.

FIG. 21 is a graph showing the inhibitory effects by TOCILIZUMAB and Fv4-M73 on MCP-1 production from human RA patient-derived synovial cells.

FIG. 22 is a graph showing the inhibitory effects by TOCILIZUMAB and Fv4-M73 on VEGF production from human RA patient-derived synovial cells.

MODE FOR CARRYING OUT THE INVENTION

The present invention provides the polypeptides of (a) to (f) below:

(a) a polypeptide that comprises CDR1 comprising the sequence of SEQ ID NO: 1 (CDR1 of VH4-M73), CDR2 comprising the sequence of SEQ ID NO: 2

(CDR2 of VH4-M73), and CDR3 comprising the sequence of SEQ ID NO: 3 (CDR3 of VH4-M73);

Figure 2:
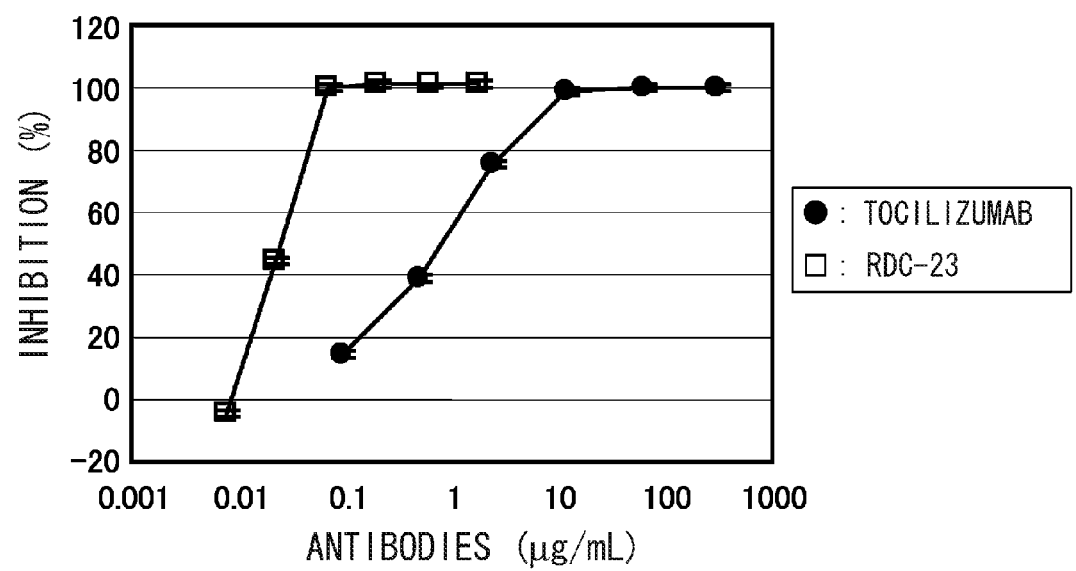

(b) a polypeptide that comprises CDR1 comprising the sequence of SEQ ID NO: 4 (CDR1 of VH3-M73), CDR2 comprising the sequence of SEQ ID NO: 5 (CDR2 of VH3-M73), and CDR3 comprising the sequence of SEQ ID NO: 6 (CDR3 of VH3-M73);

(c) a polypeptide that comprises CDR1 comprising the sequence of SEQ ID NO: 7 (CDR1 of VH5-M83), CDR2 comprising the sequence of SEQ ID NO: 8 (CDR2 of VH5-M83), and CDR3 comprising the sequence of SEQ ID NO: 9 (CDR3 of VH5-M83);

(d) a polypeptide that comprises CDR1 comprising the sequence of SEQ ID NO: 10 (CDR1 of VL1), CDR2 comprising the sequence of SEQ ID NO: 11 (CDR2 of VL1), and CDR3 comprising the sequence of SEQ ID NO: 12 (CDR3 of VL1);

(e) a polypeptide that comprises CDR1 comprising the sequence of SEQ ID NO: 13 (CDR1 of VL3), CDR2 comprising the sequence of SEQ ID NO: 14 (CDR2 of VL3), and CDR3 comprising the sequence of SEQ ID NO: 15 (CDR3 of VL3); and (f) a polypeptide that comprises CDR1 comprising the sequence of SEQ ID NO: 16 (CDR1 of VL5), CDR2 comprising the sequence of SEQ ID NO: 17 (CDR2 of VL5), and CDR3 comprising the sequence of SEQ ID NO: 18 (CDR3 of VL5).

The polypeptides of the present invention are not particularly limited; however, they are preferably antigen-binding substances having the activity of binding to human IL-6 receptor. Such antigen-binding substances preferably include, for example, antibody heavy chain variable regions (VH), antibody light chain variable regions (VL), antibody heavy chains, antibody light chains, and antibodies.

Of the polypeptides of (a) to (f) above, the polypeptides of (a) to (c) are preferable examples of antibody heavy chain variable regions, while the polypeptides of (d) to (f) are preferable examples of antibody light chain variable regions.

These variable regions can be used as a portion of an anti-human IL-6 receptor antibody. Anti-human IL-6 receptor antibodies in which such a variable region is used have superior binding activity, excellent pharmacokinetics, excellent safety, reduced immunogenicity, and/or superior physicochemical properties. In the present invention, excellent pharmacokinetics or improvement of pharmacokinetics refers to any one of: decrease in "clearance (CL)", increase in the "area under the curve (AUC)", increase in "mean residence time", and increase in "plasma half-life (t1/2)", which are pharmacokinetic parameters calculated from the time course of plasma concentration when an antibody is administered into the body. Herein, superior physicochemical property or improved physicochemical property refers to, but is not limited to, improved stability, decreased heterogeneity, or the like.

Human antibody framework regions (FRs) to be linked with CDR are selected so that the CDR forms a favorable antigen-binding site. FRs to be used for the variable regions of the present invention are not particularly limited and any FR may be used; however, human-derived FRs are preferably used. It is possible to use human-derived FRs having a natural sequence. Alternatively, if needed, substitution, deletion, addition and/or insertion or such of one or more amino acids may be introduced into the framework region having a natural sequence so that the CDR forms an adequate antigen-binding site. Mutant FR sequences having a desired property can be selected, for example, by measuring and evaluating the binding activity to an antigen for an antibody with an FR with amino acid substitutions (Sato, K. et al., Cancer Res. (1993) 53, 851-856).

Moreover, one or more amino acids may be substituted, deleted, added, and/or inserted in the CDR sequence described above. It is preferred that a CDR sequence after substitution, deletion, addition, and/or insertion of one or more amino acids has equivalent activity to the CDR sequence before alteration with regard to binding activity, neutralizing activity, stability, immunogenicity, and/or pharmacokinetics. The number of amino acids to be substituted, deleted, added, and/or inserted is not particularly limited; however, it is preferably three amino acids or less, more preferably two amino acids or less, and still more preferably one amino acid per CDR.

Methods for substituting one or more amino acid residues with other amino acids of interest include, for example, site-directed mutagenesis (Hashimoto-Gotoh, T, Mizuno, T, Ogasahara, Y, and Nakagawa, M. (1995) An oligodeoxyribonucleotide-directed dual amber method for site-directed mutagenesis. Gene 152, 271-275; Zoller, M J, and Smith, M. (1983) Oligonucleotide-directed mutagenesis of DNA fragments cloned into M13 vectors. Methods Enzymol. 100, 468-500; Kramer, W, Drutsa, V, Jansen, H W, Kramer, B, Pflugfelder, M, and Fritz, H J (1984) The gapped duplex DNA approach to oligonucleotide-directed mutation construction. Nucleic Acids Res. 12, 9441-9456; Kramer W, and Fritz H J (1987) Oligonucleotide-directed construction of mutations via gapped duplex DNA Methods. Enzymol. 154, 350-367; Kunkel, T A (1985) Rapid and efficient site-specific mutagenesis without phenotypic selection. Proc Natl Acad Sci U.S.A. 82, 488-492). This method can be used to substitute desired amino acids in an antibody with other amino acids of interest. Furthermore, amino acids in the frameworks and CDRs can be substituted to other appropriate amino acids using library techniques such as framework shuffling (Mol. Immunol. 2007 April; 44(11): 3049-60) and CDR repair (US 2006/0122377).

The present invention also provides the antibodies of (a) to (c) below:

(a) an antibody which comprises a heavy chain variable region that comprises CDR1 comprising the sequence of SEQ ID NO: 1 (CDR1 of VH4-M73), CDR2 comprising the sequence of SEQ ID NO: 2 (CDR2 of VH4-M73), and CDR3 comprising the sequence of SEQ ID NO: 3 (CDR3 of VH4-M73), and a light chain variable region that comprises CDR1 comprising the sequence of SEQ ID NO: 10 (CDR1 of VL1), CDR2 comprising the sequence of SEQ ID NO: 11 (CDR2 of VL1), and CDR3 comprising the sequence of SEQ ID NO: 12 (CDR3 of VL1);

(b) an antibody which comprises a heavy chain variable region that comprises CDR1 comprising the sequence of SEQ ID NO: 4 (CDR1 of VH3-M73), CDR2 comprising the sequence of SEQ ID NO: 5 (CDR2 of VH3-M73), and CDR3 comprising the sequence of SEQ ID NO: 6 (CDR3 of VH3-M73), and a light chain variable region that comprises CDR1 comprising the sequence of SEQ ID NO: 13 (CDR1 of VL3), CDR2 comprising the sequence of SEQ ID NO: 14 (CDR2 of VL3), and CDR3 comprising the sequence of SEQ ID NO: 15 (CDR3 of VL3); and (c) an antibody which comprises a heavy chain variable region that comprises CDR1 comprising the sequence of SEQ ID NO: 7 (CDR1 of VH5-M83), CDR2 comprising the sequence of SEQ ID NO: 8 (CDR2 of VH5-M83), and CDR3 comprising the sequence of SEQ ID NO: 9 (CDR3 of VH5-M83), and a light chain variable region that comprises CDR1 comprising the sequence of SEQ ID NO: 16 (CDR1 of VL5), CDR2 comprising the sequence of SEQ ID NO: 17 (CDR2 of VL5), and CDR3 comprising the sequence of SEQ ID NO: 18 (CDR3 of VL5).

The antibodies described above can be used as anti-human IL-6 receptor antibodies having superior binding activity, excellent pharmacokinetics, excellent safety, reduced immunogenicity, and/or superior physicochemical properties.

Human antibody framework regions to be linked with CDR of the present invention are selected so that the CDR forms a favorable antigen-binding site. FRs to be used for the variable regions of the present invention are not particularly limited, and any FR may be used; however, human-derived FR is preferably used. It is possible to use human-derived FRs having a natural sequence. Alternatively, if needed, substitution, deletion, addition and/or insertion or such of one or more amino acids may be introduced into the framework region having a natural sequence so that the CDR forms an adequate antigen-binding site. Mutant FR sequences having a desired property can be selected, for example, by measuring and evaluating the binding activity to an antigen for an antibody having an FR with amino acid substitutions (Sato, K. et al., Cancer Res. (1993) 53, 851-856).

Meanwhile, the constant region to be used for an antibody of the present invention is not particularly limited, and any constant region may be used. Preferred constant regions to be used for the antibodies of the present invention include, for example, human-derived constant regions (constant regions derived from IgG1, IgG2, IgG3, IgG4, Cκ, Cλ, and such). One or more amino acids may be substituted, deleted, added, and/or inserted in the human-derived constant regions. The preferred human-derived heavy chain constant regions include, for example, constant regions comprising the amino acid sequence of SEQ ID NO: 31 (constant region of VH4-M73), constant regions comprising the amino acid sequence of SEQ ID NO: 32 (constant region VH3-M73)), and constant regions comprising the amino acid sequence of SEQ ID NO: 33 (constant region of VH5-M83), while the preferred human-derived light chain constant regions include, for example, constant regions comprising the amino acid sequence of SEQ ID NO: 34 (VL1), constant regions comprising the amino acid sequence of SEQ ID NO: 35 (VL3), and constant regions comprising the amino acid sequence of SEQ ID NO: 36 (VL5).

Moreover, one or more amino acids may be substituted, deleted, added, and/or inserted in the CDR sequence described above. It is preferred that a CDR sequence after substitution, deletion, addition, and/or insertion of one or more amino acids has equivalent activity to the CDR sequence before alteration with regard to binding activity, neutralizing activity, stability, immunogenicity, and/or pharmacokinetics. The number of amino acids to be substituted, deleted, added, and/or inserted is not particularly limited; however, it is preferably three amino acids or less, more preferably two amino acids or less, and still more preferably one amino acid per CDR.

Amino acids can also be substituted, deleted, added, and/or inserted by the methods described above.

The present invention also provides the variable regions of (a) to (f) below:
(a) a heavy chain variable region comprising the sequence of SEQ ID NO: 19 (variable region of VH4-M73);
(b) a heavy chain variable region comprising the sequence of SEQ ID NO: 20 (variable region of VH3-M73);
(c) a heavy chain variable region comprising the sequence of SEQ ID NO: 21 (variable region of VH5-M83);
(d) a light chain variable region comprising the sequence of SEQ ID NO: 22 (variable region of VL1);
(e) a light chain variable region comprising the sequence of SEQ ID NO: 23 (variable region of VL3); and
(f) a light chain variable region comprising the sequence of SEQ ID NO: 24 (variable region of VL5).

The variable regions described above can be used as part of an anti-human IL-6 receptor antibody. Anti-human IL-6 receptor antibodies in which such variable regions are used have superior binding activity, excellent pharmacokinetics, excellent safety, reduced immunogenicity, and/or superior physicochemical properties.

The variable regions described above may also comprise substitutions, deletions, additions, and/or insertions of one or more amino acids (for example, five amino acids or less, preferably three amino acids or less). Methods for substituting one or more amino acid residues with other amino acids of interest include, for example, the methods described above.

The present invention also provides polypeptides comprising the variable regions described above.

Furthermore, the present invention provides the antibodies of (a) to (c) below:
(a) an antibody that comprises a heavy chain variable region comprising the sequence of SEQ ID NO: 19 (variable region of VH4-M73) and a light chain variable region comprising the sequence of SEQ ID NO: 22 (variable region of VL1);
(b) an antibody that comprises a heavy chain variable region comprising the sequence of SEQ ID NO: 20 (variable region of VH3-M73) and a light chain variable region comprising the sequence of SEQ ID NO: 23 (variable region of VL3); and
(c) an antibody that comprises a heavy chain variable region comprising the sequence of SEQ ID NO: 21 (variable region of VH5-M83) and a light chain variable region comprising the sequence of SEQ ID NO: 24 (variable region of VL5).

The variable regions described above can be used as part of an anti-human IL-6 receptor antibody. Anti-human IL-6 receptor antibodies in which these variable regions are used have superior binding activity, excellent pharmacokinetics, excellent safety, reduced immunogenicity, and/or superior physical properties.

The variable regions described above may also comprise substitutions, deletions, additions, and/or insertions of one or more amino acids (for example, five amino acids or less, preferably three amino acids or less). Methods for substituting one or more amino acid residues with other amino acids of interest include, for example, the methods described above.

Meanwhile, the constant region to be used for an antibody of the present invention is not particularly limited, and any constant region may be used. The preferred constant regions to be used for the antibodies of the present invention include, for example, human-derived constant regions (constant regions derived from IgG1, IgG2, IgG3, IgG4, κ chain, λ chain, and such). One or more amino acids may be substituted, deleted, added, and/or inserted in the human-derived constant regions. The preferred human-derived heavy chain constant regions include, for example, constant regions comprising the amino acid sequence of SEQ ID NO: 31 (constant region of VH4-M73), constant regions comprising the amino acid sequence of SEQ ID NO: 32 (constant region VH3-M73)), and constant regions comprising the amino acid sequence of SEQ ID NO: 33 (constant region of VH5-M83), while the preferred human-derived light chain constant regions include, for example, constant regions comprising the amino acid sequence of SEQ ID NO: 34 (VL1), constant regions comprising the amino acid sequence of SEQ ID NO: 35 (VL3), and constant regions comprising the amino acid sequence of SEQ ID NO: 36 (VL5).

The present invention also provides the heavy or light chains of (a) to (f) below:
 (a) a heavy chain comprising the sequence of SEQ ID NO: 25 (VH4-M73);
 (b) a heavy chain comprising the sequence of SEQ ID NO: 26 (VH3-M73);
 (c) a heavy chain comprising the sequence of SEQ ID NO: 27 (VH5-M83);
 (d) a light chain comprising the sequence of SEQ ID NO: 28 (VL1);
 (e) a light chain comprising the sequence of SEQ ID NO: 29 (VL3); and
 (f) a light chain comprising the sequence of SEQ ID NO: 30 (VL5).

The heavy chains and light chains described above can be used as part of an anti-human IL-6 receptor antibody. Anti-human IL-6 receptor antibodies in which these heavy chains and light chains are used have superior binding activity, excellent pharmacokinetics, excellent safety, reduced immunogenicity, and/or superior physicochemical properties.

The heavy chains and light chains described above may also comprise substitutions, deletions, additions, and/or insertions of one or more amino acids (for example, ten amino acids or less, preferably five amino acids or less, and more preferably three amino acids or less). Methods for substituting one or more amino acid residues with other amino acids of interest include, for example, the methods described above.

Substitutions, deletions, additions, and/or insertions of one or more amino acids may be carried out for the variable regions, constant regions, or both.

The present invention also provides the antibodies of (a) to (c) below:
 (a) an antibody that comprises a heavy chain comprising the sequence of SEQ ID NO: 25 (VH4-M73) and a light chain comprising the sequence of SEQ ID NO: 28 (VL1);
 (b) an antibody that comprises a heavy chain comprising the sequence of SEQ ID NO: 26 (VH3-M73) and a light chain comprising the sequence of SEQ ID NO: 29 (VL3); and
 (c) an antibody that comprises a heavy chain comprising the sequence of SEQ ID NO: 27 (VH5-M83) and a light chain comprising the sequence of SEQ ID NO: 30 (VL5).

The antibodies described above are anti-human IL-6 receptor antibodies that have superior binding activity, excellent pharmacokinetics, excellent safety, reduced immunogenicity, and/or superior physicochemical properties.

The antibodies described above may also comprise substitutions, deletions, additions, and/or insertions of one or more amino acids (for example, 20 amino acids or less, preferably ten amino acids or less, and more preferably five amino acids or less). Methods for substituting one or more amino acid residues with other amino acids of interest include, for example, the methods described above.

Substitutions, deletions, additions, and/or insertions of one or more amino acids may be carried out for the variable regions, constant regions, or both.

The antibodies of the present invention are preferably humanized antibodies.

Humanized antibodies are also referred to as reshaped human antibodies. Such a humanized antibody is obtained by grafting a complementary determining region (CDR) derived from a non-human mammal into the CDR of a human antibody. Conventional genetic recombination techniques for the preparation of such antibodies are also known (see European Patent Application No. EP 125023; and WO 96/02576).

Specifically, for example, a DNA sequence designed such that a CDR of interest and a framework region (FR) of interest are linked is synthesized by PCR, using several oligonucleotides prepared to have overlapping portions with the ends of both CDR and FR as primers (see the method described in WO 98/13388). A humanized antibody is obtained by: ligating the resulting DNA to a DNA that encodes a human antibody constant region or a modified human antibody constant region; inserting this into an expression vector; and introducing this into a host to produce the antibody (see European Patent Application No. EP 239400 and International Patent Application Publication No. WO 96/02576).

Human antibody framework regions to be linked with CDR are selected so that the CDR forms a favorable antigen-binding site. If needed, amino acid substitution, deletion, addition and/or insertion may be introduced into the framework region of an antibody variable region.

A human antibody constant region, or an altered human antibody constant region in which one or more amino acids have been substituted, deleted, added, and/or inserted in a human antibody constant region, can be used as the constant region of a humanized antibody.

For example, C$\gamma$1, C$\gamma$2, C$\gamma$3, C$\gamma$4, C$\mu$, C$\delta$, C$\alpha$1, C$\alpha$2, and C$\epsilon$ can be used for the H chain, and C$\kappa$ and C$\lambda$ can be used for the L chain. The amino acid sequence of C$\kappa$ is shown in SEQ ID NO: 38, and the nucleotide sequence encoding this amino acid sequence is shown in SEQ ID NO: 37. The amino acid sequence of C$\gamma$1 is shown in SEQ ID NO: 40, and the nucleotide sequence encoding this amino acid sequence is shown in SEQ ID NO: 39. The amino acid sequence of C$\gamma$2 is shown in SEQ ID NO: 42, and the nucleotide sequence encoding this amino acid sequence is shown in SEQ ID NO: 41. The amino acid sequence of C$\gamma$4 is shown in SEQ ID NO: 44, and the nucleotide sequence encoding this amino acid sequence is shown in SEQ ID NO: 43.

Furthermore, human antibody C regions may be modified to improve antibody stability or antibody production stability. Human antibodies of any isotype such as IgG, IgM, IgA, IgE, or IgD may be used in antibody humanization; however, IgG is preferably used in the present invention. IgG1, IgG2, IgG3, IgG4, or the like can be used as the IgG.

Amino acids in the variable region (for example, CDR and FR) and constant region of a humanized antibody may be deleted, added, inserted, and/or substituted with amino acids after preparation. The antibodies of the present invention also include such humanized antibodies comprising amino acid substitutions and the like.

The antibodies of the present invention include not only divalent antibodies as represented by IgG, but also monovalent antibodies and multivalent antibodies as represented by IgM, as long as they have IL-6 receptor-binding activity and/or neutralizing activity. The multivalent antibodies of the present invention include multivalent antibodies in which the antigen-binding sites are all identical, and multivalent antibodies in which all or some of the antigen-binding sites are different. The antibodies of the present invention include not only whole antibody molecules, but also minibodies and modified products thereof, as long as they bind to the IL-6 receptor protein.

Minibodies are antibodies comprising an antibody fragment lacking a portion of a whole antibody (for example, whole IgG or such), and are not particularly limited as long as they have IL-6 receptor-binding activity and/or neutralizing activity and comprise an antibody fragment that lacks a portion of a whole antibody (for example, whole IgG or such). The minibodies of the present invention are not particularly limited, as long as they comprise a portion of a whole antibody. However, the minibodies preferably comprise VH or VL, and particularly preferably comprise both VH and VL. Other preferable minibodies of the present invention include, for example, minibodies comprising antibody CDRs. The minibodies may comprise all or some of the six CDRs of an antibody.

The minibodies of the present invention preferably have a smaller molecular weight than whole antibodies. However, the minibodies may form multimers, for example, dimers, trimers, or tetramers, and thus their molecular weight is sometimes greater than that of whole antibodies.

Specifically, antibody fragments include, for example, Fab, Fab', F(ab')2, and Fv. Meanwhile, minibodies include, for example, Fab, Fab', F(ab')2, Fv, scFv (single chain Fv), diabodies, and sc(Fv)2 (single chain (Fv)2). Multimers (for example, dimers, trimers, tetramers, and polymers) of these antibodies are also included in the minibodies of the present invention.

Antibody fragments can be obtained, for example, by treating antibodies with enzymes to produce antibody fragments. Enzymes known to generate antibody fragments include, for example, papain, pepsin, and plasmin. Alternatively, a gene encoding such antibody fragment can be constructed, introduced into an expression vector, and expressed in appropriate host cells (see, for example, Co, M. S. et al., J. Immunol. (1994) 152, 2968-2976; Better, M. & Horwitz, A. H. Methods in Enzymology (1989) 178, 476-496; Pluckthun, A. & Skerra, A. Methods in Enzymology (1989) 178, 476-496; Lamoyi, E., Methods in Enzymology (1989) 121, 652-663; Rousseaux, J. et al., Methods in Enzymology (1989) 121, 663-669; Bird, R. E. et al., TIBTECH (1991) 9, 132-137).

Digestive enzymes cleave at specific sites of an antibody fragment, yielding antibody fragments of specific structures shown below. Genetic engineering techniques can be applied to such enzymatically-obtained antibody fragments to delete an arbitrary portion of the antibody.

Antibody fragments obtained by using the above digestive enzymes are as follows.
Papain digestion: F(ab)2 or Fab
Pepsin digestion: F(ab')2 or Fab'
Plasmin digestion: Facb The minibodies of the present invention include antibody fragments lacking an arbitrary region, as long as they have IL-6 receptor-binding activity and/or neutralizing activity.

"Diabody" refers to a bivalent antibody fragment constructed by gene fusion (Holliger P et al., 1993, Proc. Natl. Acad. Sci. USA 90: 6444-6448; EP 404,097; WO 93/11161, etc). Diabodies are dimers composed of two polypeptide chains. In each of the polypeptide chains forming a dimer, a VL and a VH are generally linked by a linker in the same chain. In general, a linker in a diabody is short enough such that the VL and VH cannot bind to each other. Specifically, the number of amino acid residues constituting the linker is, for example, about five residues. Thus, the VL and VH encoded on the same polypeptide cannot form a single-chain variable region fragment, and will form a dimer with another single-chain variable region fragment. As a result, the diabody has two antigen binding sites.

ScFv antibodies are single-chain polypeptides produced by linking VH and VL via a linker or such (Huston, J. S. et al., Proc. Natl. Acad. Sci. U.S.A. (1988) 85, 5879-5883; Pluckthun "The Pharmacology of Monoclonal Antibodies" Vol. 113, eds., Resenburg and Moore, Springer Verlag, New York, pp. 269-315, (1994)). The H-chain V region and L-chain V region of scFv may be derived from any antibody described herein. The peptide linker for linking the V regions is not particularly limited. For example, an arbitrary single-chain peptide containing about three to 25 residues can be used as the linker. Specifically, it is possible to use the peptide linkers described below or such.

The V regions of the two chains can be linked, for example, by PCR as described above. First, a DNA encoding the complete amino acid sequence or a desired partial amino acid sequence of one of the DNAs shown below is used as a template to link the V regions by PCR:
a DNA sequence encoding an H chain or H-chain V region of an antibody, and
a DNA sequence encoding an L chain or L-chain V region of an antibody.

DNAs encoding the V region of an H chain or L chain are amplified by PCR using a pair of primers containing corresponding sequences of the two ends of the DNA to be amplified. Then, a DNA encoding the peptide linker portion is prepared. The peptide linker-encoding DNA can also be synthesized by PCR. A nucleotide sequence that can be used to link the separately synthesized amplification products of V region is added to the 5' end of the primers to be used. Then, PCR is carried out using each of the DNAs in [H chain V region DNA]-[peptide linker DNA]-[L chain V region DNA] and assembly PCR primers.

The assembly PCR primers contain a combination of a primer that anneals with the 5' end of the [H chain V region DNA] and a primer that anneals with the 3' end of the [L chain V region DNA]. In other words, the assembly PCR primers are a set of primers that can be used to amplify DNAs encoding the full-length sequence of the scFv to be synthesized. Meanwhile, nucleic sequences that can be used to link each of the V-region DNAs are added to the [peptide linker DNA]. Then, these DNAs are linked, and then the whole scFv is ultimately generated as an amplification product using the assembly PCR primers. Once the scFv-encoding DNAs are generated, expression vectors containing these DNAs and recombinant cells transformed with these expression vectors can be obtained by conventional methods. Further, the scFv can be obtained through expression of the scFv-encoding DNAs by culturing the resulting recombinant cells.

The order of VH and VL to be linked is not particularly limited, and they may be arranged in any order. Examples of the arrangement are listed below.
[VH] linker [VL]
[VL] linker [VH]

sc(Fv)2 is a single-chain minibody produced by linking two VHs and two VLs using linkers and such (Hudson et al., 1999, J Immunol. Methods 231:177-189). sc(Fv)2 can be produced, for example, by linking scFv using a linker.

Preferably, the two VHs and two VLs of an antibody are arranged in the order of VH, VL, VH, and VL ([VH] linker [VL] linker [VH] linker [VL]) from the N terminus of the single-chain polypeptide; however, the order of the two VHs and two VLs is not limited to the above arrangement, and they may be arranged in any order. Examples of the arrangement are listed below:

[VL] linker [VH] linker [VH] linker [VL]
[VH] linker [VL] linker [VL] linker [VH]
[VH] linker [VH] linker [VL] linker [VL]
[VL] linker [VL] linker [VH] linker [VH]
[VL] linker [VH] linker [VL] linker [VH]

The amino acid sequence of the minibody VH or VL may contain substitutions, deletions, additions, and/or insertions. Furthermore, as long as VH and VL have antigen-binding activity when assembled, a portion may be deleted or other polypeptides may be added. Moreover, the variable regions may be chimerized or humanized.

In the present invention, linkers that can be used to link the antibody variable regions include arbitrary peptide linkers that can be introduced by genetic engineering, and synthetic linkers, for example, the linkers disclosed in Protein Engineering, (1996) 9(3), 299-305.

The preferred linkers in the present invention are peptide linkers. The length of the peptide linkers is not particularly limited and those skilled in the art can appropriately select the length according to the purpose. The typical length is one to 100 amino acids, preferably 3 to 50 amino acids, more preferably 5 to 30 amino acids, and particularly preferably 12 to 18 amino acids (for example, 15 amino acids).

For example, amino acid sequences for peptide linkers include the following sequences:

```
Ser

Gly·Ser

Gly·Gly·Ser

Ser·Gly·Gly

Gly·Gly·Gly·Ser (SEQ ID NO: 45)

Ser·Gly·Gly·Gly (SEQ ID NO: 46)

Gly·Gly·Gly·Gly·Ser (SEQ ID NO: 47)

Ser·Gly·Gly·Gly·Gly (SEQ ID NO: 48)

Gly·Gly·Gly·Gly·Gly·Ser (SEQ ID NO: 49)

Ser·Gly·Gly·Gly·Gly·Gly (SEQ ID NO: 50)

Gly·Gly·Gly·Gly·Gly·Gly·Ser (SEQ ID NO: 51)

Ser·Gly·Gly·Gly·Gly·Gly·Gly (SEQ ID NO: 52)

(Gly·Gly·Gly·Gly·Ser [SEQ ID NO: 47])n (Ser·Gly·Gly·Gly·Gly [SEQ ID NO: 48])n
``` where n is an integer of 1 or more.

The amino acid sequences of peptide linkers can be appropriately selected by those skilled in the art according to the purpose. For example, the above "n" which determines the length of the peptide linker is typically one to five, preferably one to three, and more preferably one or two.

Synthetic linkers (chemical crosslinking agents) include, crosslinking agents routinely used to crosslink peptides, for example, N-hydroxysuccinimide (NHS), disuccinimidyl suberate (DSS), bis(sulfosuccinimidyl)suberate (BS3), dithiobis(succinimidyl propionate) (DSP), dithiobis(sulfosuccinimidyl propionate) (DTSSP), ethylene glycol bis(succinimidyl succinate) (EGS), ethylene glycol bis(sulfosuccinimidyl succinate) (sulfo-EGS), disuccinimidyl tartarate (DST), disulfosuccinimidyl tartarate (sulfo-DST), bis[2-(succinimidooxycarbonyloxy)ethyl]sulfone (BSOCOES), and bis[2-(sulfosuccinimidooxycarbonyloxy)ethyl]sulfone (sulfo-BSOCOES). These crosslinking agents are commercially available.

In general, three linkers are required to link four antibody variable regions. These multiple linkers may be the same or different linkers.

The antibodies of the present invention also include antibodies in which one or more amino acid residues have been added to the amino acid sequence of an antibody of the present invention. Furthermore, the antibodies of the present invention also include fusion proteins in which an above-described antibody is fused with another peptide or protein. The fusion protein can be prepared by ligating a polynucleotide encoding an antibody of the present invention and a polynucleotide encoding another peptide or polypeptide in frame, introducing this into an expression vector, and expressing this in a host. Techniques known to those skilled in the art can be used. The peptide or polypeptide to be fused with an antibody of the present invention may be a known peptide, for example, FLAG (Hopp, T. P. et al., BioTechnology 6, 1204-1210 (1988)), 6×His consisting of six His (histidine) residues, 10×His, influenza hemagglutinin (HA), human c-myc fragment, VSV-GP fragment, p18HIV fragment, T7-tag, HSV-tag, E-tag, SV40 T antigen fragment, lck tag, α-tubulin fragment, B-tag, and Protein C fragment. Polypeptides to be fused with the antibodies of the present invention include, for example, GST (glutathione-S-transferase), HA (influenza hemagglutinin), immunoglobulin constant region, β-galactosidase, and MBP (maltose-binding protein). Commercially available polynucleotides encoding these peptides or polypeptides can be fused with a polynucleotide encoding an antibody of the present invention. A fusion polypeptide can be prepared by expressing the fusion polynucleotide thus prepared.

Moreover, the antibodies of the present invention may also be conjugated antibodies linked to various molecules such as polymers, including polyethylene glycol (PEG) and hyaluronic acid; radioactive substances; fluorescent substances; luminescent substances; enzymes; and toxins. Such conjugated antibodies can be obtained by chemically modifying the obtained antibodies. Methods for antibody modification are already established in the art (see, for example, U.S. Pat. Nos. 5,057,313 and 5,156,840). The "antibodies" of the present invention also include such conjugated antibodies.

Furthermore, the antibodies of the present invention include antibodies with altered sugar chains.

Furthermore, the antibodies used in the present invention may be bispecific antibodies. Bispecific antibody refers to an antibody that has variable regions that recognize different epitopes in the same antibody molecule. A bispecific antibody of the present invention may be a bispecific antibody that recognizes different epitopes on the IL-6 receptor molecule, or a bispecific antibody in which one of the antigen-binding sites recognizes the IL-6 receptor and the other antigen-binding site recognizes another substance. Examples of antigens that bind to the other antigen-binding site of a bispecific antibody that comprises an IL-6 receptor-recognizing antibody of the present invention include IL-6, TNFα, TNFR1, TNFR2, CD80, CD86, CD28, CD20, CD19, IL-1α, IL-β, IL-1R, RANKL, RANK, IL-17, IL-17R, IL-23, IL-23R, IL-15, IL-15R, BlyS, lymphotoxin α, lymphotoxin β, LIGHT ligand, LIGHT, VLA-4, CD25, IL-12, IL-12R, CD40, CD40L, BAFF, CD52, CD22, IL-32, IL-21, IL-21R, GM-CSF, GM-CSFR, M-CSF, M-CSFR, IFN-alpha, VEGF, VEGFR, EGF, EGFR, CCRS, APRIL, and APRILR.

Methods for producing bispecific antibodies are known. Bispecific antibodies can be prepared, for example, by linking two types of antibodies recognizing different antigens. Antibodies to be linked may be a half molecule each containing an H chain and an L chain, or a quarter molecule containing only one H chain. Alternatively, fusion cells producing bispecific antibodies can be prepared by fusing hybridomas producing different monoclonal antibodies. Furthermore, bispecific antibodies can be produced by genetic engineering techniques.

As described below, the antibodies of the present invention may differ in amino acid sequence, molecular weight, isoelectric point, presence/absence of sugar chains, and conformation, depending on the purification method, or the cell or host used to produce the antibodies. However, as long as the antibody obtained is functionally equivalent to an antibody of the present invention, it is included in the present invention. For example, when an antibody of the present invention is expressed in prokaryotic cells, for example, *Escherichia coli*, a methionine residue is added to the N terminus of the original antibody amino acid sequence. Such antibodies are also included in the antibodies of the present invention.

Polypeptides of anti-IL-6 receptor antibodies and such of the present invention can be produced by methods known to those skilled in the art.

An anti-IL-6 receptor antibody can be prepared, for example, by genetic recombination techniques known to those skilled in the art based on the sequence of the anti-IL-6 receptor antibody obtained. Specifically, an anti-IL-6 receptor antibody can be prepared by constructing a polynucleotide encoding the antibody based on the sequence of an IL-6 receptor-recognizing antibody, inserting the polynucleotide into an expression vector, and then expressing it in an appropriate host cell (see for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137).

Thus, the present invention provides methods of producing (i) a polypeptide of the present invention, or (ii) a polypeptide encoded by a gene encoding the polypeptide of the present invention, wherein the methods comprise the step of culturing a host cell comprising a vector into which a polynucleotide encoding the polypeptide of the present invention is introduced.

More specifically, the present invention provides methods of producing a polypeptide of the present invention, which comprise the steps of:

(a) culturing a host cell comprising a vector into which a gene encoding the polypeptide of the present invention is introduced; and (b) obtaining the polypeptide encoded by the gene.

Examples of the vector include M13-type vectors, pUC-type vectors, pBR322, pBluescript, and pCR-Script. Alternatively, when the objective is to subclone and excise the cDNA, other examples of the vector in addition to the ones described above include pGEM-T, pDIRECT, and pT7. Expression vectors are particularly useful for producing antibodies of the present invention. For example, when the expression vector is used for expression in *E. coli*, the vector should have features that allow its amplification in *E. coli*. In addition, when the host is *E. coli* such as JM109, DH5α, HB101, or XL1-Blue, it is essential that the vector carries a promoter that allows its efficient expression in *E. coli*, for example, lacZ promoter (Ward et al., Nature (1989) 341, 544-546; FASEB J. (1992) 6, 2422-2427), araB promoter (Better et al., Science (1988) 240, 1041-1043), T7 promoter or such. Such vector includes pGEX-5X-1 (Pharmacia), "QIAexpress system" (Quiagen), pEGFP, and pET (in this case, the host is preferably BL21 which expresses T7 RNA polymerase), in addition to the ones described above.

Furthermore, the expression plasmid vectors may contain signal sequences for antibody secretion. As a signal sequence for antibody secretion, the pelB signal sequence (Lei, S. P. et al., J. Bacteriol. (1987) 169, 4379) may be used for production into the *E. coli* periplasm. The vectors can be introduced into host cells, for example, by calcium chloride methods or electroporation.

In addition to vectors for *E. coli*, the vectors for producing antibodies of the present invention include, for example, mammal-derived expression vectors (for example, pcDNA3 (Invitrogen), pEF-BOS (Nucleic Acids. Res. (1990) 18(17), p5322), pEF, and pCDM8), insect cell-derived expression vectors (for example, the "Bac-to-BAC baculovirus expression system" (Gibco-BRL) and pBacPAK8), plant-derived expression vectors (for example, pMH1 and pMH2), animal virus-derived expression vectors (for example, pHSV, pMV, and pAdexLcw), retrovirus-derived expression vectors (for example, pZIPneo), yeast-derived expression vectors (for example, "*Pichia* Expression Kit" (Invitrogen), pNV11, and SP-Q01), and *Bacillus subtilis*-derived expression vectors (for example, pPL608 and pKTH50).

When the expression plasmid vector is used for expression in animal cells such as CHO, COS, and NIH3T3 cells, it must have a promoter necessary for expression in those cells, for example, SV40 promoter (Mulligan et al., Nature (1979) 277, 108), MMLV-LTR promoter, EF1α promoter (Mizushima et al., Nucleic Acids Res. (1990) 18, 5322), or CMV promoter. It is even more preferable if the vector has a gene for selection of transformed cells (for example, a drug resistance gene that allows distinction by an agent (neomycin, G418, or such). Vectors with such characteristics include, for example, pMAM, pDR2, pBK-RSV, pBK-CMV, pOPRSV, and pOP13.

In addition, when the objective is to stably express genes and amplify a gene's copy number in the cells, a method in which CHO cells deficient in a nucleic acid synthesis pathway are introduced with a vector having a DHFR gene which compensates for the deficiency (for example, pSV2-dhfr ("Molecular Cloning 2nd edition" Cold Spring Harbor Laboratory Press, (1989))) and the vector is amplified using methotrexate (MTX) can be used. Further, when the objective is transient gene expression, a method in which COS cells carrying a gene expressing the SV40 T antigen on their chromosome are transformed with a vector carrying an SV40 replication origin (pcD and such) can be used. It is possible to use replication origins derived from polyoma virus, adenovirus, bovine papilloma virus (BPV), and such. Moreover, to amplify the gene copy number in host cell lines, the expression vectors may comprise the aminoglycoside transferase (APH) gene, thymidine kinase (TK) gene, *E. coli* xanthine-guanine phosphoribosyltransferase (Ecogpt) gene, dihydrofolate reductase (dhfr) gene, and such as a selection marker.

The resulting antibodies of the present invention can be isolated from host cells or from outside the cells (the medium, or such), and purified as substantially pure and homogenous antibodies. The antibodies can be separated and purified using conventional separation and purification methods for antibody purification, without being limited thereto. For example, the antibodies can be separated and purified by appropriately selecting and combining column chromatography, filtration, ultrafiltration, salting out, solvent precipitation, solvent extraction, distillation, immunoprecipitation, SDS-polyacrylamide gel electrophoresis, isoelectrofocusing, dialysis, recrystallization, and such.

Chromatography includes, for example, affinity chromatography, ion exchange chromatography, hydrophobic chromatography, gel filtration, reverse phase chromatography, and adsorption chromatography (Strategies for Protein Purification and Characterization: A Laboratory Course Manual. Ed Daniel R. Marshak et al., Cold Spring Harbor Laboratory Press, 1996). These chromatographies can be carried out using liquid-phase chromatography, for example, HPLC and FPLC. Columns used for affinity chromatography include protein A columns and protein G columns. Examples of columns using Protein A include Hyper D, POROS, and Sepharose FF (GE Amersham Biosciences). The present invention also includes antibodies highly purified using such purification methods.

The IL-6 receptor binding activity of the obtained antibodies can be measured by methods known to those skilled in the art. Methods for measuring the antigen-binding activity of an antibody include, for example, enzyme-linked immunosorbent assay (ELISA), enzyme immunoassay (EIA), radioimmunoassay (RIA), and fluorescent antibody methods. For example, when enzyme immunoassay is used, antibody-containing samples such as purified antibodies and culture supernatants of antibody-producing cells are added to antigen-coated plates. A secondary antibody labeled with an enzyme such as alkaline phosphatase is added, and the plates are incubated. After washing, an enzyme substrate such as p-nitrophenyl phosphate is added, and the absorbance is measured to evaluate the antigen-binding activity.

Pharmaceutical Compositions

The present invention also provides pharmaceutical compositions that comprise an above-described polypeptide as an active ingredient. The pharmaceutical compositions of the present invention can be used for IL-6-associated diseases such as rheumatoid arthritis. Thus, the present invention also provides agents for treating diseases such as rheumatoid arthritis, which comprise an antibody described above as an active ingredient. Preferred examples of target diseases in the present invention include, but are not limited to, rheumatoid arthritis, juvenile idiopathic arthritis, systemic juvenile idiopathic arthritis, Castleman's disease, systemic lupus erythematosus (SLE), lupus nephritis, Crohn's disease, lymphoma, ulcerative colitis, anemia, vasculitis, Kawasaki disease, Still's disease, amyloidosis, multiple sclerosis, transplantation, age-related macular degeneration, ankylosing spondylitis, psoriasis, psoriatic arthritis, chronic obstructive pulmonary disease (COPD), IgA nephropathy, osteoarthritis, asthma, diabetic nephropathy, GVHD, endometriosis, hepatitis (NASH), myocardial infarction, arteriosclerosis, sepsis, osteoporosis, diabetes, multiple myeloma, prostate cancer, kidney cancer, B-cell non-Hodgkin's lymphoma, pancreatic cancer, lung cancer, esophageal cancer, colon cancer, cancer cachexia, cancer neuroinvasion, myocardial infarction, myopic choroidal neovascularization, idiopathic choroidal neovascularization, uveitis, chronic thyroiditis, delayed hypersensitivity, contact dermatitis, atopic dermatitis, mesothelioma, polymyositis, dermatomyositis, panuveitis, anterior uveitis, intermediate uveitis, scleritis, keratitis, orbital inflammation, optic neuritis, diabetic retinopathy, proliferative vitreoretinopathy, dry eye, and post-operative inflammation.

The phrase "to comprise an anti-IL-6 receptor antibody as an active ingredient" means comprising an anti-IL-6 receptor antibody as at least one of the active ingredients, without particular limitation on its content. Furthermore, the pharmaceutical compositions of the present invention may contain other active ingredients in combination with the polypeptides described above.

The pharmaceutical compositions of the present invention may be used not only for therapeutic purposes, but also for preventive purposes.

The polypeptides of the present invention can be formulated according to conventional methods (see, for example, Remington's Pharmaceutical Science, latest edition, Mark Publishing Company, Easton, USA). If needed, they may contain pharmaceutically acceptable carriers and/or additives. For example, they may include detergents (for example, PEG and Tween), excipients, antioxidants (for example, ascorbic acid), coloring agents, flavoring agents, preservatives, stabilizers, buffering agents (for example, phosphoric acid, citric acid, and other organic acids), chelating agents (for example, EDTA), suspending agents, isotonizing agents, binders, disintegrants, lubricants, fluidity promoters, and corrigents. However, the agents of the present invention for preventing or treating inflammatory diseases are not limited to the above and may appropriately contain other conventional carriers. Specifically, examples include light anhydrous silicic acid, lactose, crystalline cellulose, mannitol, starch, carmellose calcium, carmellose sodium, hydroxypropylcellulose, hydroxypropyl methylcellulose, polyvinyl acetal diethylaminoacetate, polyvinylpyrrolidone, gelatin, medium chain fatty acid triglyceride, polyoxyethylene hydrogenated castor oil 60, saccharose, carboxymethylcellulose, corn starch, and inorganic salts. They may also contain other low-molecular-weight polypeptides; proteins such as serum albumin, gelatin, and immunoglobulin; and amino acids. When preparing aqueous solutions for injection, the anti-IL-6 receptor antibodies are dissolved, for example, in isotonic solutions containing physiological saline, glucose, or other adjuvants. Adjuvants include, for example, D-sorbitol, D-mannose, D-mannitol, and sodium chloride. Furthermore, appropriate solubilizing agents, for example, alcohol (ethanol, and the like), polyalcohol (propylene glycol, PEG, and the like), and non-ionic surfactants (polysorbate 80 and HCO-50) may be combined.

If necessary, the polypeptides may be encapsulated in microcapsules (microcapsules made of hydroxycellulose, gelatin, poly(methyl methacrylate), and the like), or made into a colloidal drug delivery system (liposomes, albumin microspheres, microemulsions, nanoparticles, nanocapsules, etc) (see, for example, "Remington's Pharmaceutical Science 16th edition", Oslo Ed. (1980)). Moreover, methods for preparing agents as sustained-release agents are known, and these can be applied to the polypeptides (Langer et al., J. Biomed. Mater. Res. (1981) 15: 167-277; Langer, Chem. Tech. (1982) 12: 98-105; U.S. Pat. No. 3,773,919; European Patent Application (EP) No. 58,481; Sidman et al., Biopolymers (1983) 22:547-56; EP No. 133,988). Furthermore, liquid volume for subcutaneous administration can be increased by adding or mixing hyaluronidase to an agent (for example, see WO 2004/078140).

The pharmaceutical compositions of the present invention can be administered both orally and parenterally, but are preferably administered parenterally. Specifically, the compositions are administered to patients by injection or transdermally. Injections include, for example, systemic and local administrations by intravenous, intramuscular, or subcutaneous injection, or such. The compositions may be locally injected at the site of treatment or in the periphery of the site by intramuscular injection, in particular. Transdermal dosage forms include, for example, ointments, gel, cream, poultices, and patches, which can be administered locally or systemically. Furthermore, administration methods can be appropriately selected according to the patient's age and symptoms. The administered dose can be selected, for example, from the range of 0.0001 mg to 100 mg active ingredient per kg of body weight for each administration. Alternatively, when the compositions are administered to human patients, for example, the active ingredient can be selected from the range of 0.001 to 1000 mg per kg body weight for each patient. A single administration dose preferably contains, for example, an antibody of the present invention at about 0.01 to 50 mg/kg body weight. However, the dose of an antibody of the present invention is not limited to these doses.

Amino acids contained in the amino acid sequences in the present invention may be post-translationally modified (for example, the modification of an N-terminal glutamine into a pyroglutamic acid by pyroglutamylation is well-known to those skilled in the art). Naturally, such post-translationally modified amino acids are included in the amino acid sequences in the present invention.

Further, sugar chains that are bound to the antibodies according to the present invention may be of any structure. A sugar chain at position 297 (EU numbering) may be of any sugar chain structure (preferably a fucosylated sugar chain), or no sugar chain may be bound (for example, this can be achieved by producing antibodies in *Escherichia coli* or by introducing alteration so that no sugar chain binds to position 297, EU numbering).

All prior art references cited herein are incorporated by reference into this description.

EXAMPLES

Hereinbelow, the present invention will be specifically described with reference to the Examples, but it is not to be construed as being limited thereto.

Example 1

Identification of Mutation Sites in the Variable Regions for Enhancing the Affinity of TOCILIZUMAB for IL-6 Receptor A library of CDR sequences into which mutations have been introduced was constructed and assayed to improve the affinity of TOCILIZUMAB (H chain WT-IgG1/SEQ ID NO: 53; L chain WT-kappa/SEQ ID NO: 54) for IL-6 receptor. Screening of a library of CDR mutations revealed mutations that improve the affinity for IL-6 receptor. The mutations are shown in FIG. 1. A combination of these mutations yielded high-affinity TOCILIZUMAB such as RDC-23 (H chain RDC23H-IgG1/SEQ ID NO: 55; L chain RDC-23L-kappa/SEQ ID NO: 56). The affinity for soluble IL-6 receptor and biological activity determined using BaF/gp130 were compared between RDC-23 and TOCILIZUMAB (see Reference Examples for the method).

The result of affinity measurement is shown in Table 1. The result of biological activity determination using BaF/gp130 (the final concentration of IL-6 was 30 ng/ml) is shown in FIG. 2. The results showed that the affinity of RDC-23 was about 60 times higher, and the activity expressed as concentration for 100% inhibition of BaF/gp130 was about 100 times higher when compared to TOCILIZUMAB.

TABLE 1

|  | $k_a$ (1/Ms) | $k_d$ (1/s) | KD (M) |
| --- | --- | --- | --- |
| TOCILIZUMAB | 4.9E+05 | 2.0E−03 | 4.0E−09 |
| RDC-23 | 6.4E+05 | 4.3E−05 | 6.7E−11 |

Example 2

Identification of Mutations for Improving the Pharmacokinetics of TOCILIZUMAB Via Reduction of its Isoelectric Point To improve the pharmacokinetics of TOCILIZUMAB, investigation was carried out to identify mutation sites that would decrease the isoelectric point of the variable regions without significantly reducing the binding to the IL-6 receptor. Screening of mutation sites in the variable regions, which were predicted based on a three-dimensional structure model of TOCILIZUMAB, revealed mutation sites that would decrease the isoelectric point of the variable regions without significantly reducing its binding to the IL-6 receptor. These are shown in FIG. 3. A combination of these mutations yielded TOCILIZUMAB with reduced isoelectric point including, for example, H53/L28 (H chain H53-IgG1/SEQ ID NO: 57; L chain L28-kappa/SEQ ID NO: 58). The affinity for soluble IL-6 receptor, isoelectric point, pharmacokinetics in mice, and biological activity determined using BaF/gp130 were compared between H53/L28 and TOCILIZUMAB (see Reference Examples for the method).

Figure 4:
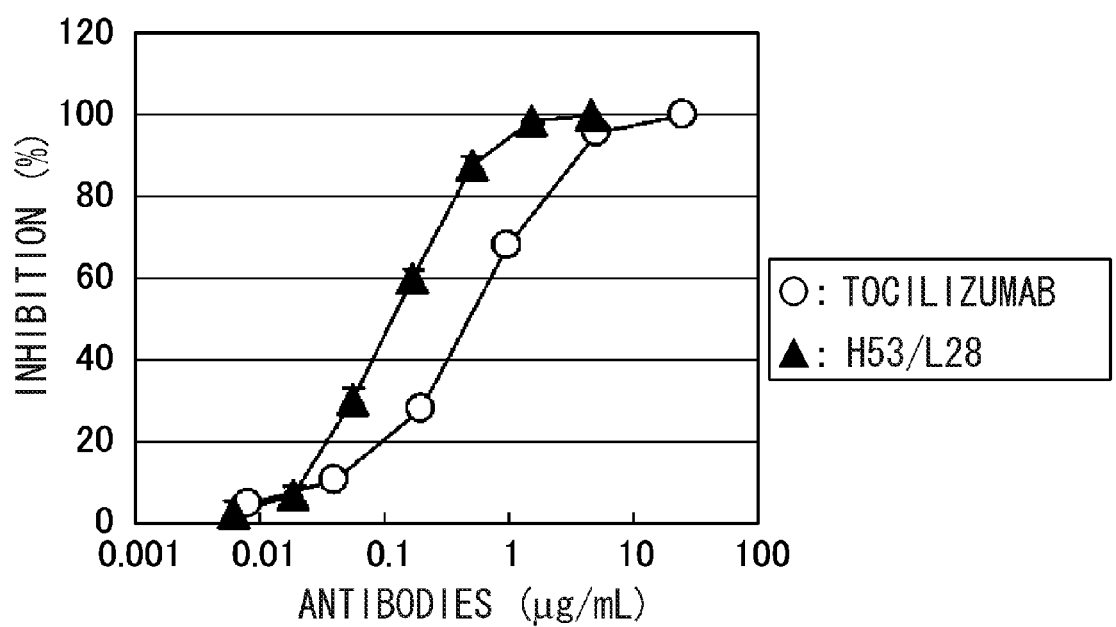

The result of affinity measurement is shown in Table 2. The measurement result for the biological activity obtained using BaF/gp130 (the final concentration of IL-6 was 30 ng/ml) is shown in FIG. 4. The results showed that the affinity of H53/L28 was about six times higher and the activity expressed as concentration for 100% inhibition of BaF/gp130 was about several times higher when compared to TOCILIZUMAB.

TABLE 2

|  | $k_a$ (1/Ms) | $k_d$ (1/s) | KD (M) |
| --- | --- | --- | --- |
| TOCILIZUMAB | 4.9E+05 | 2.0E−03 | 4.0E−09 |
| H53/L28 | 7.6E+05 | 5.2E−04 | 6.8E−10 |

The result of isoelectric point determination by isoelectric point electrophoresis known to those skilled in the art showed that the isoelectric points of TOCILIZUMAB and H53/L28 were about 9.3 and 6.5 to 6.7, respectively. Thus, the isoelectric point of H53/L28 was reduced by about 2.7 when compared to TOCILIZUMAB. Furthermore, the theoretical isoelectric point of the VH/VL variable regions was calculated using GENETYX (GENETYX CORPORATION). The result showed that the theoretical isoelectric points of TOCILIZUMAB and H53/L28 were 9.20 and 4.52, respectively. Thus, the isoelectric point of H53/L28 was reduced by about 4.7 when compared to TOCILIZUMAB.

Figure 5:
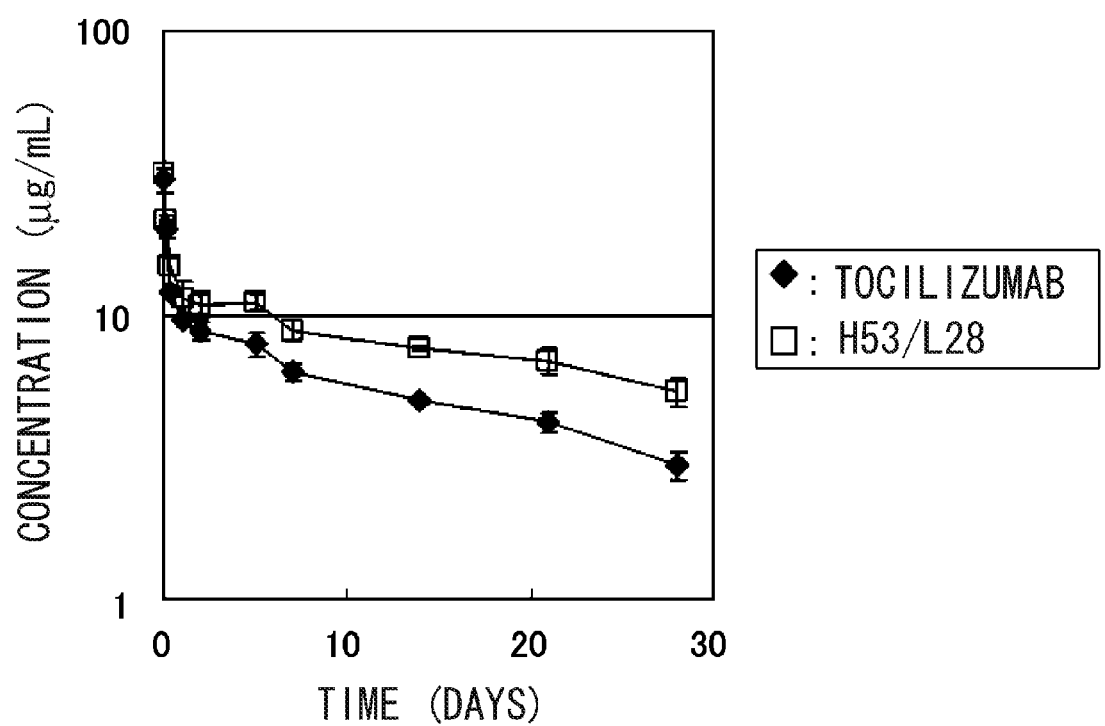
Figure 6:
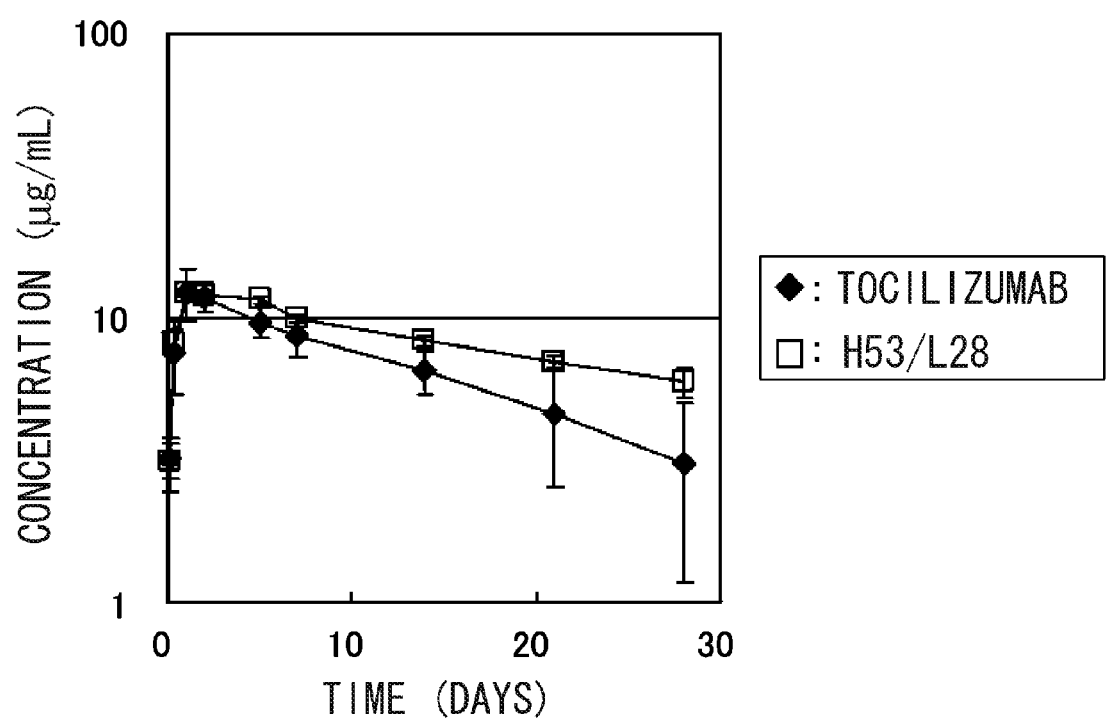

To assess the pharmacokinetics of the altered antibody H53/L28 which has a reduced isoelectric point, the pharmacokinetics of TOCILIZUMAB and H53/L28 in normal mice were compared. A single dose of TOCILIZUMAB or H53/L28 was intravenously (IV) or subcutaneously (SC)

administered at 1 mg/kg to mice (C57BL/6J; Charles River Japan, Inc.) to evaluate the time course of plasma concentration. The time courses of plasma concentration for TOCILIZUMAB and H53/L28 after intravenous administration or subcutaneous administration are shown in FIGS. 5 and 6, respectively. Pharmacokinetic parameters (clearance (CL) and half-life (T1/2)) obtained using WinNonlin (Pharsight) are shown in Table 3. The plasma half-life (T1/2) of H53/L28 after intravenous administration was prolonged to about 1.3 times that of TOCILIZUMAB, while the clearance was reduced by about 1.7 times. T1/2 of H53/L28 after subcutaneous administration was increased to about twice that of TOCILIZUMAB, while the clearance was reduced by about 2.1 times. Thus, it was found that the pharmacokinetics could be significantly improved by reducing the isoelectric point of TOCILIZUMAB through amino acid substitution.

TABLE 3

|  | IV | | SC | |
|---|---|---|---|---|
|  | CL mL/h/kg | T½ day | CL/F mL/h/kg | T½ day |
| TOCILIZUMAB | 0.177 | 18.5 | 0.18 | 14.7 |
| H53/L28 | 0.102 | 23.5 | 0.086 | 29.7 |

Example 3

Identification of Mutation Sites that Reduce the Immunogenicity of TOCILIZUMAB

Identification of Mutations that Reduce the Immunogenicity Risk of T-Cell Epitopes Present in the Variable Regions T-cell epitopes present in the variable-region sequence of TOCILIZUMAB were analyzed using TEPITOPE (Methods. 2004 December; 34(4):468-75). As a result, the L-chain CDR2 was predicted to have many T-cell epitopes that would bind to HLA (i.e. to have a sequence with a high immunogenicity risk). Thus, TEPITOPE analysis was carried out to examine amino acid substitutions that would reduce the immunogenicity risk of the L-chain CDR2 without decreasing the stability, binding activity, or neutralizing activity.

As described below, the screening result demonstrated that the immunogenicity risk can be reduced without decreasing the stability, binding activity, or neutralizing activity by substituting the threonine at L51 (Kabat's numbering; Kabat E A et al., (1991) Sequences of Proteins of Immunological Interest, NIH)) of the L chain CDR2 (SEQ ID NO: 59) of TOCILIZUMAB with glycine, and the arginine at L53 with glutamic acid (SEQ ID NO: 60).
TOCILIZUMAB L-chain CDR2 (SEQ ID NO: 59)
TOCILIZUMAB L-chain CDR2 with T-cell epitopes removed (SEQ ID NO: 60)

Example 4

Reduction of Immunogenicity Risk by Full Humanization of the Variable Region Framework Sequences of TOCILIZUMAB In the process of TOCILIZUMAB humanization, some mouse sequences remain in the framework sequence to maintain binding activity (Cancer Res. 1993 Feb. 15; 53(4): 851-6). These sequences are H27, H28, H29, and H30 in the H-chain FR1, and H71 in the H-chain FR3 (Kabat's numbering; Kabat E A et al., (1991) Sequences of Proteins of Immunological Interest, NIH)) of the variable region sequence of TOCILIZUMAB. The mouse sequences that remained are a potential cause of increased immunogenicity risk. Thus, it was assessed whether the framework sequence could be fully humanized to further reduce the immunogenicity risk of TOCILIZUMAB.

The result showed that the entire framework of TOCILIZUMAB could be completely humanized without decreasing the stability, binding activity, or neutralizing activity, by substituting the H-chain FR1 (SEQ ID NO: 61) of TOCILIZUMAB with the humanized H-chain FR1-A (SEQ ID NO: 62) shown below, and substituting the H chain FR3 (SEQ ID NO: 63) with the humanized H chain FR3 (SEQ ID NO: 64) shown below.
TOCILIZUMAB H chain FR1 (SEQ ID NO: 61)
Humanized H chain FR1-A (SEQ ID NO: 62) (derived from germline IMGT hVH_4)
TOCILIZUMAB H chain FR3 (SEQ ID NO: 63)
Humanized H chain FR3 (SEQ ID NO: 64) (derived from Mol. Immunol. 2007, 44(4):412-422)

Example 5

Identification of Mutation Sites to Improve the Pharmacokinetics Based on pH-Dependent Binding of TOCILIZUMAB to the IL-6 Receptor One of the methods for improving the pharmacokinetics of TOCILIZUMAB is to improve the molecule such that a single molecule of TOCILIZUMAB would repeatedly bind and neutralize several molecules of the IL-6 receptor. It is assumed that after binding to membrane-type IL-6 receptor, TOCILIZUMAB is taken up into intracellular endosomes via internalization while bound to membrane-type IL-6 receptor, then transferred into lysosomes while bound to membrane-type IL-6 receptor, and becomes degraded by lysosomes. Specifically, one molecule of TOCILIZUMAB typically binds to one or two molecules of membrane-type IL-6 receptor (in a monovalent or divalent manner) and is degraded in lysosomes after internalization. Therefore, one molecule of TOCILIZUMAB can only bind and neutralize one or two molecules of membrane-type IL-6 receptor.

Figure 7:
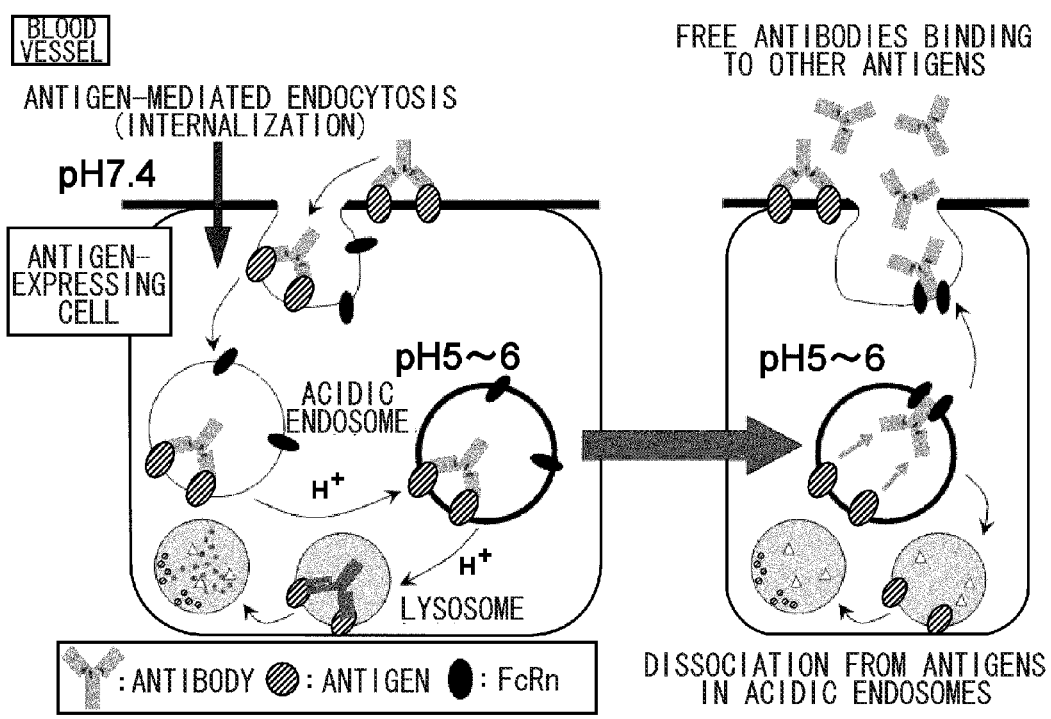
Figure 9:
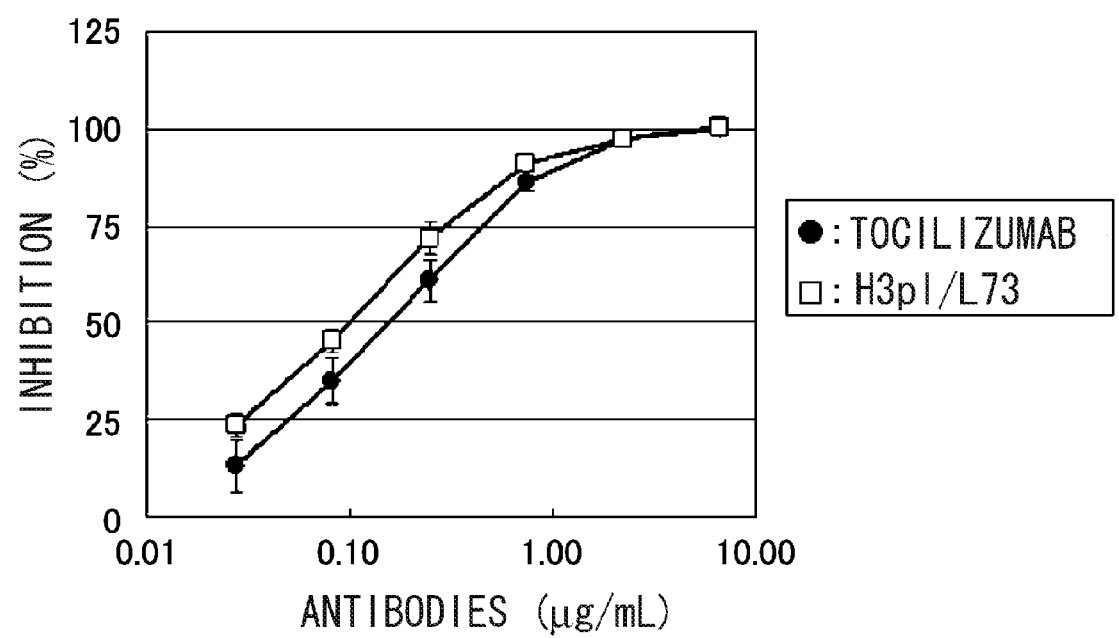
Figure 10:
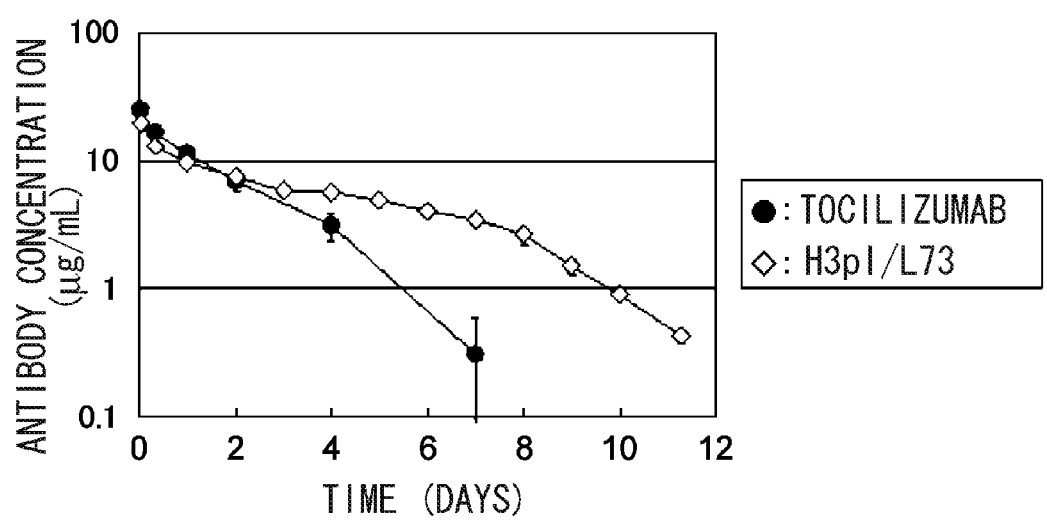
Figure 11:
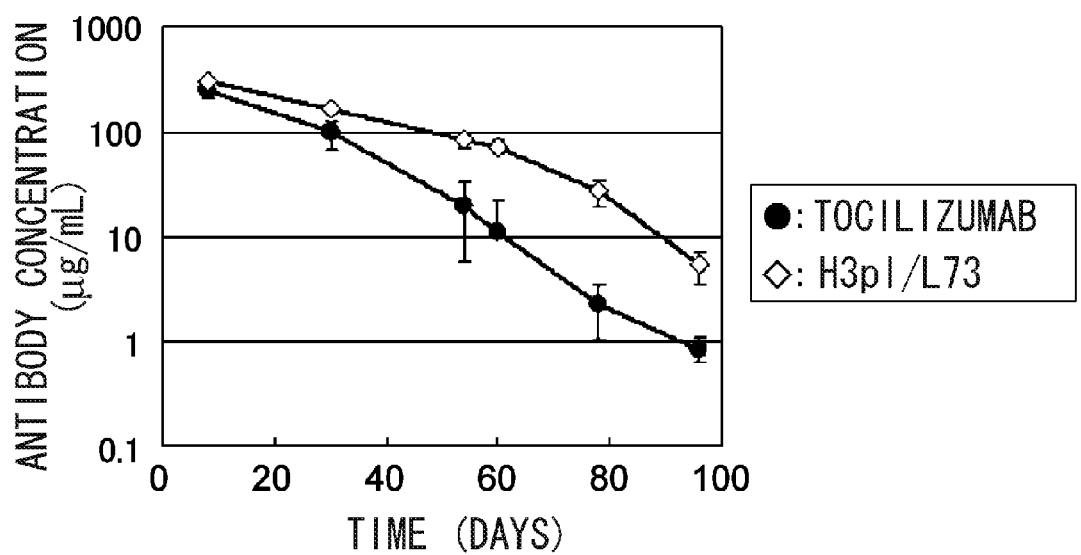

Thus, the present inventors thought that if it were possible to create TOCILIZUMAB that binds in a pH-dependent manner, in which the binding of TOCILIZUMAB is maintained under neutral conditions but significantly reduced under acidic conditions, TOCILIZUMAB which binds in a pH-dependent manner could dissociate from membrane-type IL-6 receptor (antigen) in the endosomes and return to the plasma by binding to FcRn present in the endosomes, as illustrated in FIG. 7. Once returned to the plasma, TOCILIZUMAB which binds in a pH-dependent manner could again bind to membrane-type IL-6 receptor. By repeating this binding in the plasma and dissociation in the endosomes, it is thought that one molecule of TOCILIZUMAB can repeatedly bind/neutralize several molecules of the IL-6 receptor. Thus, TOCILIZUMAB which binds in a pH-dependent manner is assumed to have improved pharmacokinetics as compared to TOCILIZUMAB.

For TOCILIZUMAB to dissociate from the IL-6 receptor under the acidic condition in the endosome, the binding must be significantly weakened under the acidic condition as compared to under the neutral condition. On the cell surface, strong IL-6 receptor binding is required for neutralization; therefore, at pH 7.4 which is the cell surface pH, the antibody must bind to the IL-6 receptor as strongly as or more strongly than TOCILIZUMAB. It has been reported that the endosomal pH is generally 5.5 to 6.0 (Nat Rev Mol Cell Biol. 2004 February; 5(2):121-32). Thus, if TOCILIZUMAB which binds in a pH-dependent manner is modified to weakly bind to the IL-6 receptor at pH 5.5 to 6.0, it can be predicted to dissociate from the IL-6 receptor under the acidic condition in the endosomes. Specifically, if TOCILIZUMAB which binds in a pH-dependent manner is improved to strongly bind to the IL-6 receptor at pH 7.4, which is the cell surface pH, and to weakly bind to IL-6 receptor at pH 5.5 to 6.0, which is the endosomal pH, one molecule of TOCILIZUMAB can bind and neutralize several molecules of the IL-6 receptor, and the pharmacokinetics can therefore be improved.

A possible method for conferring pH dependence on the binding of TOCILIZUMAB to the IL-6 receptor is to introduce histidine residues into the variable region of TOCILIZUMAB, since the pKa of a histidine residue is about 6.0 to 6.5, and its state of proton dissociation changes between neutral (pH 7.4) and acidic (pH 5.5 to 6.0) conditions. Thus, screening was carried out to identify sites for histidine introduction in the variable regions based on a three-dimensional structure model of TOCILIZUMAB. Furthermore, selected variable region sequences of TOCILIZUMAB were randomly substituted with histidine to design a library for screening. The screening was carried out using the binding to the IL-6 receptor at pH 7.4 and dissociation from the IL-6 receptor, or the reduction of affinity at pH 5.5 to 5.8 as an index.

As a result, the present inventors discovered mutation sites that confer the binding of TOCILIZUMAB to the IL-6 receptor with pH dependency (the property to bind at pH 7.4 and dissociate at pH 5.8). These are shown in FIG. 8. In FIG. 8, the substitution of tyrosine at H27 to histidine is a mutation in the H-chain FR1, not in the CDR. However, as described in Eur. J. Immunol. (1992) 22: 1719-1728, a sequence with histidine at H27 is a human sequence (SEQ ID NO: 65). Thus, the antibody can be completely humanized by using the following framework in combination with Example 4.

Humanized H-chain FR1-B (SEQ ID NO: 65)

A combination of mutations including, for example, H3pI/L73 (H chain H3pI-IgG1/SEQ ID NO: 66; L chain L73-kappa/SEQ ID NO: 67) can yield TOCILIZUMAB with pH-dependent binding properties. H3pI/L73 and TOCILIZUMAB were compared for their affinity towards soluble IL-6 receptor at pH 7.4, rate of dissociation from membrane-type IL-6 receptor at pH 7.4 and pH 5.8, biological activity using BaF/gp130, and pharmacokinetics in cynomolgus monkey and human IL-6 receptor transgenic mice (see Reference Examples for the method).

The result of affinity assay for soluble IL-6 receptor at pH 7.4 is shown in Table 4. The assay result for the biological activity obtained using BaF/gp130 (final IL-6 concentration of 30 ng/ml) is shown in FIG. 9. These results showed that H3pI/L73 is comparable to TOCILIZUMAB in terms of affinity for soluble IL-6 receptor at pH 7.4 and activity on BaF/gp130.

TABLE 4

| | $k_a$ (1/Ms) | $k_d$ (1/s) | KD (M) |
|---|---|---|---|
| TOCILIZUMAB | 5.1E+05 | 1.0E−03 | 2.1E−09 |
| H3pI/L73 | 5.4E+05 | 7.4E−04 | 1.4E−09 |

The measurement result for the rate of dissociation of TOCILIZUMAB or H3pI/L73 from membrane-type IL-6 receptor at pH 7.4 and pH 5.8 is shown in Table 5. As compared to TOCILIZUMAB, the dissociation rate of H3pI/L73 at pH 5.8 was faster and the pH dependence of the rate of dissociation from membrane-type IL-6 receptor was increased by about 2.6 times.

TABLE 5

| | pH 7.4 $k_d$ (1/s) | pH 5.8 $k_d$ (1/s) | $k_{d\ (pH\ 5.8)}/k_{d\ (pH\ 7.4)}$ pH DEPENDENCY |
|---|---|---|---|
| TOCILIZUMAB | 2.5E−04 | 2.5E−04 | 1.00 |
| H3pI/L73 | 2.6E−04 | 6.7E−04 | 2.59 |

A single dose of TOCILIZUMAB or H3pI/L73 was intravenously administered at 1 mg/kg to cynomolgus monkeys to assess the time course of plasma concentration. The plasma concentration time courses of TOCILIZUMAB or H3pI/L73 after intravenous administration are shown in FIG. 10. The result showed that the pharmacokinetics of H3pI/L73 in cynomolgus monkeys was significantly improved as compared to TOCILIZUMAB.

A single dose of TOCILIZUMAB or H3pI/L73 was intravenously administered at 25 mg/kg to human IL-6 receptor transgenic mice (hIL-6R tg mice; Proc Natl Acad Sci USA. 1995 May 23; 92(11):4862-6) to assess the time course of plasma concentration. The plasma concentration time courses of TOCILIZUMAB or H3pI/L73 after intravenous administration are shown in FIG. 11. The result showed that the pharmacokinetics of H3pI/L73 in human IL-6 receptor transgenic mice was significantly improved as compared to TOCILIZUMAB.

H3pI/L73, which is a TOCILIZUMAB with pH-dependent binding properties, showed significantly improved pharmacokinetics in cynomolgus monkeys and human IL-6 receptor transgenic mice when compared to TOCILIZUMAB. This suggests that it is possible to bind to and neutralize several molecules of the IL-6 receptor with one single molecule, by conferring the property of binding an antigen at pH 7.4 and dissociating from the antigen at pH 5.8. It was also considered that the pharmacokinetics could be further improved by conferring IL-6 receptor binding with a more pronounced pH dependence than that of H3pI/L73.

Example 6

Optimization of the TOCILIZUMAB Constant Region

Reduction of the Heterogeneity of TOCILIZUMAB H-Chain C Terminus

For heterogeneity of the H-chain C-terminal sequences of an IgG antibody, deletion of C-terminal amino acid lysine residue, and amidation of the C-terminal carboxyl group due to deletion of both of the two C-terminal amino acids, glycine and lysine, have been reported (Anal Biochem. 2007 Jan. 1; 360(1):75-83). Also in TOCILIZUMAB, the major component is a sequence in which the C-terminal amino acid lysine in the nucleotide sequence is deleted by post-translational modification; however, sub-components in which the lysine remains and sub-components in which the C-terminal carboxyl group is amidated due to deletion of both glycine and lysine also exist as heterogeneity. It is not easy and would be more costly to manufacture them as a pharmaceutical in large-scale while maintaining the objective substances/related substances related heterogeneity between productions. If possible, it is desirable to be single substances, and to have reduced heterogeneity when developing antibodies as pharmaceuticals. Thus, it is preferable that the H-chain C-terminal heterogeneity is absent when developing antibodies as pharmaceuticals.

Figure 12:
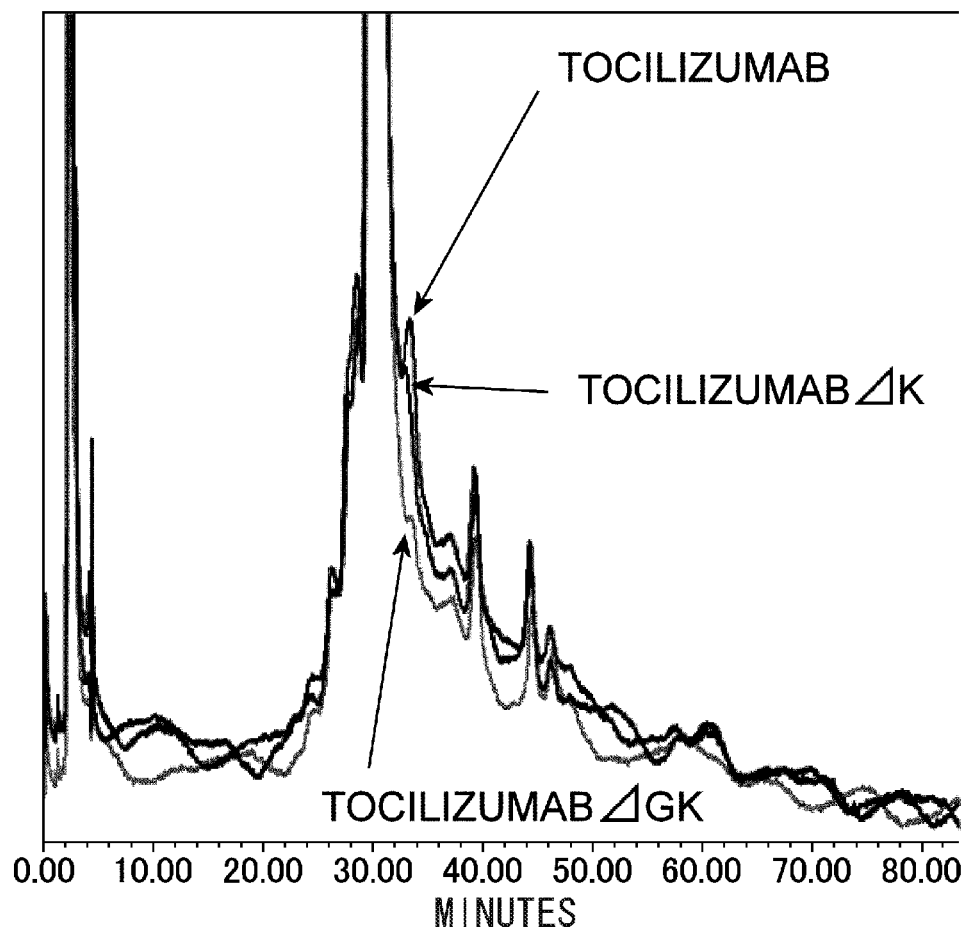

The C-terminal amino acid was altered to reduce the C-terminal amino acid heterogeneity. The result showed that the C-terminus-derived heterogeneity can be prevented by pre-deleting from the nucleotide sequence, the lysine and glycine residues at the C terminus of the H-chain constant region of TOCILIZUMAB. TOCILIZUMAB, TOCILIZUMAB that lacks the C-terminal lysine residue (TOCILIZUMABΔK: H chain WT-IgG1ΔK/SEQ ID NO: 68; L chain WT-kappa/SEQ ID NO: 54), and TOCILIZUMAB that lacks the C-terminal lysine and glycine residues (TOCILIZUMABΔGK: H chain WT-IgG1ΔGK/SEQ ID NO: 69; L chain WT-kappa/SEQ ID NO: 54) were assessed for heterogeneity by cation exchange chromatography. The ProPac WCX-10, 4×250 mm (Dionex) column was used; and mobile phase A was 25 mmol/L MES/NaOH (pH 6.1) and mobile phase B was 25 mmol/L MES/NaOH, 250 mmol/L NaCl (pH 6.1). Appropriate flow rate and gradient were used. The assessment result obtained by cation exchange chromatography is shown in FIG. 12. The result showed that the C-terminal amino acid heterogeneity can be reduced by pre-deleting from the nucleotide sequence both the lysine and glycine residues at the C terminus of the H-chain constant region, but not by pre-deleting only the lysine residue at the C terminus of the H-chain constant region. All of the C-terminal sequences of the constant region of human antibodies IgG1, IgG2, and IgG4 contain lysine and glycine at positions 447 and 446, respectively, according to EU numbering (see Sequences of proteins of immunological interest, NIH Publication No. 91-3242). Therefore, the method for reducing the C-terminal amino acid heterogeneity found in the present study is expected to be also applicable to IgG2 and IgG4 constant regions and variants thereof.

Reduction of Disulfide Bond-Derived Heterogeneity in IgG2 Isotype TOCILIZUMAB

The isotype of TOCILIZUMAB is IgG1. Since TOCILIZUMAB is a neutralizing antibody, binding to the Fcγ receptor can be unfavorable in view of immunogenicity and adverse effects. A possible method for lowering the Fcγ receptor binding is to convert the isotype of the IgG antibody from IgG1 to IgG2 or IgG4 (Ann Hematol. 1998 June; 76(6):231-48). From the viewpoint of Fcγ receptor I binding and pharmacokinetics, IgG2 was considered to be more desirable than IgG4 (Nat Biotechnol. 2007 December; 25(12):1369-72). Meanwhile, physicochemical properties of proteins, in particular, homogeneity and stability are very important when developing antibodies as pharmaceuticals. The IgG2 isotype has been reported to have very high heterogeneity due to the disulfide bonds in the hinge region (J Biol Chem. 2008 Jun. 6; 283(23):16206-15). It is not easy and would be more costly to manufacture them as pharmaceutical in large-scale while maintaining the objective substances/related substances related heterogeneity derived from disulfide bonds between productions. Thus, single substances are desirable as much as possible. Thus, when developing IgG2 isotype antibodies into pharmaceuticals, it is preferable to reduce the heterogeneity derived from disulfide bonds without lowering the stability.

Figure 13:
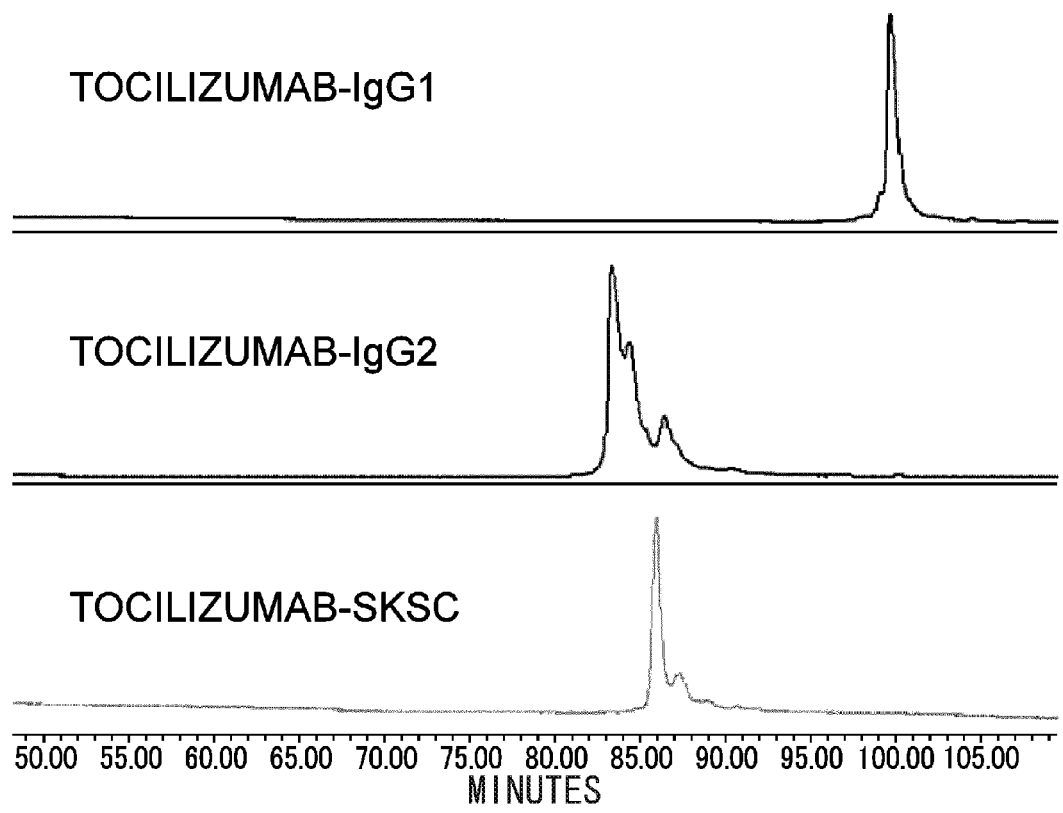
Figure 14:
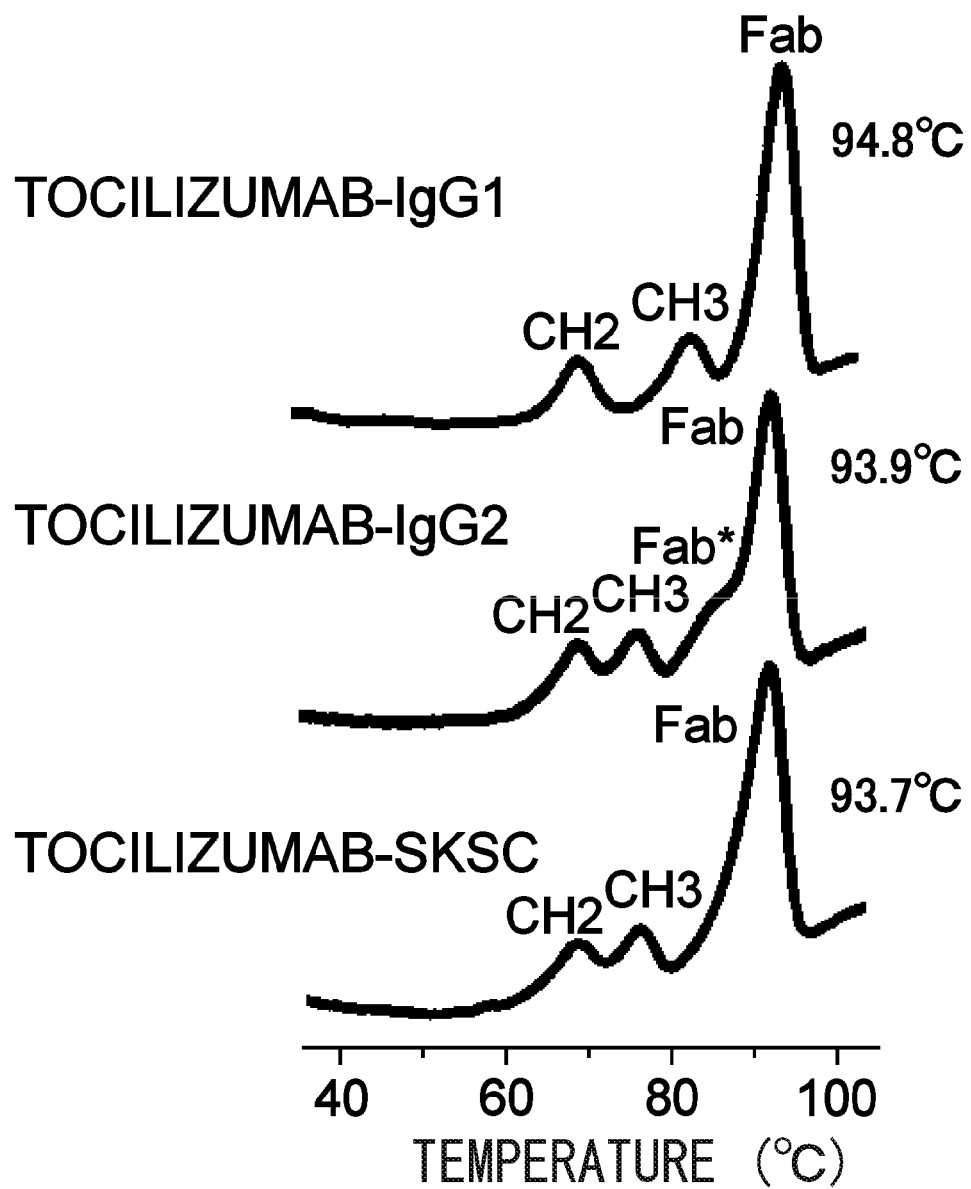

For the purpose of reducing the heterogeneity of the IgG2 isotype, various variants were assessed. As a result, it was found that heterogeneity could be reduced without decreasing the stability using the WT-SKSC constant region (SEQ ID NO: 70), in which of the IgG2 constant region sequences, the cysteine residue at position 131 and the arginine residue at position 133 (EU numbering) in the H-chain CH1 domain were substituted to serine and lysine, respectively, and the cysteine residue at position 219 (EU numbering) in the H-chain upper hinge was substituted to serine. TOCILIZUMAB-IgG1 (H chain WT-IgG1/SEQ ID NO: 53; L chain WT-kappa/SEQ ID NO: 54), TOCILIZUMAB-IgG2 (H chain WT-IgG2/SEQ ID NO: 71; L chain WT-kappa/SEQ ID NO: 54), and TOCILIZUMAB-SKSC (H chain WT-SKSC/SEQ ID NO: 70; L chain WT-kappa/SEQ ID NO: 54) were prepared and assessed for heterogeneity and stability. The heterogeneity was assessed by cation exchange chromatography. The ProPac WCX-10 (Dionex) column was used; and mobile phase A was 20 mM Sodium Acetate (pH 5.0) and mobile phase B was 20 mM Sodium Acetate, 1 M NaCl (pH 5.0). Appropriate flow rate and gradient were used. The assessment result obtained by cation exchange chromatography is shown in FIG. 13. The stability was assessed based on the intermediate temperature in thermal denaturation (Tm value) determined by differential scanning calorimetry (DSC) (VP-DSC; Microcal). The result of DSC measurement in 20 mM sodium acetate, 150 mM NaCl, pH 6.0 and the Tm value of the Fab domain are shown in FIG. 14.

The result showed that the heterogeneity was markedly increased in TOCILIZUMAB-IgG2 as compared to TOCILIZUMAB-IgG1; however, the heterogeneity could be significantly reduced by conversion to TOCILIZUMAB-SKSC. Furthermore, when compared to TOCILIZUMAB-IgG1, the DSC of TOCILIZUMAB-IgG2 gave a shoulder peak (Fab*) component with low stability, i.e., low Tm, in the thermal denaturation peaks of the Fab domain, which is assumed to be due to a heterogeneous component. However, when converted to TOCILIZUMAB-SKSC, the shoulder peak (low Tm), which is thought to be due to a heterogeneous component, disappeared, and the Tm value was about 94° C., which was equivalent to that of the Fab domain of TOCILIZUMAB-IgG1 and TOCILIZUMAB-IgG2. Thus, TOCILIZUMAB-SKSC was revealed to have high stability.

Identification of Pharmacokinetics-Improving Mutation Sites in the Constant Region of TOCILIZUMAB As described above, starting from IgG1, which is the isotype of TOCILIZUMAB, reduction of the C-terminal heterogeneity and reduction of heterogeneity of antibodies with IgG2 isotype constant regions while reducing the binding to the Fcγ receptor and maintaining the high stability can be achieved. Moreover, it is preferred that the constant region also has superior pharmacokinetics than IgG1, which is the isotype of TOCILIZUMAB.

In order to find constant regions having a superior plasma half-life than antibodies with IgG1-isotype constant regions, screening was carried out to identify mutation sites for improving the pharmacokinetics of TOCILIZUMAB-SKSC which has high stability and reduced heterogeneity related to antibodies with IgG2-isotype constant regions as mentioned above. As a result, WT-M58 (SEQ ID NO: 72 (amino acid sequence)) was discovered, in which, as compared to WT-SKSC, the glutamic acid at position 137, EU numbering is substituted to glycine, the serine at position 138 is substituted to glycine, the histidine at position 268 is substituted to glutamine, the arginine at position 355 is substituted to glutamine, the glutamine at position 419 is substituted to glutamic acid, and in which the glycine at position 446 and the lysine at position 447 is deleted to reduce the heterogeneity of the H-chain C terminus. In addition, WT-M44 (SEQ ID NO: 73 (amino acid sequence)) was prepared to have substitution of asparagine at position 434 to alanine, relative to IgG1. Furthermore, WT-M83 (SEQ ID NO: 74 (amino acid sequence)) was produced by deleting glycine at position 446 and lysine at position 447 from M44 to reduce the heterogeneity of the H-chain C-terminus. In addition, WT-M73 (SEQ ID NO: 75 (amino acid sequence)) was produced by substituting asparagine at position 434 with alanine in WT-M58.

TOCILIZUMAB-M44 (H chain WT-M44/SEQ ID NO: 73; L chain WT-kappa/SEQ ID NO: 54), TOCILIZUMAB-M58 (H chain WT-M58/SEQ ID NO: 72; L chain WT-kappa/SEQ ID NO: 54), and TOCILIZUMAB-M73 (H chain WT-M73/SEQ ID NO: 75; L chain WT-kappa/SEQ ID NO: 54) were prepared and assessed for their affinity towards human FcRn and pharmacokinetics using human FcRn transgenic mice (see Reference Examples for the method).

The binding of TOCILIZUMAB-IgG1, TOCILIZUMAB-M44, TOCILIZUMAB-M58, and TOCILIZUMAB-M73 to human FcRn was assessed using Biacore. As shown in Table 6, the binding of TOCILIZUMAB-M44, TOCILIZUMAB-M58, and TOCILIZUMAB-M73 was about 2.7 times, 1.4 times, and 3.8 times superior than that of TOCILIZUMAB-IgG1, respectively.

TABLE 6

|  | KD (µM) |
| --- | --- |
| TOCILIZUMAB-IgG1 | 1.62 |
| TOCILIZUMAB-M44 | 0.59 |
| TOCILIZUMAB-M58 | 1.17 |
| TOCILIZUMAB-M73 | 0.42 |

Figure 15:
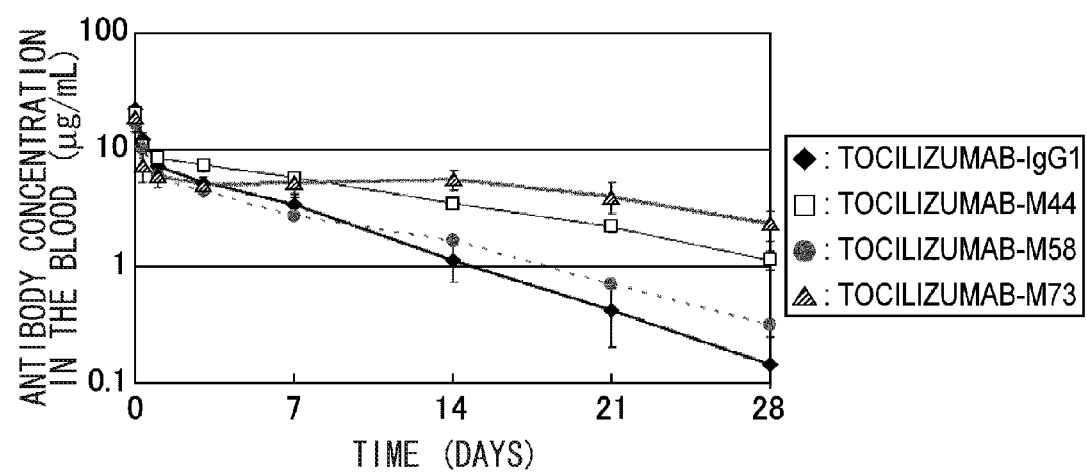

TOCILIZUMAB-IgG1, TOCILIZUMAB-M44, TOCILIZUMAB-M58, and TOCILIZUMAB-M73 were assessed for their pharmacokinetics in human FcRn transgenic mice. The result is shown in FIG. 15. When compared to TOCILIZUMAB-IgG1, all of TOCILIZUMAB-M44, TOCILIZUMAB-M58, and TOCILIZUMAB-M73 were found to exhibit improved pharmacokinetics, as shown in FIG. 15. The effect of improving the pharmacokinetics correlated with the ability to bind to human FcRn. In particular, the concentration of TOCILIZUMAB-M73 in plasma after 28 days was improved by about 16 times as compared to TOCILIZUMAB-IgG1. Thus, antibodies having the constant region of M73 were also assumed to have significantly improved pharmacokinetics in humans as compared to antibodies having the IgG1 constant region.

Example 7

Preparation of Fully Humanized IL-6 Receptor Antibodies with Improved PK/PD

TOCILIZUMAB variants were prepared by combining multiple mutations in the variable and constant regions of TOCILIZUMAB found in the examples above. Fully humanized IL-6 receptor antibodies discovered from various screenings were: Fv3-M73 (H chain VH4-M73/SEQ ID NO: 25; L chain VL1-kappa/SEQ ID NO: 28), Fv4-M73 (H chain VH3-M73/SEQ ID NO: 26; L chain VL3-kappa/SEQ ID NO: 29), and Fv5-M83 (H chain VH5-M83/SEQ ID NO: 27; L chain VL5-kappa/SEQ ID NO: 30).

Figure 16:
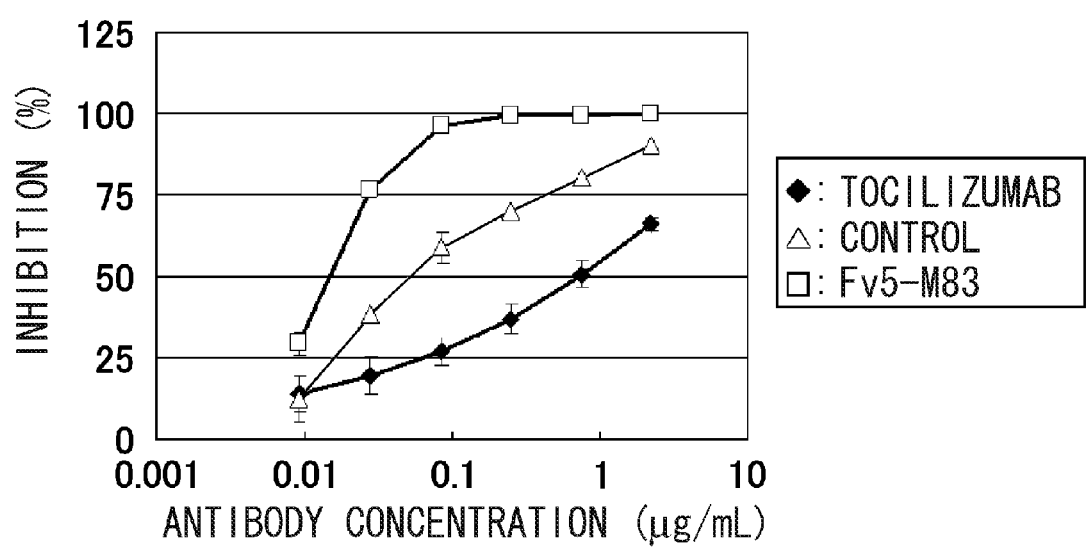
Figure 17:
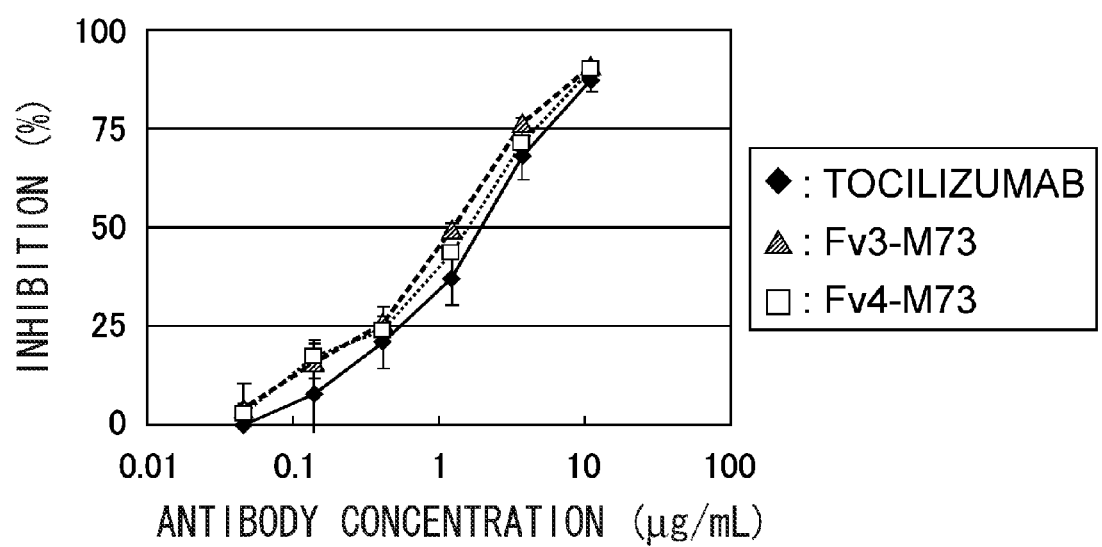

The affinities of prepared Fv3-M73, Fv4-M73, and Fv5-M83 against IL-6 receptor were compared to that of TOCILIZUMAB (see Reference Example for method). The affinities of these antibodies for the soluble IL-6 receptor determined at pH 7.4 are shown in Table 7. Furthermore, their BaF/gp130-neutralizing activities were compared to those of TOCILIZUMAB and the control (the known high affinity anti-IL-6 receptor antibody described in Reference Example, and VQ8F11-21 hIgG1 described in US 2007/0280945) (see Reference Example for method). The results obtained by determining the biological activities of these antibodies using BaF/gp130 are shown in FIG. 16 (TOCILIZUMAB, the control, and Fv5-M83 with a final IL-6 concentration of 300 ng/ml) and FIG. 17 (TOCILIZUMAB, Fv3-M73, and Fv4-M73 with a final IL-6 concentration of 30 ng/ml). As shown in Table 7, Fv3-M73 and Fv4-M73 have about two to three times higher affinity than TOCILIZUMAB, while Fv5-M83 exhibits about 100 times higher affinity than TOCILIZUMAB (since it was difficult to measure the affinity of Fv5-M83, instead the affinity was determined using Fv5-IgG1 (H chain VH5-IgG1/SEQ ID NO: 76; L chain VL5-kappa/SEQ ID NO: 30), which has an IgG1-type constant region; the constant region is generally thought to have no effect on affinity). As shown in FIG. 17, Fv3-M73 and Fv4-M73 exhibit slightly stronger activities than TOCILIZUMAB. As shown in FIG. 16, Fv5-M83 has a very strong activity, which is more than 100 times greater than that of TOCILIZUMAB in terms of 50% inhibitory concentration. Fv5-M83 also exhibits about 10 times higher neutralizing activity in terms of 50% inhibitory concentration than the control (the known high-affinity anti-IL-6 receptor antibody).

TABLE 7

|  | $k_a$ (1/Ms) | $k_d$ (1/s) | KD (M) |
| --- | --- | --- | --- |
| TOCILIZUMAB | 4.0E+05 | 1.1E−03 | 2.7E−09 |
| Fv3-M73 | 8.5E+05 | 8.7E−04 | 1.0E−09 |
| Fv4-M73 | 7.5E+05 | 1.0E−03 | 1.4E−09 |
| Fv5-M83 | 1.1E+06 | 2.8E−05 | 2.5E−11 |

The rates of dissociation of TOCILIZUMAB, Fv3-M73, and Fv4-M73 from membrane-type IL-6 receptor at pH 7.4 and 5.8 were determined. As demonstrated by the result shown in Table 8 (see Reference Example for method), the pH dependency of the dissociation rate of Fv3-M73 and Fv4-M73 from membrane-type IL-6 receptor was about 11 times and 10 times improved, respectively, as compared to TOCILIZUMAB. The considerable improvement of the pH dependency of the dissociation rate relative to H3pI/L73 described in Example 5 suggested that when compared to H3pI/L73, pharmacokinetics of Fv3-M73 and Fv4-M73 would be significantly improved.

TABLE 8

|  | pH 7.4 $k_d$ (1/s) | pH 5.8 $k_d$ (1/s) | $k_{d\,(pH\,5.8)}/k_{d\,(pH\,7.4)}$ pH DEPENDENCY |
| --- | --- | --- | --- |
| TOCILIZUMAB | 2.5E−04 | 2.5E−04 | 1.00 |
| Fv3-M73 | 4.9E−04 | 5.3E−03 | 10.88 |
| Fv4-M73 | 5.1E−04 | 5.1E−03 | 10.06 |

The isoelectric points of TOCILIZUMAB, the control, Fv3-M73, Fv4-M73, and Fv5-M83 were determined by isoelectric focusing electrophoresis using a method known to those skilled in the art. The result showed that the isoelectric point was about 9.3 for TOCILIZUMAB; about 8.4 to 8.5 for the control; about 5.7 to 5.8 for Fv3-M73; about 5.6 to 5.7 for Fv4-M73; and 5.4 to 5.5 for Fv5-M83. Thus, each antibody had a significantly lowered isoelectric point when compared to TOCILIZUMAB and the control.

Furthermore, the theoretical isoelectric point of the variable regions VH/VL was calculated by GENETYX (GENETYX CORPORATION). The result showed that the theoretical isoelectric point was 9.20 for TOCILIZUMAB; 7.79 for the control; 5.49 for Fv3-M73; 5.01 for Fv4-M73; and 4.27 for Fv5-M83. Thus, each antibody had a significantly lowered isoelectric point when compared to TOCILIZUMAB and the control. Since it was shown in Example 2 that pharmacokinetics is improved by reducing the isoelectric point, the pharmacokinetics of Fv3-M73, Fv4-M73, and Fv5-M83 was thought to be improved when compared to TOCILIZUMAB and the control.

T-cell epitopes in the variable region sequence of TOCILIZUMAB, Fv3-M73, Fv4-M73, or Fv5-M83 were analyzed using TEPITOPE (Methods. 2004 December; 34(4):468-75). As a result, TOCILIZUMAB was predicted to have T-cell epitopes, of which many could bind to HLA, as shown in Example 3. In contrast, the number of sequences that were predicted to bind to T-cell epitopes was significantly reduced in Fv3-M73, Fv4-M73, and Fv5-M83. In addition, the framework of Fv3-M73, Fv4-M73, or Fv5-M83 has no mouse sequence and is thus fully humanized. These suggest the possibility that immunogenicity risk is significantly reduced in Fv3-M73, Fv4-M73, and Fv5-M83 when compared to TOCILIZUMAB.

Example 8

PK/PD Test of Fully Humanized IL-6 Receptor Antibodies in Monkeys

Figure 18:
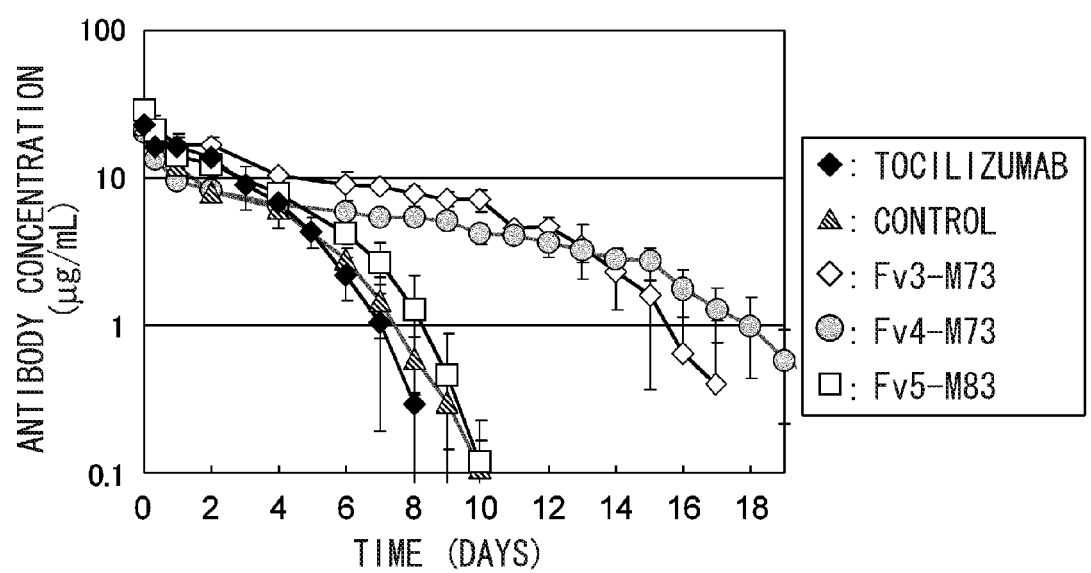

Each of TOCILIZUMAB, the control, Fv3-M73, Fv4-M73, and Fv5-M83 was intravenously administered once at a dose of 1 mg/kg to cynomolgus monkeys to assess their time course of plasma concentration (see Reference Example for method). The plasma concentration time courses of TOCILIZUMAB, Fv3-M73, Fv4-M73, and Fv5-M83 after intravenous administration are shown in FIG. 18. The result showed that each of Fv3-M73, Fv4-M73, and Fv5-M83 exhibited significantly improved pharmacokinetics in cynomolgus monkeys when compared to TOCILIZUMAB and the control. Of them, Fv3-M73 and Fv4-M73 exhibited highly improved pharmacokinetics when compared to TOCILIZUMAB.

Figure 19:
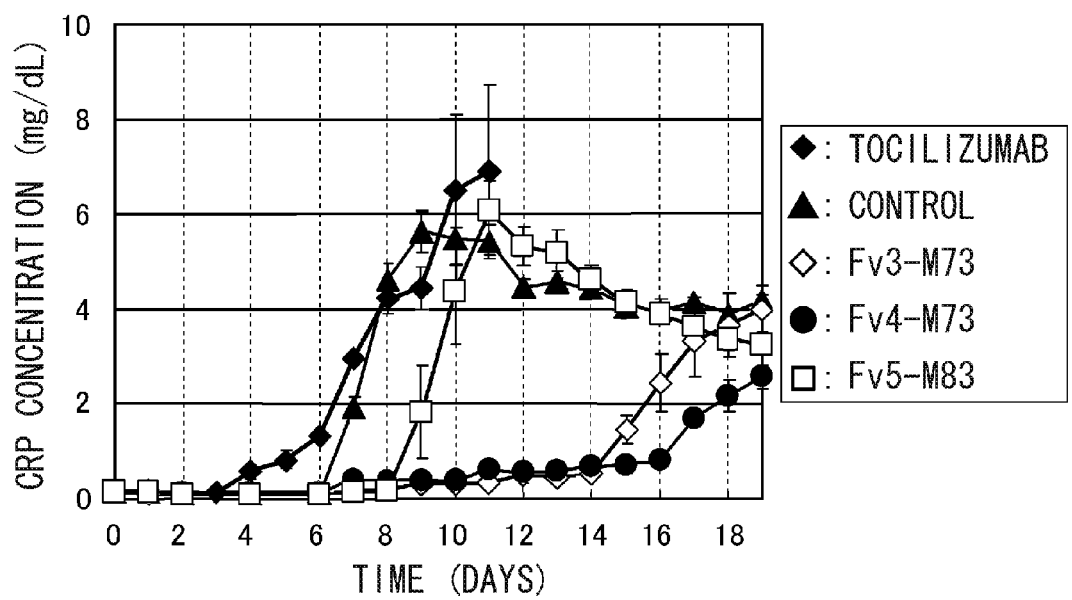
Figure 20:
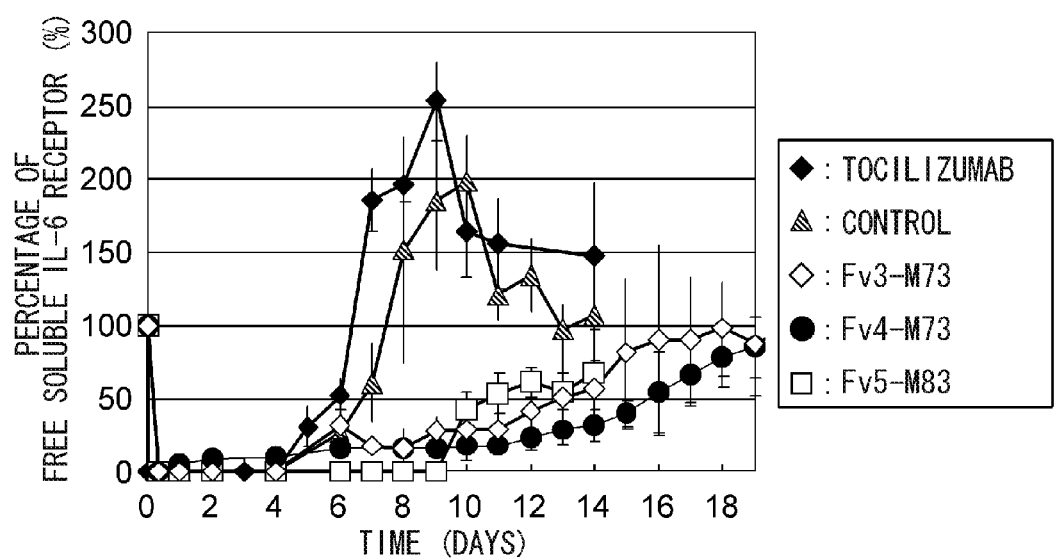

The efficacy of each antibody to neutralize membrane-type cynomolgus monkey IL-6 receptor was assessed. Cynomolgus monkey IL-6 was administered subcutaneously in the lower back at 5 μg/kg every day from Day 6 to Day 18 after antibody administration (Day 3 to Day 10 for TOCILIZUMAB), and the CRP concentration in each animal was determined 24 hours later (see Reference Example for method). The time course of CRP concentration after administration of each antibody is shown in FIG. 19. To assess the efficacy of each antibody to neutralize soluble cynomolgus monkey IL-6 receptor, the plasma concentration of free soluble cynomolgus monkey IL-6 receptor in the cynomolgus monkeys was determined and the percentages of free soluble IL-6 receptor were calculated (see Reference Example for method). The time course of percentage of free soluble IL-6 receptor after administration of each antibody is shown in FIG. 20.

Each of Fv3-M73, Fv4-M73, and Fv5-M83 neutralized membrane-type cynomolgus monkey IL-6 receptor in a more sustainable way, and suppressed the increase of CRP over a longer period when compared to TOCILIZUMAB and the control (the known high-affinity anti-IL-6 receptor antibody). Furthermore, each of Fv3-M73, Fv4-M73, and Fv5-M83 neutralized soluble cynomolgus monkey IL-6 receptor in a more sustainable way, and suppressed the increase of free soluble cynomolgus monkey IL-6 receptor over a longer period when compared to TOCILIZUMAB and the control. These findings demonstrate that all of Fv3-M73, Fv4-M73, and Fv5-M83 are superior in sustaining the neutralization of membrane-type and soluble IL-6 receptors than TOCILIZUMAB and the control. Of them, Fv3-M73 and Fv4-M73 are remarkably superior in sustaining the neutralization. Meanwhile, Fv5-M83 suppressed CRP and free soluble cynomolgus monkey IL-6 receptor more strongly than Fv3-M73 and Fv4-M73. Thus, Fv5-M83 is considered to be stronger than Fv3-M73, Fv4-M73, and the control (the known high-affinity anti-IL-6 receptor antibody) in neutralizing membrane-type and soluble IL-6 receptors. It was considered that results in in vivo of cynomolgus monkeys reflect the stronger affinity of Fv5-M83 for IL-6 receptor and stronger biological activity of Fv5-M83 in the BaF/gp130 assay system relative to the control.

These findings suggest that Fv3-M73 and Fv4-M73 are highly superior in sustaining their activities as an anti-IL-6 receptor-neutralizing antibody when compared to TOCILIZUMAB and the control, and thus enable to significantly reduce the dosage and frequency of administration. Furthermore, Fv5-M83 was demonstrated to be remarkably superior in terms of the strength of activity as an anti-IL-6 receptor-neutralizing antibody as well as sustaining their activity. Thus, Fv3-M73, Fv4-M73, and Fv5-M83 are expected to be useful as pharmaceutical IL-6 antagonists.

Example 9

Monocyte chemoattractant protein (MCP)-1 is known to be involved in cellular invasion of monocytes, T cells, NK cells, and basophils. MCP-1 has been reported to be highly expressed in synovial tissues/synovial fluid of RA patients (J. Clin. Invest., September 1992, 90(3):772-779) and is thought to be involved in the pathological condition of RA (Inflamm. Allergy Drug Targets, March 2008, 7(1):53-66).

VEGF is a potent angiogenic factor and is known to be produced, for example, by macrophages, fibroblasts, and synovial cells in the synovial membrane of RA patients (J. Rheumatol., September 1995, 22(9):1624-1630). Moreover, the VEGF level in the serum of RA patients correlates with disease activity and radiographic progression (Arthritis Rheum., June 2003, 48(6):1521-1529; and Arthritis Rheum., September 2001, 44(9):2055-2064) and the VEGF level in the serum decreases by treating RA patients with the anti-IL-6R antibody TOCILIZUMAB; therefore, VEGF is also considered to play an important role in the pathological condition of RA (Mod. Rheumatol. 2009, 19(1):12-19; and Mediators Inflamm. 2008, 2008:129873).

Thus, whether TOCILIZUMAB and Fv4-M73 can inhibit MCP-1 and VEGF productions from human RA patient-derived synovial cells which occur from sIL-6R and IL-6 stimulation was examined.

Figure 21:
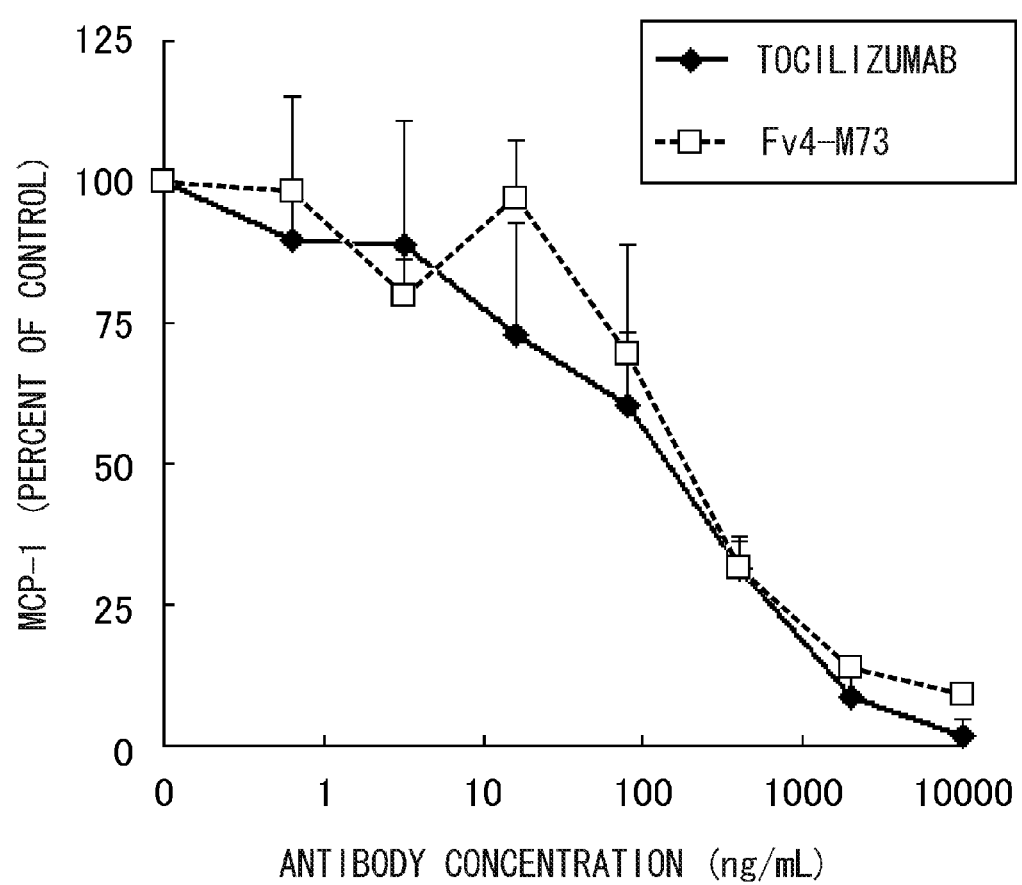
Figure 22:
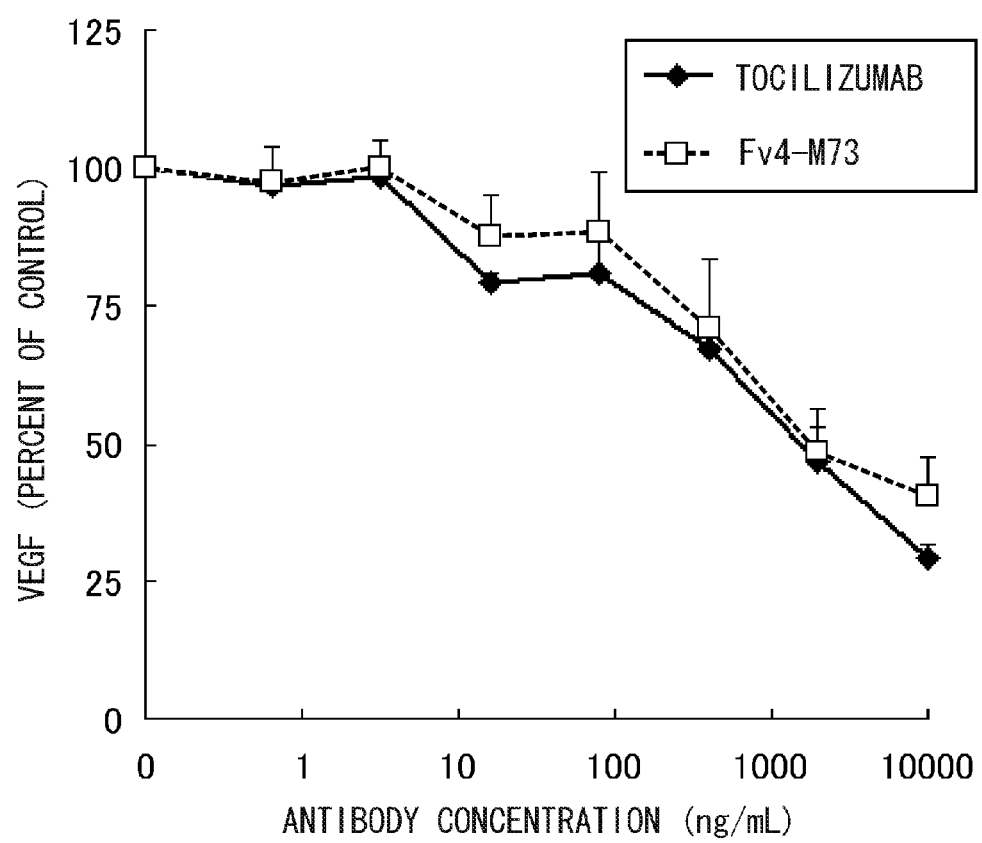

Human RA patient-derived synovial cells (TOYOBO) were plated onto 96 well plates in 5% FCS-containing IMDM medium at $2\times10^4$ cells/0.05 mL/well, and placed for 90 minutes in a $CO_2$ incubator (37° C., 5% $CO_2$). 0.05 mL of TOCILIZUMAB and Fv4-M73 diluted to appropriate concentrations were added, the plates were left still for 15 minutes, then 0.05 mL of soluble IL-6 receptor (SR344: prepared according to the method described in Reference Examples) were added. The plates were further left still for 30 minutes, and 0.05 mL of IL-6 (TORAY) were further added (the final concentrations of soluble IL-6 receptor and IL-6 were 50 ng/mL for each). After two days of culture, the culture supernatants were collected, and the MCP-1 and VEGF concentrations in the culture supernatants were measured using ELISA kit (Biosource and Pierce Biotechnology). The results are shown in FIGS. 21 and 22. TOCILIZUMAB and Fv4-M73 inhibited MCP-1 and VEGF production from human RA patient-derived synovial cells following soluble IL-6 receptor and IL-6 stimulation in a concentration-dependent manner.

Accordingly, the persistence of the effect of Fv4-M73 as an anti-IL-6 receptor neutralizing antibody (the effect of binding to the IL-6 receptor and blocking the signals of the membrane-type IL6 receptor and soluble IL-6 receptor) is significantly superior as compared to TOCILIZUMAB, the administration frequency and dose can be greatly reduced as compared to TOCILIZUMAB, and furthermore, Fv4-M73 inhibits MCP-1 and VEGF production from human RA patient-derived synovial cells. Therefore, Fv4-M73 was shown to be a very effective therapeutic agent against RA.

REFERENCE EXAMPLES

Preparation of Soluble Recombinant Human IL-6 Receptor

Soluble recombinant human IL-6 receptor of the human IL-6 receptor, which is the antigen, was produced as described below. A CHO cell line constitutively expressing a soluble human IL-6 receptor containing a sequence from the N-terminal 1st to 344th amino acids reported in J. Biochem. (1990) 108, 673-676 (Yamasaki et al., Science (1988) 241, 825-828 (GenBank #X12830)) was generated. Soluble human IL-6 receptor was purified from culture supernatant of CHO cells expressing SR344 by three column chromatographies: Blue Sepharose 6 FF column chromatography, affinity chromatography using a column immobilized with an antibody specific to SR344, and gel filtration column chromatography. The fraction eluted as the main peak was used as the final purified sample.

Preparation of Soluble Recombinant Cynomolgus Monkey IL-6 Receptor (cIL-6R)

Oligo-DNA primers were prepared based on the disclosed gene sequence for Rhesus monkey IL-6 receptor (Birney et al., Ensembl 2006, Nucleic Acids Res. 2006 Jan. 1; 34 (Database issue):D556-61). A DNA fragment encoding the whole cynomolgus monkey IL-6 receptor gene was prepared by PCR using the primers, and as a template, cDNA prepared from the pancreas of cynomolgus monkey. The resulting DNA fragment was inserted into a mammalian cell expression vector, and a stable expression CHO line (cyno.sIL-6R-producing CHO cell line) was prepared using the vector. The culture medium of cyno.sIL-6R-producing CHO cells was purified using a HisTrap column (GE Healthcare Bioscience) and then concentrated with Amicon Ultra-15 Ultracel-10k (Millipore). A final purified sample of soluble cynomolgus monkey IL-6 receptor (hereinafter cIL-6R) was obtained through further purification on a Superdex200pg16/60 gel filtration column (GE Healthcare Bioscience).

Preparation of Recombinant Cynomolgus Monkey IL-6 (cIL-6)

Cynomolgus monkey IL-6 was prepared by the procedure described below. The nucleotide sequence encoding 212 amino acids deposited under SWISSPROT Accession No. P79341 was prepared and cloned into a mammalian cell expression vector. The resulting vector was introduced into CHO cells to prepare a stable expression cell line (cyno.IL-6-producing CHO cell line). The culture medium of cyno.IL-6-producing CHO cells was purified using a SP-Sepharose/FF column (GE Healthcare Bioscience) and then concentrated with Amicon Ultra-15 Ultracel-5k (Millipore). A final purified sample of cynomolgus monkey IL-6 (hereinafter cIL-6) was obtained through further purification on a Superdex75pg26/60 gel filtration column (GE Healthcare Bioscience), followed by concentration with Amicon Ultra-15 Ultracel-5k (Millipore).

Preparation of a Known High-Affinity Anti-IL-6 Receptor Antibody

A mammalian cell expression vector was constructed to express VQ8F11-21 hIgG1, a known high-affinity anti-IL-6 receptor antibody. VQ8F11-21 hIgG1 is described in US 2007/0280945 A1 (US 2007/0280945 A1; the amino acid sequences of H chain and L chain as set forth in SEQ ID NOs: 77 and 78, respectively). The antibody variable region was constructed by PCR using a combination of synthetic oligo DNAs (assembly PCR) and IgG1 was used for the constant region. The antibody variable and constant regions were combined together by assembly PCR, and then inserted into a mammalian expression vector to construct expression vectors for the H chain and L chain of interest. The nucleotide sequences of the resulting expression vectors were determined by a method known to those skilled in the art. The high-affinity anti-IL-6 receptor antibody (hereinafter abbreviated as "control") was expressed and purified using the constructed expression vectors by the method described in Example 1.

Preparation, Expression, and Purification of TOCILIZUMAB Variants

TOCILIZUMAB variants were prepared using the QuikChange Site-Directed Mutagenesis Kit (Stratagene) according to the method described in the appended instruction manual. The resulting plasmid fragments were inserted into mammalian cell expression vectors to construct expression vectors for the H chains and L chains of interest. The nucleotide sequences of the obtained expression vectors were determined by a method known to skilled artisans. The antibodies were expressed by the method described below. Human embryonic kidney cancer-derived HEK293H cell line (Invitrogen) was suspended in DMEM (Invitrogen) supplemented with 10% Fetal Bovine Serum (Invitrogen). The cells were plated at 10 ml per dish in dishes for adherent cells (10 cm in diameter; CORNING) at a cell density of 5 to $6 \times 10^5$ cells/ml and cultured in a $CO_2$ incubator (37° C., 5% $CO_2$) for one whole day and night. Then, the medium was removed by aspiration, and 6.9 ml of CHO-S-SFM-II medium (Invitrogen) was added. The prepared plasmid was introduced into the cells by the lipofection method. The resulting culture supernatants were collected, centrifuged (approximately 2000 g, 5 min, room temperature) to remove cells, and sterilized by filtering through 0.22-µm filter MILLEX®-GV (Millipore) to obtain the supernatants. Antibodies were purified from the obtained culture supernatants by a method known to those skilled in the art using rProtein A Sepharose™ Fast Flow (Amersham Biosciences). To determine the concentration of the purified antibody, absorbance was measured at 280 nm using a spectrophotometer. Antibody concentrations were calculated from the determined values using an absorbance coefficient calculated by the PACE method (Protein Science 1995; 4:2411-2423).

Establishment of a Human gp130-Expressing BaF3 Cell Line

A BaF3 cell line expressing human gp130 was established by the procedure described below to obtain a cell line that proliferates in an IL-6-dependent manner.

A full-length human gp130 cDNA (Hibi et al., Cell (1990) 63:1149-1157 (GenBank #NM_002184)) was amplified by PCR and cloned into the expression vector pCOS2Zeo to construct pCOS2Zeo/gp130. pCOS2Zeo is an expression vector constructed by removing the DHFR gene expression region from pCHOI (Hirata et al., FEBS Letter (1994) 356:244-248) and inserting the expression region of the Zeocin resistance gene. The full-length human IL-6R cDNA was amplified by PCR and cloned into pcDNA3.1(+) (Invitrogen) to construct hIL-6R/pcDNA3.1(+).

10 µg of pCOS2Zeo/gp130 was mixed with BaF3 cells ($0.8 \times 10^7$ cells) suspended in PBS, and then pulsed at 0.33 kV and 950 µFD using Gene Pulser (Bio-Rad). The BaF3 cells having the gene introduced by electroporation were cultured for one whole day and night in RPMI 1640 medium (Invitrogen) supplemented with 0.2 ng/ml mouse interleukin-3 (Peprotech) and 10% fetal bovine serum (hereinafter FBS, HyClone), and selected by adding RPMI 1640 medium supplemented with 100 ng/ml human interleukin-6 (R&D systems), 100 ng/ml human interleukin-6 soluble receptor (R&D systems), and 10% FBS to establish a human gp130-expressing BaF3 cell line (hereinafter "BaF3/gp130"). This BaF/gp130 proliferates in the presence of human interleukin-6 (R&D systems) and soluble human IL-6 receptor, and thus can be used to assess the growth inhibition activity (or IL-6 receptor neutralizing activity) of an anti-IL-6 receptor antibody.

Assessment for the Biological Activity by Human gp130-Expressing BaF3 Cells (BaF/gp130)

The IL-6 receptor neutralizing activity was assessed using BaF3/gp130 which proliferates in an IL-6/IL-6 receptor-dependent manner. After three washes with RPMI1640 supplemented with 10% FBS, BaF3/gp130 cells were suspended at $5 \times 10^4$ cells/ml in RPMI1640 supplemented with 600 ng/ml or 60 ng/ml human interleukin-6 (TORAY) (final concentration of 300 ng/ml or 30 ng/ml), appropriate amount of soluble human IL-6 receptor, and 10% FBS. The cell suspensions were dispensed (50 µl/well) into 96-well plates (CORNING). Then, the purified antibodies were diluted with RPMI1640 containing 10% FBS, and added to each well (50 µl/well). The cells were cultured at 37° C. under 5% $CO_2$ for three days. WST-8 Reagent (Cell Counting Kit-8; Dojindo Laboratories) was diluted two-fold with PBS. Immediately after 20 µl of the reagent was added to each well, the absorbance at 450 nm (reference wavelength: 620 nm) was measured using SUNRISE CLASSIC (TECAN). After culturing for two hours, the absorbance at 450 nm (reference wavelength: 620 nm) was measured again. The IL-6 receptor neutralizing activity was assessed using the change of absorbance during two hours as an indicator.

Biacore-Based Analysis of Binding to Soluble Human IL-6 Receptor

Antigen-antibody reaction kinetics was analyzed using Biacore T100 (GE Healthcare). The soluble human IL-6 receptor-antibody interaction was measured by immobilizing appropriate amounts of protein A or protein A/G or anti-IgG (γ-chain specific) F(ab')2 onto a sensor chip by amine coupling method, binding antibodies of interest onto the chip at pH7.4, and then running soluble IL-6 receptor adjusted to various concentrations at pH7.4 over the chip as an analyte. All measurements were carried out at 37° C. The kinetic parameters, association rate constant $k_a$ (1/Ms) and dissociation rate constant $k_d$ (1/s) were calculated from the sensorgrams obtained by measurement. Then, $K_D$ (M) was determined based on the rate constants. The respective parameters were determined using Biacore T100 Evaluation Software (GE Healthcare).

Assessment for the pH-Dependent Dissociation from Membrane-Type IL-6 Receptor Using Biacore The antigen-antibody reaction with membrane-type IL-6 receptor at pH 5.8 and pH 7.4 was observed using Biacore T100 (GE Healthcare). The binding to membrane-type IL-6 receptor was assessed by evaluating the binding to soluble human IL-6 receptor immobilized onto the sensor chip. SR344 was biotinylated by a method known to those skilled in the art. Based on the affinity between biotin and streptavidin, biotinylated soluble human IL-6 receptor was immobilized onto the sensor chip via streptavidin. All measurements were conducted at 37° C. The mobile phase buffer was 10 mM MES (pH 5.8), 150 mM NaCl, and 0.05% Tween 20. A clone exhibiting pH-dependent binding was injected under the condition of pH 7.4 to bind to soluble human IL-6 receptor (injection sample buffer was 10 mM MES (pH 7.4), 150 mM NaCl, and 0.05% Tween 20). Then, the pH-dependent dissociation of each clone was observed at pH 5.8, which is the pH of the mobile phase. The dissociation rate constant (kd (1/s)) at pH 5.8 was calculated using Biacore T100 Evaluation Software (GE Healthcare) by fitting only the dissociation phase at pH 5.8. The sample concentration was 0.25 µg/ml. Binding was carried out in 10 mM MES (pH 7.4), 150 mM NaCl, and 0.05% Tween 20, and dissociation was carried out in 10 mM MES (pH 5.8), 150 mM NaCl, and 0.05% Tween 20. Likewise, the dissociation rate constant (kd (1/s)) at pH 7.4 was calculated using Biacore T100 Evaluation Software (GE Healthcare) by fitting only the dissociation phase at pH 7.4. The sample concentration was 0.5 µg/ml. Binding was carried out in 10 mM MES (pH 7.4), 150 mM NaCl, and 0.05% Tween 20, and dissociation was carried out in 10 mM MES (pH 7.4), 150 mM NaCl, and 0.05% Tween 20.

Assessment of the Binding to Human FcRn

FcRn is a complex of FcRn and β2-microglobulin. Oligo-DNA primers were prepared based on the human FcRn gene sequence disclosed (J. Exp. Med. (1994) 180(6):2377-2381). A DNA fragment encoding the whole gene was prepared by PCR using human cDNA (Human Placenta Marathon-Ready cDNA, Clontech) as a template and the prepared primers. Using the obtained DNA fragment as a template, a DNA fragment encoding the extracellular domain containing the signal region (Met1-Leu290) was amplified by PCR, and inserted into a mammalian cell expression vector (the amino acid sequence of human FcRn as set forth in SEQ ID NO: 79). Likewise, oligo-DNA primers were prepared based on the human β2-microglobulin gene sequence disclosed (Proc. Natl. Acad. Sci. USA. (2002) 99(26):16899-16903). A DNA fragment encoding the whole gene was prepared by PCR using human cDNA (Hu-Placenta Marathon-Ready cDNA, CLONTECH) as a template and the prepared primers. Using the obtained DNA fragment as a template, a DNA fragment encoding the whole β2-microglobulin containing the signal region (Met1-Met119) was amplified by PCR and inserted into a mammalian cell expression vector (the amino acid sequence of human β2-microglobulin as set forth in SEQ ID NO: 80).

Soluble human FcRn was expressed by the following procedure. The plasmids constructed for human FcRn and β2-microglobulin were introduced into cells of the human embryonic kidney cancer-derived cell line HEK293H (Invitrogen) using 10% FBS (Invitrogen) by lipofection. The resulting culture supernatant was collected, and FcRn was purified using IgG Sepharose 6 Fast Flow (Amersham Biosciences) by the method described in J. Immunol. 2002 Nov. 1; 169(9):5171-80, followed by further purification using HiTrap Q HP (GE Healthcare).

Determination of Antibody Concentration in Mouse Plasma

Antibody concentrations in mouse plasma were determined by ELISA according to a method known to those skilled in the art.

PK/PD Test to Determine the Antibody Concentration in the Plasma, CRP Concentration, and Free Soluble IL-6 Receptor in Monkeys The plasma concentrations in cynomolgus monkeys were determined by ELISA using a method known to those skilled in the art.

The concentration of CRP was determined with an automated analyzer (TBA-120FR; Toshiba Medical Systems Co.) using Cias R CRP (KANTO CHEMICAL CO., INC.).

The plasma concentration of free soluble cynomolgus monkey IL-6 receptor in cynomolgus monkeys was determined by the procedure described below. All IgG-type antibodies (cynomolgus monkey IgG, anti-human IL-6 receptor antibody, and anti-human IL-6 receptor antibody-soluble cynomolgus monkey IL-6 receptor complex) in the plasma were adsorbed onto Protein A by loading 30 µl of cynomolgus monkey plasma onto an appropriate amount of rProtein A Sepharose Fast Flow resin (GE Healthcare) dried in a 0.22-µm filter cup (Millipore). Then, the solution in cup was spinned down using a high-speed centrifuge to collect the solution that passed through. The solution that passed through does not contain Protein A-bound anti-human IL-6 receptor antibody-soluble cynomolgus monkey IL-6 receptor complex. Therefore, the concentration of free soluble IL-6 receptor can be determined by measuring the concentration of soluble cynomolgus monkey IL-6 receptor in the solution that passed through Protein A. The concentration of soluble cynomolgus monkey IL-6 receptor was determined using a method known to those skilled in the art for measuring the concentrations of soluble human IL-6 receptor. Soluble cynomolgus monkey IL-6 receptor (cIL-6R) prepared as described above was used as a standard. The percentage of free soluble IL-6 receptor was calculated by the following formula.

$$\frac{\text{Free soluble } IL\text{-}6 \text{ receptor concentration after antibody administration}}{\text{Soluble } IL\text{-}6 \text{ receptor concentration before antibody administration}} \times 100$$

The invention claimed is:

1. A method for treating an IL-6-associated inflammatory disease or condition, or an IL-6-associated autoimmune disease or condition, the method comprising administering an effective amount of a pharmaceutical composition comprising an anti-IL-6 receptor antibody to a subject in need thereof, wherein the antibody comprises (a) a heavy chain variable region that comprises CDR1 comprising the sequence of SEQ ID NO: 4, CDR2 comprising the sequence of SEQ ID NO: 5, and CDR3 comprising the sequence of SEQ ID NO: 6; and (b) a light chain variable region that comprises CDR1 comprising the sequence of SEQ ID NO: 13, CDR2 comprising the sequence of SEQ ID NO: 14, and CDR3 comprising the sequence of SEQ ID NO: 15, wherein the pharmaceutical composition is administered intravenously, intramuscularly, or subcutaneously.

2. The method of claim 1, wherein the subject has an inflammatory disease or inflammatory condition.

3. The method of claim 1, wherein the subject has an autoimmune disease or autoimmune condition.

4. The method of claim 1, wherein the subject has a disease or condition selected from the group consisting of rheumatoid arthritis, juvenile idiopathic arthritis, systemic juvenile idiopathic arthritis, Castleman's disease, systemic lupus erythematosus (SLE), lupus nephritis, Crohn's disease, ulcerative colitis, vasculitis, Kawasaki disease, Still's disease, amyloidosis, multiple sclerosis, age-related macular degeneration, ankylosing spondylitis, psoriasis, psoriatic arthritis, chronic obstructive pulmonary disease (COPD), IgA nephropathy, osteoarthritis, asthma, diabetic nephropathy, GVHD, endometriosis, nonalcoholic steatohepatitis (NASH), arteriosclerosis, sepsis, uveitis, chronic thyroiditis, delayed hypersensitivity, contact dermatitis, atopic dermatitis, polymyositis, dermatomyositis, panuveitis, anterior uveitis, intermediate uveitis, scleritis, keratitis, orbital inflammation, optic neuritis, diabetic retinopathy, and proliferative vitreoretinopathy.

5. The method of claim 1, wherein the subject has optic neuritis.

6. The method of claim 1, wherein the subject has rheumatoid arthritis.

7. The method of claim 1, wherein the subject has osteoarthritis.

8. The method of claim 1, wherein the subject has juvenile idiopathic arthritis.

9. The method of claim 1, wherein the subject has systemic juvenile idiopathic arthritis.

10. The method of claim 1, wherein the subject has ankylosing spondylitis.

11. The method of claim 1, wherein the subject has vasculitis.

12. The method of claim 1, wherein the subject has polymyositis.

13. The method of claim 1, wherein the subject has Still's disease.

14. The method of claim 1, wherein the subject has asthma.

15. The method of claim 1, wherein the subject has Graft Versus Host Disease (GVHD).

16. The method of claim 1, wherein the subject has sepsis.

17. The method of claim 1, wherein the subject has Castleman's disease.

18. The method of claim 1, wherein the subject has systemic lupus erythematosus (SLE).

19. The method of claim 1, wherein the subject has Crohn's disease.

20. The method of claim 1, wherein the subject has ulcerative colitis.

21. The method of claim 1, wherein the subject has multiple sclerosis.

22. A method for treating an IL-6-associated inflammatory disease or condition, or an IL-6-associated autoimmune disease or condition, the method comprising administering an effective amount of a pharmaceutical composition comprising an anti-IL-6 receptor antibody to a subject in need thereof, wherein the antibody comprises
  (a) a heavy chain variable region comprising the sequence of SEQ ID NO: 20 and
  (b) a light chain variable region comprising the sequence of SEQ ID NO: 23,
  wherein the pharmaceutical composition is administered intravenously, intramuscularly, or subcutaneously.

23. The method of claim 22, wherein the subject has optic neuritis.

24. A method for treating an IL-6-associated inflammatory disease or condition, or an IL-6-associated autoimmune disease or condition, the method comprising administering an effective amount of a pharmaceutical composition comprising an anti-IL-6 receptor antibody to a subject in need thereof, wherein the antibody comprises
  (a) a heavy chain comprising the sequence of SEQ ID NO: 26 and
  (b) a light chain comprising the sequence of SEQ ID NO: 29,
  wherein the pharmaceutical composition is administered intravenously, intramuscularly, or subcutaneously.

25. The method of claim 24, wherein the subject has optic neuritis.

* * * * *

SEQUENCE LISTING

```
<160> NUMBER OF SEQ ID NOS: 117

<210> SEQ ID NO 1
<211> LENGTH: 6
<212> TYPE: PRT
<213> ORGANISM: Artificial
<220> FEATURE:
<223> OTHER INFORMATION: An artificially synthesized polypeptide
      sequence

<400> SEQUENCE: 1

His Asp His Ala Trp Ser
1               5

<210> SEQ ID NO 2
<211> LENGTH: 16
<212> TYPE: PRT
<213> ORGANISM: Artificial
<220> FEATURE:
<223> OTHER INFORMATION: An artificially synthesized polypeptide
      sequence

<400> SEQUENCE: 2

Phe Ile Ser Tyr Ser Gly Ile Thr Asn Tyr Asn Pro Thr Leu Gln Gly
1               5                   10                  15

<210> SEQ ID NO 3
<211> LENGTH: 10
<212> TYPE: PRT
<213> ORGANISM: Artificial
<220> FEATURE:
<223> OTHER INFORMATION: An artificially synthesized polypeptide
      sequence

<400> SEQUENCE: 3

Ser Leu Ala Arg Thr Thr Ala Met Asp Tyr
1               5                   10

<210> SEQ ID NO 4
<211> LENGTH: 6
```

-continued

```
<212> TYPE: PRT
<213> ORGANISM: Artificial
<220> FEATURE:
<223> OTHER INFORMATION: An artificially synthesized polypeptide
      sequence

<400> SEQUENCE: 4

His Asp His Ala Trp Ser
1               5

<210> SEQ ID NO 5
<211> LENGTH: 16
<212> TYPE: PRT
<213> ORGANISM: Artificial
<220> FEATURE:
<223> OTHER INFORMATION: An artificially synthesized polypeptide
      sequence

<400> SEQUENCE: 5

Phe Ile Ser Tyr Ser Gly Ile Thr Asn Tyr Asn Pro Ser Leu Gln Gly
1               5                   10                  15

<210> SEQ ID NO 6
<211> LENGTH: 10
<212> TYPE: PRT
<213> ORGANISM: Artificial
<220> FEATURE:
<223> OTHER INFORMATION: An artificially synthesized polypeptide
      sequence

<400> SEQUENCE: 6

Ser Leu Ala Arg Thr Thr Ala Met Asp Tyr
1               5                   10

<210> SEQ ID NO 7
<211> LENGTH: 6
<212> TYPE: PRT
<213> ORGANISM: Artificial
<220> FEATURE:
<223> OTHER INFORMATION: An artificially synthesized polypeptide
      sequence

<400> SEQUENCE: 7

Asp Asp His Ala Val Ser
1               5

<210> SEQ ID NO 8
<211> LENGTH: 16
<212> TYPE: PRT
<213> ORGANISM: Artificial
<220> FEATURE:
<223> OTHER INFORMATION: An artificially synthesized polypeptide
      sequence

<400> SEQUENCE: 8

Phe Ile Ser Tyr Ser Gly Ile Thr Asn Tyr Asn Pro Thr Leu Gln Asp
1               5                   10                  15

<210> SEQ ID NO 9
<211> LENGTH: 10
<212> TYPE: PRT
<213> ORGANISM: Artificial
<220> FEATURE:
<223> OTHER INFORMATION: An artificially synthesized polypeptide
      sequence

<400> SEQUENCE: 9

Leu Leu Ala Arg Ala Thr Ala Met Asp Val
```

```
<210> SEQ ID NO 10
<211> LENGTH: 11
<212> TYPE: PRT
<213> ORGANISM: Artificial
<220> FEATURE:
<223> OTHER INFORMATION: An artificially synthesized polypeptide
      sequence

<400> SEQUENCE: 10

Gln Ala Ser Arg Asp Ile Ser Ser His Leu Asn
1               5                   10

<210> SEQ ID NO 11
<211> LENGTH: 7
<212> TYPE: PRT
<213> ORGANISM: Artificial
<220> FEATURE:
<223> OTHER INFORMATION: An artificially synthesized polypeptide
      sequence

<400> SEQUENCE: 11

Tyr Gly Ser His Leu Leu Ser
1               5

<210> SEQ ID NO 12
<211> LENGTH: 9
<212> TYPE: PRT
<213> ORGANISM: Artificial
<220> FEATURE:
<223> OTHER INFORMATION: An artificially synthesized polypeptide
      sequence

<400> SEQUENCE: 12

Gly Gln Gly Asn Arg Leu Pro Tyr Thr
1               5

<210> SEQ ID NO 13
<211> LENGTH: 11
<212> TYPE: PRT
<213> ORGANISM: Artificial
<220> FEATURE:
<223> OTHER INFORMATION: An artificially synthesized polypeptide
      sequence

<400> SEQUENCE: 13

Gln Ala Ser Thr Asp Ile Ser Ser His Leu Asn
1               5                   10

<210> SEQ ID NO 14
<211> LENGTH: 7
<212> TYPE: PRT
<213> ORGANISM: Artificial
<220> FEATURE:
<223> OTHER INFORMATION: An artificially synthesized polypeptide
      sequence

<400> SEQUENCE: 14

Tyr Gly Ser His Leu Leu Ser
1               5

<210> SEQ ID NO 15
<211> LENGTH: 9
<212> TYPE: PRT
<213> ORGANISM: Artificial
<220> FEATURE:
<223> OTHER INFORMATION: An artificially synthesized polypeptide
```

-continued sequence

<400> SEQUENCE: 15

Gly Gln Gly Asn Arg Leu Pro Tyr Thr
1               5

<210> SEQ ID NO 16
<211> LENGTH: 11
<212> TYPE: PRT
<213> ORGANISM: Artificial
<220> FEATURE:
<223> OTHER INFORMATION: An artificially synthesized polypeptide
      sequence

<400> SEQUENCE: 16

Gln Ala Ser Gln Asp Ile Ser Ser Tyr Leu Asn
1               5                   10

<210> SEQ ID NO 17
<211> LENGTH: 7
<212> TYPE: PRT
<213> ORGANISM: Artificial
<220> FEATURE:
<223> OTHER INFORMATION: An artificially synthesized polypeptide
      sequence

<400> SEQUENCE: 17

Tyr Gly Ser Glu Leu Glu Ser
1               5

<210> SEQ ID NO 18
<211> LENGTH: 9
<212> TYPE: PRT
<213> ORGANISM: Artificial
<220> FEATURE:
<223> OTHER INFORMATION: An artificially synthesized polypeptide
      sequence

<400> SEQUENCE: 18

Gly Gln Gly Asn Arg Leu Pro Tyr Thr
1               5

<210> SEQ ID NO 19
<211> LENGTH: 119
<212> TYPE: PRT
<213> ORGANISM: Artificial
<220> FEATURE:
<223> OTHER INFORMATION: An artificially synthesized polypeptide
      sequence

<400> SEQUENCE: 19

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Thr Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly

Thr Leu Val Thr Val Ser Ser
        115

<210> SEQ ID NO 20
<211> LENGTH: 119
<212> TYPE: PRT
<213> ORGANISM: Artificial
<220> FEATURE:
<223> OTHER INFORMATION: An artificially synthesized polypeptide
      sequence

<400> SEQUENCE: 20

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser
        115

<210> SEQ ID NO 21
<211> LENGTH: 119
<212> TYPE: PRT
<213> ORGANISM: Artificial
<220> FEATURE:
<223> OTHER INFORMATION: An artificially synthesized polypeptide
      sequence

<400> SEQUENCE: 21

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

His Ala Val Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Thr Leu
    50                  55                  60

Gln Asp Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Leu Ala Arg Ala Thr Ala Met Asp Val Trp Gly Glu Gly
            100                 105                 110

Thr Leu Val Thr Val Ser Ser
        115

<210> SEQ ID NO 22
<211> LENGTH: 107
<212> TYPE: PRT

<213> ORGANISM: Artificial
<220> FEATURE:
<223> OTHER INFORMATION: An artificially synthesized polypeptide
      sequence

<400> SEQUENCE: 22

Asp Ile Gln Met Thr Gln Ser Pro Ser Ser Leu Ser Ala Ser Val Gly
1               5                   10                  15

Asp Ser Val Thr Ile Thr Cys Gln Ala Ser Arg Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu Leu Ser Gly Val Pro Ser Arg Phe Ser Gly
50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu
            100                 105

<210> SEQ ID NO 23
<211> LENGTH: 107
<212> TYPE: PRT
<213> ORGANISM: Artificial
<220> FEATURE:
<223> OTHER INFORMATION: An artificially synthesized polypeptide
      sequence

<400> SEQUENCE: 23

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu Leu Ser Gly Val Pro Ser Arg Phe Ser Gly
50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu
            100                 105

<210> SEQ ID NO 24
<211> LENGTH: 107
<212> TYPE: PRT
<213> ORGANISM: Artificial
<220> FEATURE:
<223> OTHER INFORMATION: An artificially synthesized polypeptide
      sequence

<400> SEQUENCE: 24

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Glu Leu Leu Ile
        35                  40                  45

```
Tyr Tyr Gly Ser Glu Leu Glu Ser Gly Val Pro Ser Arg Phe Ser Gly
            50                  55                  60

Ser Gly Ser Gly Thr Asp Phe Thr Phe Thr Ile Ser Ser Leu Glu Ala
 65                  70                  75                  80

Glu Asp Ala Ala Thr Tyr Tyr Cys Gly Gln Gly Asn Arg Leu Pro Tyr
                 85                  90                  95

Thr Phe Gly Gln Gly Thr Lys Val Glu Ile Glu
                100                 105
```

<210> SEQ ID NO 25
<211> LENGTH: 443
<212> TYPE: PRT
<213> ORGANISM: Artificial
<220> FEATURE:
<223> OTHER INFORMATION: An artificially synthesized polypeptide
      sequence

<400> SEQUENCE: 25

```
Gln Val Gln Leu Gln Glu Ser Gly Pro Gly Leu Val Lys Pro Ser Glu
  1               5                  10                  15

Thr Leu Ser Leu Thr Cys Ala Val Ser Gly His Ser Ile Ser His Asp
             20                  25                  30

His Ala Trp Ser Trp Val Arg Gln Pro Pro Gly Glu Gly Leu Glu Trp
         35                  40                  45

Ile Gly Phe Ile Ser Tyr Ser Gly Ile Thr Asn Tyr Asn Pro Thr Leu
     50                  55                  60

Gln Gly Arg Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Leu Ala Arg Thr Thr Ala Met Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
210                 215                 220

Cys Pro Pro Cys Pro Ala Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
```

```
                290                 295                 300
Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
                340                 345                 350

Gln Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
                370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Ala
                420                 425                 430

His Tyr Thr Gln Lys Ser Leu Ser Leu Ser Pro
                435                 440

<210> SEQ ID NO 26
<211> LENGTH: 443
<212> TYPE: PRT
<213> ORGANISM: Artificial
<220> FEATURE:
<223> OTHER INFORMATION: An artificially synthesized polypeptide
      sequence

<400> SEQUENCE: 26

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
                20                  25                  30

His Ala Trp Ser Trp Val Arg Gln Pro Pro Gly Glu Gly Leu Glu Trp
                35                  40                  45

Ile Gly Phe Ile Ser Tyr Ser Gly Ile Thr Asn Tyr Asn Pro Ser Leu
                50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Asn Phe Gly Thr Gln Thr Tyr Thr Cys Asn Val Asp His Lys Pro
                195                 200                 205
```

```
Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Ala
            420                 425                 430

His Tyr Thr Gln Lys Ser Leu Ser Leu Ser Pro
        435                 440

<210> SEQ ID NO 27
<211> LENGTH: 447
<212> TYPE: PRT
<213> ORGANISM: Artificial
<220> FEATURE:
<223> OTHER INFORMATION: An artificially synthesized polypeptide
      sequence

<400> SEQUENCE: 27

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

His Ala Val Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Thr Leu
    50                  55                  60

Gln Asp Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Leu Ala Arg Ala Thr Ala Met Asp Val Trp Gly Glu Gly
            100                 105                 110

Thr Leu Val Thr Val Ser Ser Ala Ser Thr Lys Gly Pro Ser Val Phe
        115                 120                 125
```

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Ala His Tyr Thr Gln Lys Ser Leu Ser Leu Ser Pro
        435                 440                 445

<210> SEQ ID NO 28
<211> LENGTH: 214
<212> TYPE: PRT
<213> ORGANISM: Artificial
<220> FEATURE:
<223> OTHER INFORMATION: An artificially synthesized polypeptide
      sequence

<400> SEQUENCE: 28

Asp Ile Gln Met Thr Gln Ser Pro Ser Ser Leu Ser Ala Ser Val Gly
1               5                   10                  15

Asp Ser Val Thr Ile Thr Cys Gln Ala Ser Arg Asp Ile Ser Ser His
            20                  25                  30

Leu Asn Trp Tyr Gln Gln Lys Pro Gly Lys Ala Pro Glu Leu Leu Ile

```
                    35                  40                  45
Tyr Tyr Gly Ser His Leu Leu Ser Gly Val Pro Ser Arg Phe Ser Gly
 50                  55                  60

Ser Gly Ser Gly Thr Asp Phe Thr Phe Thr Ile Ser Ser Leu Glu Ala
 65                  70                  75                  80

Glu Asp Ala Ala Thr Tyr Tyr Cys Gly Gln Gly Asn Arg Leu Pro Tyr
                     85                  90                  95

Thr Phe Gly Gln Gly Thr Lys Val Glu Ile Glu Arg Thr Val Ala Ala
                    100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 29
<211> LENGTH: 214
<212> TYPE: PRT
<213> ORGANISM: Artificial
<220> FEATURE:
<223> OTHER INFORMATION: An artificially synthesized polypeptide
      sequence

<400> SEQUENCE: 29

Asp Ile Gln Met Thr Gln Ser Pro Ser Ser Leu Ser Ala Ser Val Gly
 1               5                  10                  15

Asp Ser Val Thr Ile Thr Cys Gln Ala Ser Thr Asp Ile Ser Ser His
                 20                  25                  30

Leu Asn Trp Tyr Gln Gln Lys Pro Gly Lys Ala Pro Glu Leu Leu Ile
             35                  40                  45

Tyr Tyr Gly Ser His Leu Leu Ser Gly Val Pro Ser Arg Phe Ser Gly
 50                  55                  60

Ser Gly Ser Gly Thr Asp Phe Thr Phe Thr Ile Ser Ser Leu Glu Ala
 65                  70                  75                  80

Glu Asp Ala Ala Thr Tyr Tyr Cys Gly Gln Gly Asn Arg Leu Pro Tyr
                     85                  90                  95

Thr Phe Gly Gln Gly Thr Lys Val Glu Ile Glu Arg Thr Val Ala Ala
                    100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 30
<211> LENGTH: 214
<212> TYPE: PRT
<213> ORGANISM: Artificial
<220> FEATURE:
<223> OTHER INFORMATION: An artificially synthesized polypeptide
      sequence

<400> SEQUENCE: 30

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Leu Glu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 31
<211> LENGTH: 324
<212> TYPE: PRT
<213> ORGANISM: Artificial
<220> FEATURE:
<223> OTHER INFORMATION: An artificially synthesized polypeptide
      sequence

<400> SEQUENCE: 31

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
            210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Glu Gly Asn Val Phe Ser Cys
            290                 295                 300

Ser Val Met His Glu Ala Leu His Ala His Tyr Thr Gln Lys Ser Leu
305                 310                 315                 320

Ser Leu Ser Pro

<210> SEQ ID NO 32
<211> LENGTH: 324
<212> TYPE: PRT
<213> ORGANISM: Artificial
<220> FEATURE:
<223> OTHER INFORMATION: An artificially synthesized polypeptide
      sequence

<400> SEQUENCE: 32

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Glu Gly Asn Val Phe Ser Cys
    290                 295                 300

Ser Val Met His Glu Ala Leu His Ala His Tyr Thr Gln Lys Ser Leu
305                 310                 315                 320

Ser Leu Ser Pro

<210> SEQ ID NO 33
<211> LENGTH: 328
<212> TYPE: PRT
<213> ORGANISM: Artificial
<220> FEATURE:
<223> OTHER INFORMATION: An artificially synthesized polypeptide
      sequence

<400> SEQUENCE: 33

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Ala His Tyr Thr
305                 310                 315                 320

Gln Lys Ser Leu Ser Leu Ser Pro
                325

<210> SEQ ID NO 34
<211> LENGTH: 107
<212> TYPE: PRT
<213> ORGANISM: Artificial
<220> FEATURE:
<223> OTHER INFORMATION: An artificially synthesized polypeptide
      sequence

<400> SEQUENCE: 34

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 35
```

<211> LENGTH: 107
<212> TYPE: PRT
<213> ORGANISM: Artificial
<220> FEATURE:
<223> OTHER INFORMATION: An artificially synthesized polypeptide sequence

<400> SEQUENCE: 35

Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105

<210> SEQ ID NO 36
<211> LENGTH: 107
<212> TYPE: PRT
<213> ORGANISM: Artificial
<220> FEATURE:
<223> OTHER INFORMATION: An artificially synthesized polypeptide sequence

<400> SEQUENCE: 36

Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105

<210> SEQ ID NO 37
<211> LENGTH: 327
<212> TYPE: DNA
<213> ORGANISM: Homo sapiens

<400> SEQUENCE: 37
cgtacggtgg ctgcaccatc tgtcttcatc ttcccgccat ctgatgagca gttgaaatct     60
ggaactgcct ctgttgtgtg cctgctgaat aacttctatc ccagagaggc caaagtacag    120
tggaaggtgg ataacgccct ccaatcgggt aactcccagg agagtgtcac agagcaggac    180
agcaaggaca gcacctacag cctcagcagc accctgacgc tgagcaaagc agactacgag    240
aaacacaaag tctacgcctg cgaagtcacc catcagggcc tgagctcgcc cgtcacaaag    300
agcttcaaca ggggagagtg ttgataa 327

<210> SEQ ID NO 38
<211> LENGTH: 107
<212> TYPE: PRT
<213> ORGANISM: Homo sapiens

<400> SEQUENCE: 38

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 39
<211> LENGTH: 990
<212> TYPE: DNA
<213> ORGANISM: Homo sapiens

<400> SEQUENCE: 39
gctagcacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa                                      990

<210> SEQ ID NO 40
<211> LENGTH: 330
<212> TYPE: PRT
<213> ORGANISM: Homo sapiens

<400> SEQUENCE: 40

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 41
<211> LENGTH: 984
<212> TYPE: DNA
<213> ORGANISM: Homo sapiens

<400> SEQUENCE: 41

```
gctagcacca agggcccatc ggtcttcccc ctggcgccct cctccaagag cacctccgag    60
agcacagcgg ccctgggctg cctggtcaag gactacttcc ccgaaccggt gacggtgtcg   120
tggaactcag gcgctctgac cagcggcgtg cacaccttcc cggctgtcct acagtcctca   180
```

-continued

```
ggactctact ccctcagcag cgtggtgacc gtgccctcca gcaacttcgg cacccagacc    240
tacacctgca acgtagatca caagcccagc aacaccaagg tggacaagac agttgagcgc    300
aaatcttgtg tcgagtgccc accgtgccca gcaccacctg tggcaggacc gtcagtcttc    360
ctcttccccc caaaacccaa ggacaccctc atgatctccc ggacccctga ggtcacgtgc    420
gtggtggtgg acgtgagcca cgaagacccc gaggtccagt tcaactggta cgtggacggc    480
gtggaggtgc ataatgccaa gacaaagcca cgggaggagc agttcaacag cacgttccgt    540
gtggtcagcg tcctcaccgt cgtgcaccag gactggctga acggcaagga gtacaagtgc    600
aaggtctcca acaaaggcct cccagccccc atcgagaaaa ccatctccaa aaccaaaggg    660
cagccccgag aaccacaggt gtacaccctg cccccatccc gggaggagat gaccaagaac    720
caggtcagcc tgacctgcct ggtcaaaggc ttctacccca gcgacatcgc cgtggagtgg    780
gagagcaatg ggcagccgga gaacaactac aagaccacac ctcccatgct ggactccgac    840
ggctccttct tcctctacag caagctcacc gtggacaaga gcaggtggca gcagggaac    900 gtcttctcat gctccgtgat gcatgaggct ctgcacaacc actacacaca gaagagcctc    960
tccctgtctc cgggtaaatg ataa                                          984
```

<210> SEQ ID NO 42
<211> LENGTH: 326
<212> TYPE: PRT
<213> ORGANISM: Homo sapiens

<400> SEQUENCE: 42

```
Ala Ser Thr Lys Gly Pro Ser Val Phe Pro Leu Ala Pro Ser Ser Lys
1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220
```

```
Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
        260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
            325
```

<210> SEQ ID NO 43
<211> LENGTH: 995
<212> TYPE: DNA
<213> ORGANISM: Homo sapiens

<400> SEQUENCE: 43

| | | | | | |
|---|---|---|---|---|---|
| gctagcacca | agggcccatc | cgtcttcccc | ctggcgccct | gctccaggag | cacctccgag | 60 |
| agcacagccg | ccctgggctg | cctggtcaag | gactacttcc | ccgaaccggt | gacggtgtcg | 120 |
| tggaactcag | gcgccctgac | cagcggcgtg | cacaccttcc | cggctgtcct | acagtcctca | 180 |
| ggactctact | ccctcagcag | cgtggtgacc | gtgccctcca | gcagcttggg | cacgaagacc | 240 |
| tacacctgca | acgtagatca | caagcccagc | aacaccaagg | tggacaagag | agttgagtcc | 300 |
| aaatatggtc | ccccatgccc | accatgccca | gcacctgagt | tcctgggggg | accatcagtc | 360 |
| ttcctgttcc | ccccaaaacc | caaggacact | ctcatgatct | cccggacccc | tgaggtcacg | 420 |
| tgcgtggtgg | tggacgtgag | ccaggaagac | cccgaggtcc | agttcaactg | gtacgtggat | 480 |
| ggcgtggagg | tgcataatgc | caagacaaag | ccgcgggagg | agcagttcaa | cagcacgtac | 540 |
| cgtgtggtca | gcgtcctcac | cgtcctgcac | caggactggc | tgaacggcaa | ggagtacaag | 600 |
| tgcaaggtct | ccaacaaagg | cctcccgtcc | tccatcgaga | aaaccatctc | caaagccaaa | 660 |
| gggcagcccc | gagagccaca | ggtgtacacc | ctgcccccat | cccaggagga | gatgaccaag | 720 |
| aaccaggtca | gcctgacctg | cctggtcaaa | ggcttctacc | ccagcgacat | cgccgtggag | 780 |
| tgggagagca | atgggcagcc | ggagaacaac | tacaagacca | cgcctcccgt | gctggactcc | 840 |
| gacggctcct | tcttcctcta | cagcaggcta | accgtggaca | agagcaggtg | gcaggagggg | 900 |
| aatgtcttct | catgctccgt | gatgcatgag | gctctgcaca | accactacac | acagaagagc | 960 |
| ctctccctgt | ctctgggtta | atgataagcg | gccgc | | | 995 |

<210> SEQ ID NO 44
<211> LENGTH: 326
<212> TYPE: PRT
<213> ORGANISM: Homo sapiens

<400> SEQUENCE: 44

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 45
<211> LENGTH: 4
<212> TYPE: PRT
<213> ORGANISM: Artificial
<220> FEATURE:
<223> OTHER INFORMATION: An artificially synthesized polypeptide
      sequence

<400> SEQUENCE: 45

Gly Gly Gly Ser
1

<210> SEQ ID NO 46
<211> LENGTH: 4
<212> TYPE: PRT
<213> ORGANISM: Artificial
<220> FEATURE:
<223> OTHER INFORMATION: An artificially synthesized polypeptide
      sequence

<400> SEQUENCE: 46

Ser Gly Gly Gly
1

<210> SEQ ID NO 47
<211> LENGTH: 5
<212> TYPE: PRT
<213> ORGANISM: Artificial
<220> FEATURE:
<223> OTHER INFORMATION: An artificially synthesized polypeptide
      sequence

<400> SEQUENCE: 47

Gly Gly Gly Gly Ser
1               5

<210> SEQ ID NO 48
<211> LENGTH: 5
<212> TYPE: PRT
<213> ORGANISM: Artificial
<220> FEATURE:
<223> OTHER INFORMATION: An artificially synthesized polypeptide
      sequence

<400> SEQUENCE: 48

Ser Gly Gly Gly Gly
1               5

<210> SEQ ID NO 49
<211> LENGTH: 6
<212> TYPE: PRT
<213> ORGANISM: Artificial
<220> FEATURE:
<223> OTHER INFORMATION: An artificially synthesized polypeptide
      sequence

<400> SEQUENCE: 49

Gly Gly Gly Gly Gly Ser
1               5

<210> SEQ ID NO 50
<211> LENGTH: 6
<212> TYPE: PRT
<213> ORGANISM: Artificial
<220> FEATURE:
<223> OTHER INFORMATION: An artificially synthesized polypeptide
      sequence

<400> SEQUENCE: 50

Ser Gly Gly Gly Gly Gly
1               5

<210> SEQ ID NO 51
<211> LENGTH: 7
<212> TYPE: PRT
<213> ORGANISM: Artificial
<220> FEATURE:
<223> OTHER INFORMATION: An artificially synthesized polypeptide
      sequence

<400> SEQUENCE: 51

Gly Gly Gly Gly Gly Gly Ser
1               5

<210> SEQ ID NO 52
<211> LENGTH: 7
<212> TYPE: PRT
<213> ORGANISM: Artificial

```
<220> FEATURE:
<223> OTHER INFORMATION: An artificially synthesized polypeptide
      sequence

<400> SEQUENCE: 52

Ser Gly Gly Gly Gly Gly
1               5

<210> SEQ ID NO 53
<211> LENGTH: 449
<212> TYPE: PRT
<213> ORGANISM: Artificial
<220> FEATURE:
<223> OTHER INFORMATION: An artificially synthesized polypeptide
      sequence

<400> SEQUENCE: 53

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 54
<211> LENGTH: 214
<212> TYPE: PRT
<213> ORGANISM: Artificial
<220> FEATURE:
<223> OTHER INFORMATION: An artificially synthesized polypeptide
      sequence

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
            85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 55
<211> LENGTH: 449
<212> TYPE: PRT
<213> ORGANISM: Artificial
<220> FEATURE:
<223> OTHER INFORMATION: An artificially synthesized polypeptide
      sequence

<400> SEQUENCE: 55

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Val Leu Ala Arg Ile Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
```

```
                355                 360                 365
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 56
<211> LENGTH: 214
<212> TYPE: PRT
<213> ORGANISM: Artificial
<220> FEATURE:
<223> OTHER INFORMATION: An artificially synthesized polypeptide
      sequence

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gly Gln Gly Asn Arg Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 57
<211> LENGTH: 449
<212> TYPE: PRT
<213> ORGANISM: Artificial
<220> FEATURE:
<223> OTHER INFORMATION: An artificially synthesized polypeptide
```

-continued sequence

<400> SEQUENCE: 57

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

His Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

```
Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
        435                 440                 445

Lys

<210> SEQ ID NO 58
<211> LENGTH: 214
<212> TYPE: PRT
<213> ORGANISM: Artificial
<220> FEATURE:
<223> OTHER INFORMATION: An artificially synthesized polypeptide
      sequence

<400> SEQUENCE: 58

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Leu His Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Gly Asn Ser Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 59
<211> LENGTH: 7
<212> TYPE: PRT
<213> ORGANISM: Artificial
<220> FEATURE:
<223> OTHER INFORMATION: An artificially synthesized polypeptide
      sequence

<400> SEQUENCE: 59

Tyr Thr Ser Arg Leu His Ser
1               5
```

```
<210> SEQ ID NO 60
<211> LENGTH: 7
<212> TYPE: PRT
<213> ORGANISM: Artificial
<220> FEATURE:
<223> OTHER INFORMATION: An artificially synthesized polypeptide
      sequence

<400> SEQUENCE: 60

Tyr Gly Ser Glu Leu His Ser
1               5

<210> SEQ ID NO 61
<211> LENGTH: 30
<212> TYPE: PRT
<213> ORGANISM: Artificial
<220> FEATURE:
<223> OTHER INFORMATION: An artificially synthesized polypeptide
      sequence

<400> SEQUENCE: 61

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr
            20                  25                  30

<210> SEQ ID NO 62
<211> LENGTH: 30
<212> TYPE: PRT
<213> ORGANISM: Artificial
<220> FEATURE:
<223> OTHER INFORMATION: An artificially synthesized polypeptide
      sequence

<400> SEQUENCE: 62

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser
            20                  25                  30

<210> SEQ ID NO 63
<211> LENGTH: 32
<212> TYPE: PRT
<213> ORGANISM: Artificial
<220> FEATURE:
<223> OTHER INFORMATION: An artificially synthesized polypeptide
      sequence

<400> SEQUENCE: 63

Arg Val Thr Met Leu Arg Asp Thr Ser Lys Asn Gln Phe Ser Leu Arg
1               5                   10                  15

Leu Ser Ser Val Thr Ala Ala Asp Thr Ala Val Tyr Tyr Cys Ala Arg
            20                  25                  30

<210> SEQ ID NO 64
<211> LENGTH: 32
<212> TYPE: PRT
<213> ORGANISM: Artificial
<220> FEATURE:
<223> OTHER INFORMATION: An artificially synthesized polypeptide
      sequence

<400> SEQUENCE: 64

Arg Val Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
```

<210> SEQ ID NO 65
<211> LENGTH: 30
<212> TYPE: PRT
<213> ORGANISM: Artificial
<220> FEATURE:
<223> OTHER INFORMATION: An artificially synthesized polypeptide
    sequence

<400> SEQUENCE: 65

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser
            20                  25                  30

<210> SEQ ID NO 66
<211> LENGTH: 449
<212> TYPE: PRT
<213> ORGANISM: Artificial
<220> FEATURE:
<223> OTHER INFORMATION: An artificially synthesized polypeptide
    sequence

<400> SEQUENCE: 66

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala His Ser Trp Val Arg Gln Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp

```
                    260                 265                 270
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 67
<211> LENGTH: 214
<212> TYPE: PRT
<213> ORGANISM: Artificial
<220> FEATURE:
<223> OTHER INFORMATION: An artificially synthesized polypeptide
      sequence

<400> SEQUENCE: 67

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln His Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu His Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                         165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 68
<211> LENGTH: 448
<212> TYPE: PRT
<213> ORGANISM: Artificial
<220> FEATURE:
<223> OTHER INFORMATION: An artificially synthesized polypeptide
      sequence

<400> SEQUENCE: 68

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 69
<211> LENGTH: 447
<212> TYPE: PRT
<213> ORGANISM: Artificial
<220> FEATURE:
<223> OTHER INFORMATION: An artificially synthesized polypeptide
      sequence

<400> SEQUENCE: 69

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220
```

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 70
<211> LENGTH: 445
<212> TYPE: PRT
<213> ORGANISM: Artificial
<220> FEATURE:
<223> OTHER INFORMATION: An artificially synthesized polypeptide
      sequence

<400> SEQUENCE: 70

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Glu Ser Thr Ala Ala Leu
```

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 71
<211> LENGTH: 445
<212> TYPE: PRT
<213> ORGANISM: Artificial
<220> FEATURE:
<223> OTHER INFORMATION: An artificially synthesized polypeptide
      sequence

<400> SEQUENCE: 71

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
                20                  25                  30

His Ala Trp Ser Trp Val Arg Gln Pro Pro Gly Arg Gly Leu Glu Trp
            35                  40                  45

-continued

```
Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 72
<211> LENGTH: 443
<212> TYPE: PRT
```

```
<213> ORGANISM: Artificial
<220> FEATURE:
<223> OTHER INFORMATION: An artificially synthesized polypeptide
      sequence

<400> SEQUENCE: 72

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380
```

```
Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
            405                 410                 415

Glu Gly Asn Val Phe Ser Cys Ser Val Met His Glu Ala Leu His Asn
        420                 425                 430

His Tyr Thr Gln Lys Ser Leu Ser Leu Ser Pro
        435                 440

<210> SEQ ID NO 73
<211> LENGTH: 449
<212> TYPE: PRT
<213> ORGANISM: Artificial
<220> FEATURE:
<223> OTHER INFORMATION: An artificially synthesized polypeptide
      sequence

<400> SEQUENCE: 73

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
            85                  90                  95

Ala Arg Ser Leu Ala Arg Thr Thr Ala Met Asp Tyr Trp Gly Gln Gly
        100                 105                 110

Ser Leu Val Thr Val Ser Ser Ala Ser Thr Lys Gly Pro Ser Val Phe
    115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 74
<211> LENGTH: 447
<212> TYPE: PRT
<213> ORGANISM: Artificial
<220> FEATURE:
<223> OTHER INFORMATION: An artificially synthesized polypeptide
      sequence

<400> SEQUENCE: 74

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
            85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
        195                 200                 205
```

```
Ser Asn Thr Lys Val Asp Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Ala His Tyr Thr Gln Lys Ser Leu Ser Leu Ser Pro
                435                 440                 445

<210> SEQ ID NO 75
<211> LENGTH: 443
<212> TYPE: PRT
<213> ORGANISM: Artificial
<220> FEATURE:
<223> OTHER INFORMATION: An artificially synthesized polypeptide
      sequence

<400> SEQUENCE: 75

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
                20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
        50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
```

```
            115                 120                 125
Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Ala
            420                 425                 430

His Tyr Thr Gln Lys Ser Leu Ser Leu Ser Pro
        435                 440

<210> SEQ ID NO 76
<211> LENGTH: 449
<212> TYPE: PRT
<213> ORGANISM: Artificial
<220> FEATURE:
<223> OTHER INFORMATION: An artificially synthesized polypeptide
      sequence

<400> SEQUENCE: 76

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30
```

-continued

His Ala Val Ser Trp Val Arg Gln Pro Pro Gly Glu Gly Leu Glu Trp
                35                  40                  45

Ile Gly Phe Ile Ser Tyr Ser Gly Ile Thr Asn Tyr Asn Pro Thr Leu
 50                  55                  60

Gln Asp Arg Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Leu Ala Arg Ala Thr Ala Met Asp Val Trp Gly Glu Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
                210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 77
<211> LENGTH: 446
<212> TYPE: PRT
<213> ORGANISM: Artificial
<220> FEATURE:
<223> OTHER INFORMATION: An artificially synthesized polypeptide sequence

<400> SEQUENCE: 77

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Arg |
| 1 | | | | 5 | | | | | 10 | | | | | 15 | |
| Ser | Leu | Arg | Leu | Ser | Cys | Ala | Ala | Ser | Arg | Phe | Thr | Phe | Asp | Asp | Tyr |
| | | | 20 | | | | | 25 | | | | | 30 | | |
| Ala | Met | His | Trp | Val | Arg | Gln | Ala | Pro | Gly | Lys | Gly | Leu | Glu | Trp | Val |
| | | | 35 | | | | | 40 | | | | | 45 | | |
| Ser | Gly | Ile | Ser | Trp | Asn | Ser | Gly | Arg | Ile | Gly | Tyr | Ala | Asp | Ser | Val |
| | 50 | | | | | 55 | | | | | 60 | | | | |
| Lys | Gly | Arg | Phe | Thr | Ile | Ser | Arg | Asp | Asn | Ala | Glu | Asn | Ser | Leu | Phe |
| 65 | | | | | 70 | | | | | 75 | | | | | 80 |
| Leu | Gln | Met | Asn | Gly | Leu | Arg | Ala | Glu | Asp | Thr | Ala | Leu | Tyr | Tyr | Cys |
| | | | | 85 | | | | | 90 | | | | | 95 | |
| Ala | Lys | Gly | Arg | Asp | Ser | Phe | Asp | Ile | Trp | Gly | Gln | Gly | Thr | Met | Val |
| | | | 100 | | | | | 105 | | | | | 110 | | |
| Thr | Val | Ser | Ser | Ala | Ser | Thr | Lys | Gly | Pro | Ser | Val | Phe | Pro | Leu | Ala |
| | | | 115 | | | | | 120 | | | | | 125 | | |
| Pro | Ser | Ser | Lys | Ser | Thr | Ser | Gly | Gly | Thr | Ala | Ala | Leu | Gly | Cys | Leu |
| 130 | | | | | 135 | | | | | 140 | | | | | |
| Val | Lys | Asp | Tyr | Phe | Pro | Glu | Pro | Val | Thr | Val | Ser | Trp | Asn | Ser | Gly |
| 145 | | | | | 150 | | | | | 155 | | | | | 160 |
| Ala | Leu | Thr | Ser | Gly | Val | His | Thr | Phe | Pro | Ala | Val | Leu | Gln | Ser | Ser |
| | | | | 165 | | | | | 170 | | | | | 175 | |
| Gly | Leu | Tyr | Ser | Leu | Ser | Ser | Val | Val | Thr | Val | Pro | Ser | Ser | Ser | Leu |
| | | | 180 | | | | | 185 | | | | | 190 | | |
| Gly | Thr | Gln | Thr | Tyr | Ile | Cys | Asn | Val | Asn | His | Lys | Pro | Ser | Asn | Thr |
| | | | 195 | | | | | 200 | | | | | 205 | | |
| Lys | Val | Asp | Lys | Lys | Val | Glu | Pro | Lys | Ser | Cys | Asp | Lys | Thr | His | Thr |
| 210 | | | | | 215 | | | | | 220 | | | | | |
| Cys | Pro | Pro | Cys | Pro | Ala | Pro | Glu | Leu | Leu | Gly | Gly | Pro | Ser | Val | Phe |
| 225 | | | | | 230 | | | | | 235 | | | | | 240 |
| Leu | Phe | Pro | Pro | Lys | Pro | Lys | Asp | Thr | Leu | Met | Ile | Ser | Arg | Thr | Pro |
| | | | | 245 | | | | | 250 | | | | | 255 | |
| Glu | Val | Thr | Cys | Val | Val | Val | Asp | Val | Ser | His | Glu | Asp | Pro | Glu | Val |
| | | | 260 | | | | | 265 | | | | | 270 | | |
| Lys | Phe | Asn | Trp | Tyr | Val | Asp | Gly | Val | Glu | Val | His | Asn | Ala | Lys | Thr |
| | | | | 275 | | | | | 280 | | | | | 285 | |
| Lys | Pro | Arg | Glu | Glu | Gln | Tyr | Asn | Ser | Thr | Tyr | Arg | Val | Val | Ser | Val |
| | | | 290 | | | | | 295 | | | | | 300 | | |
| Leu | Thr | Val | Leu | His | Gln | Asp | Trp | Leu | Asn | Gly | Lys | Glu | Tyr | Lys | Cys |
| 305 | | | | | 310 | | | | | 315 | | | | | 320 |
| Lys | Val | Ser | Asn | Lys | Ala | Leu | Pro | Ala | Pro | Ile | Glu | Lys | Thr | Ile | Ser |
| | | | | 325 | | | | | 330 | | | | | 335 | |
| Lys | Ala | Lys | Gly | Gln | Pro | Arg | Glu | Pro | Gln | Val | Tyr | Thr | Leu | Pro | Pro |
| | | | 340 | | | | | 345 | | | | | 350 | | |
| Ser | Arg | Asp | Glu | Leu | Thr | Lys | Asn | Gln | Val | Ser | Leu | Thr | Cys | Leu | Val |

-continued

```
                355                 360                 365
Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
                435                 440                 445

<210> SEQ ID NO 78
<211> LENGTH: 214
<212> TYPE: PRT
<213> ORGANISM: Artificial
<220> FEATURE:
<223> OTHER INFORMATION: An artificially synthesized polypeptide
      sequence

<400> SEQUENCE: 78

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Ala Asn Ser Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 79
<211> LENGTH: 267
<212> TYPE: PRT
<213> ORGANISM: Homo sapiens

<400> SEQUENCE: 79

Ala Glu Ser His Leu Ser Leu Leu Tyr His Leu Thr Ala Val Ser Ser
```

```
              1               5              10              15
            Pro Ala Pro Gly Thr Pro Ala Phe Trp Val Ser Gly Trp Leu Gly Pro
                           20              25              30

Gln Gln Tyr Leu Ser Tyr Asn Ser Leu Arg Gly Glu Ala Glu Pro Cys
                           35              40              45

Gly Ala Trp Val Trp Glu Asn Gln Val Ser Trp Tyr Trp Glu Lys Glu
                    50              55              60

Thr Thr Asp Leu Arg Ile Lys Glu Lys Leu Phe Leu Glu Ala Phe Lys
             65                  70              75              80

Ala Leu Gly Gly Lys Gly Pro Tyr Thr Leu Gln Gly Leu Leu Gly Cys
                           85              90              95

Glu Leu Gly Pro Asp Asn Thr Ser Val Pro Thr Ala Lys Phe Ala Leu
                          100             105             110

Asn Gly Glu Glu Phe Met Asn Phe Asp Leu Lys Gln Gly Thr Trp Gly
                          115             120             125

Gly Asp Trp Pro Glu Ala Leu Ala Ile Ser Gln Arg Trp Gln Gln Gln
                 130             135             140

Asp Lys Ala Ala Asn Lys Glu Leu Thr Phe Leu Leu Phe Ser Cys Pro
            145             150             155             160

His Arg Leu Arg Glu His Leu Glu Arg Gly Arg Gly Asn Leu Glu Trp
                          165             170             175

Lys Glu Pro Pro Ser Met Arg Leu Lys Ala Arg Pro Ser Ser Pro Gly
                          180             185             190

Phe Ser Val Leu Thr Cys Ser Ala Phe Ser Phe Tyr Pro Pro Glu Leu
                          195             200             205

Gln Leu Arg Phe Leu Arg Asn Gly Leu Ala Ala Gly Thr Gly Gln Gly
                          210             215             220

Asp Phe Gly Pro Asn Ser Asp Gly Ser Phe His Ala Ser Ser Ser Leu
            225             230             235             240

Thr Val Lys Ser Gly Asp Glu His His Tyr Cys Cys Ile Val Gln His
                          245             250             255

Ala Gly Leu Ala Gln Pro Leu Arg Val Glu Leu
                          260             265

<210> SEQ ID NO 80
<211> LENGTH: 99
<212> TYPE: PRT
<213> ORGANISM: Homo sapiens

<400> SEQUENCE: 80

Ile Gln Arg Thr Pro Lys Ile Gln Val Tyr Ser Arg His Pro Ala Glu
             1               5              10              15

Asn Gly Lys Ser Asn Phe Leu Asn Cys Tyr Val Ser Gly Phe His Pro
                           20              25              30

Ser Asp Ile Glu Val Asp Leu Leu Lys Asn Gly Glu Arg Ile Glu Lys
                           35              40              45

Val Glu His Ser Asp Leu Ser Phe Ser Lys Asp Trp Ser Phe Tyr Leu
                    50              55              60

Leu Tyr Tyr Thr Glu Phe Thr Pro Thr Glu Lys Asp Glu Tyr Ala Cys
             65                  70              75              80

Arg Val Asn His Val Thr Leu Ser Gln Pro Lys Ile Val Lys Trp Asp
                           85              90              95

Arg Asp Met
```

-continued

<210> SEQ ID NO 81
<211> LENGTH: 16
<212> TYPE: PRT
<213> ORGANISM: Artificial
<220> FEATURE:
<223> OTHER INFORMATION: An artificially synthesized polypeptide
      sequence

<400> SEQUENCE: 81

Tyr Ile Ser Tyr Ser Gly Ile Thr Thr Tyr Asn Pro Ser Leu Lys Ser
1               5                   10                  15

<210> SEQ ID NO 82
<211> LENGTH: 16
<212> TYPE: PRT
<213> ORGANISM: Artificial
<220> FEATURE:
<223> OTHER INFORMATION: An artificially synthesized polypeptide
      sequence

<400> SEQUENCE: 82

Phe Ile Ser Tyr Ser Gly Ile Thr Thr Tyr Asn Pro Ser Leu Lys Ser
1               5                   10                  15

<210> SEQ ID NO 83
<211> LENGTH: 16
<212> TYPE: PRT
<213> ORGANISM: Artificial
<220> FEATURE:
<223> OTHER INFORMATION: An artificially synthesized polypeptide
      sequence

<400> SEQUENCE: 83

Tyr Ile Ser Tyr Ser Gly Ile Thr Asn Tyr Asn Pro Ser Leu Lys Ser
1               5                   10                  15

<210> SEQ ID NO 84
<211> LENGTH: 10
<212> TYPE: PRT
<213> ORGANISM: Artificial
<220> FEATURE:
<223> OTHER INFORMATION: An artificially synthesized polypeptide
      sequence

<400> SEQUENCE: 84

Ser Leu Ala Arg Thr Thr Ala Met Asp Tyr
1               5                   10

<210> SEQ ID NO 85
<211> LENGTH: 10
<212> TYPE: PRT
<213> ORGANISM: Artificial
<220> FEATURE:
<223> OTHER INFORMATION: An artificially synthesized polypeptide
      sequence

<400> SEQUENCE: 85

Leu Leu Ala Arg Thr Thr Ala Met Asp Tyr
1               5                   10

<210> SEQ ID NO 86
<211> LENGTH: 10
<212> TYPE: PRT
<213> ORGANISM: Artificial
<220> FEATURE:
<223> OTHER INFORMATION: An artificially synthesized polypeptide
      sequence

<400> SEQUENCE: 86

Ser Leu Ala Arg Ala Thr Ala Met Asp Tyr
1               5                   10

<210> SEQ ID NO 87
<211> LENGTH: 11
<212> TYPE: PRT
<213> ORGANISM: Artificial
<220> FEATURE:
<223> OTHER INFORMATION: An artificially synthesized polypeptide
      sequence

<400> SEQUENCE: 87

Arg Ala Ser Gln Asp Ile Ser Ser Tyr Leu Asn
1               5                   10

<210> SEQ ID NO 88
<211> LENGTH: 11
<212> TYPE: PRT
<213> ORGANISM: Artificial
<220> FEATURE:
<223> OTHER INFORMATION: An artificially synthesized polypeptide
      sequence

<400> SEQUENCE: 88

Arg Ala Ser Thr Asp Ile Ser Ser Tyr Leu Asn
1               5                   10

<210> SEQ ID NO 89
<211> LENGTH: 11
<212> TYPE: PRT
<213> ORGANISM: Artificial
<220> FEATURE:
<223> OTHER INFORMATION: An artificially synthesized polypeptide
      sequence

<400> SEQUENCE: 89

Arg Ala Ser Arg Asp Ile Ser Ser Tyr Leu Asn
1               5                   10

<210> SEQ ID NO 90
<211> LENGTH: 9
<212> TYPE: PRT
<213> ORGANISM: Artificial
<220> FEATURE:
<223> OTHER INFORMATION: An artificially synthesized polypeptide
      sequence

<400> SEQUENCE: 90

Gln Gln Gly Asn Thr Leu Pro Tyr Thr
1               5

<210> SEQ ID NO 91
<211> LENGTH: 9
<212> TYPE: PRT
<213> ORGANISM: Artificial
<220> FEATURE:
<223> OTHER INFORMATION: An artificially synthesized polypeptide
      sequence

<400> SEQUENCE: 91

Gly Gln Gly Asn Thr Leu Pro Tyr Thr
1               5

<210> SEQ ID NO 92
<211> LENGTH: 9
<212> TYPE: PRT
<213> ORGANISM: Artificial

<220> FEATURE:
<223> OTHER INFORMATION: An artificially synthesized polypeptide
      sequence

<400> SEQUENCE: 92

Gln Gln Gly Asn Arg Leu Pro Tyr Thr
1               5

<210> SEQ ID NO 93
<211> LENGTH: 30
<212> TYPE: PRT
<213> ORGANISM: Artificial
<220> FEATURE:
<223> OTHER INFORMATION: An artificially synthesized polypeptide
      sequence

<400> SEQUENCE: 93

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr
            20                  25                  30

<210> SEQ ID NO 94
<211> LENGTH: 30
<212> TYPE: PRT
<213> ORGANISM: Artificial
<220> FEATURE:
<223> OTHER INFORMATION: An artificially synthesized polypeptide
      sequence

<400> SEQUENCE: 94

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser
            20                  25                  30

<210> SEQ ID NO 95
<211> LENGTH: 6
<212> TYPE: PRT
<213> ORGANISM: Artificial
<220> FEATURE:
<223> OTHER INFORMATION: An artificially synthesized polypeptide
      sequence

<400> SEQUENCE: 95

Ser Asp His Ala Trp Ser
1               5

<210> SEQ ID NO 96
<211> LENGTH: 6
<212> TYPE: PRT
<213> ORGANISM: Artificial
<220> FEATURE:
<223> OTHER INFORMATION: An artificially synthesized polypeptide
      sequence

<400> SEQUENCE: 96

Asp Asp His Ala Trp Ser
1               5

<210> SEQ ID NO 97
<211> LENGTH: 14
<212> TYPE: PRT
<213> ORGANISM: Artificial
<220> FEATURE:
<223> OTHER INFORMATION: An artificially synthesized polypeptide
      sequence

```
<400> SEQUENCE: 97

Trp Val Arg Gln Pro Pro Gly Arg Gly Leu Glu Trp Ile Gly
1               5                   10

<210> SEQ ID NO 98
<211> LENGTH: 14
<212> TYPE: PRT
<213> ORGANISM: Artificial
<220> FEATURE:
<223> OTHER INFORMATION: An artificially synthesized polypeptide
      sequence

<400> SEQUENCE: 98

Trp Val Arg Gln Pro Pro Gly Glu Gly Leu Glu Trp Ile Gly
1               5                   10

<210> SEQ ID NO 99
<211> LENGTH: 16
<212> TYPE: PRT
<213> ORGANISM: Artificial
<220> FEATURE:
<223> OTHER INFORMATION: An artificially synthesized polypeptide
      sequence

<400> SEQUENCE: 99

Tyr Ile Ser Tyr Ser Gly Ile Thr Thr Tyr Asn Pro Ser Leu Gln Asp
1               5                   10                  15

<210> SEQ ID NO 100
<211> LENGTH: 11
<212> TYPE: PRT
<213> ORGANISM: Artificial
<220> FEATURE:
<223> OTHER INFORMATION: An artificially synthesized polypeptide
      sequence

<400> SEQUENCE: 100

Trp Gly Gln Gly Ser Leu Val Thr Val Ser Ser
1               5                   10

<210> SEQ ID NO 101
<211> LENGTH: 11
<212> TYPE: PRT
<213> ORGANISM: Artificial
<220> FEATURE:
<223> OTHER INFORMATION: An artificially synthesized polypeptide
      sequence

<400> SEQUENCE: 101

Trp Gly Glu Gly Thr Leu Val Thr Val Ser Ser
1               5                   10

<210> SEQ ID NO 102
<211> LENGTH: 23
<212> TYPE: PRT
<213> ORGANISM: Artificial
<220> FEATURE:
<223> OTHER INFORMATION: An artificially synthesized polypeptide
      sequence

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys
            20
```

```
<210> SEQ ID NO 103
<211> LENGTH: 23
<212> TYPE: PRT
<213> ORGANISM: Artificial
<220> FEATURE:
<223> OTHER INFORMATION: An artificially synthesized polypeptide
      sequence

<400> SEQUENCE: 103

Asp Ile Gln Met Thr Gln Ser Pro Ser Ser Leu Ser Ala Ser Val Gly
1               5                   10                  15

Asp Ser Val Thr Ile Thr Cys
            20

<210> SEQ ID NO 104
<211> LENGTH: 11
<212> TYPE: PRT
<213> ORGANISM: Artificial
<220> FEATURE:
<223> OTHER INFORMATION: An artificially synthesized polypeptide
      sequence

<400> SEQUENCE: 104

Gln Ala Ser Gln Asp Ile Ser Ser Tyr Leu Asn
1               5                   10

<210> SEQ ID NO 105
<211> LENGTH: 15
<212> TYPE: PRT
<213> ORGANISM: Artificial
<220> FEATURE:
<223> OTHER INFORMATION: An artificially synthesized polypeptide
      sequence

<400> SEQUENCE: 105

Trp Tyr Gln Gln Lys Pro Gly Lys Ala Pro Lys Leu Leu Ile Tyr
1               5                   10                  15

<210> SEQ ID NO 106
<211> LENGTH: 15
<212> TYPE: PRT
<213> ORGANISM: Artificial
<220> FEATURE:
<223> OTHER INFORMATION: An artificially synthesized polypeptide
      sequence

<400> SEQUENCE: 106

Trp Tyr Gln Gln Lys Pro Gly Lys Ala Pro Glu Leu Leu Ile Tyr
1               5                   10                  15

<210> SEQ ID NO 107
<211> LENGTH: 7
<212> TYPE: PRT
<213> ORGANISM: Artificial
<220> FEATURE:
<223> OTHER INFORMATION: An artificially synthesized polypeptide
      sequence

<400> SEQUENCE: 107

Tyr Thr Ser Arg Leu His Ser
1               5

<210> SEQ ID NO 108
<211> LENGTH: 7
<212> TYPE: PRT
<213> ORGANISM: Artificial
<220> FEATURE:
```

```
<223> OTHER INFORMATION: An artificially synthesized polypeptide
      sequence

<400> SEQUENCE: 108

Tyr Thr Ser Glu Leu Glu Ser
1               5

<210> SEQ ID NO 109
<211> LENGTH: 7
<212> TYPE: PRT
<213> ORGANISM: Artificial
<220> FEATURE:
<223> OTHER INFORMATION: An artificially synthesized polypeptide
      sequence

<400> SEQUENCE: 109

Tyr Thr Ser Arg Leu Leu Ser
1               5

<210> SEQ ID NO 110
<211> LENGTH: 32
<212> TYPE: PRT
<213> ORGANISM: Artificial
<220> FEATURE:
<223> OTHER INFORMATION: An artificially synthesized polypeptide
      sequence

<400> SEQUENCE: 110

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 111
<211> LENGTH: 32
<212> TYPE: PRT
<213> ORGANISM: Artificial
<220> FEATURE:
<223> OTHER INFORMATION: An artificially synthesized polypeptide
      sequence

<400> SEQUENCE: 111

Gly Val Pro Ser Arg Phe Ser Gly Ser Gly Ser Gly Thr Asp Phe Thr
1               5                   10                  15

Phe Thr Ile Ser Ser Leu Glu Ala Glu Asp Ala Ala Thr Tyr Tyr Cys
            20                  25                  30

<210> SEQ ID NO 112
<211> LENGTH: 10
<212> TYPE: PRT
<213> ORGANISM: Artificial
<220> FEATURE:
<223> OTHER INFORMATION: An artificially synthesized polypeptide
      sequence

<400> SEQUENCE: 112

Phe Gly Gln Gly Thr Lys Val Glu Ile Lys
1               5                   10

<210> SEQ ID NO 113
<211> LENGTH: 10
<212> TYPE: PRT
<213> ORGANISM: Artificial
<220> FEATURE:
<223> OTHER INFORMATION: An artificially synthesized polypeptide
      sequence
```

```
<400> SEQUENCE: 113

Phe Gly Gln Gly Thr Lys Val Glu Ile Glu
1               5                   10

<210> SEQ ID NO 114
<211> LENGTH: 30
<212> TYPE: PRT
<213> ORGANISM: Artificial
<220> FEATURE:
<223> OTHER INFORMATION: An artificially synthesized polypeptide
      sequence

<400> SEQUENCE: 114

Gln Val Gln Leu Gln Glu Ser Gly Pro Gly Leu Val Arg Pro Ser Gln
1               5                   10                  15

Thr Leu Ser Leu Thr Cys Thr Val Ser Gly His Ser Ile Thr
            20                  25                  30

<210> SEQ ID NO 115
<211> LENGTH: 6
<212> TYPE: PRT
<213> ORGANISM: Artificial
<220> FEATURE:
<223> OTHER INFORMATION: An artificially synthesized polypeptide
      sequence

<400> SEQUENCE: 115

His Asp His Ala Trp Ser
1               5

<210> SEQ ID NO 116
<211> LENGTH: 11
<212> TYPE: PRT
<213> ORGANISM: Artificial
<220> FEATURE:
<223> OTHER INFORMATION: An artificially synthesized polypeptide
      sequence

<400> SEQUENCE: 116

Arg Ala Ser Gln Asp Ile Ser Ser His Leu Asn
1               5                   10

<210> SEQ ID NO 117
<211> LENGTH: 7
<212> TYPE: PRT
<213> ORGANISM: Artificial
<220> FEATURE:
<223> OTHER INFORMATION: An artificially synthesized polypeptide
      sequence

<400> SEQUENCE: 117

Tyr Thr Ser His Leu His Ser
1               5
```